US010968189B2

(12) United States Patent
Horiguchi et al.

(10) Patent No.: US 10,968,189 B2
(45) Date of Patent: Apr. 6, 2021

(54) METHOD FOR PRODUCING 2-HYDRAZINOBENZOTHIAZOLE DERIVATIVE

(71) Applicant: DIC Corporation, Tokyo (JP)

(72) Inventors: Masahiro Horiguchi, Kita-adachi-gun (JP); Junichi Mamiya, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 198 days.

(21) Appl. No.: 16/082,471

(22) PCT Filed: Mar. 16, 2017

(86) PCT No.: PCT/JP2017/010629

§ 371 (c)(1),
(2) Date: Sep. 5, 2018

(87) PCT Pub. No.: WO2017/169839

PCT Pub. Date: Oct. 5, 2017

(65) Prior Publication Data

US 2020/0165215 A1 May 28, 2020

(30) Foreign Application Priority Data

Mar. 30, 2016 (JP) ............................ JP2016-068237

(51) Int. Cl.

| | |
|---|---|
| ***C07D 277/82*** | (2006.01) |
| ***C09K 19/38*** | (2006.01) |
| ***C08F 22/14*** | (2006.01) |
| ***C09K 19/34*** | (2006.01) |

(52) U.S. Cl.
CPC ............ *C07D 277/82* (2013.01); *C08F 22/14* (2013.01); *C09K 19/3497* (2013.01)

(58) Field of Classification Search
CPC ............................ C07D 277/82; C07D 277/62
See application file for complete search history.

(56) References Cited

U.S. PATENT DOCUMENTS

| | | | | |
|---|---|---|---|---|
| 9,207,360 | B2 * | 12/2015 | Sakamoto | C07C 243/20 |
| 10,273,322 | B2 * | 4/2019 | Sakamoto | C07D 277/82 |
| 2014/0142266 | A1 | 5/2014 | Sakamoto et al. | |
| 2014/0235857 | A1 | 8/2014 | Sakamoto et al. | |
| 2015/0232625 | A1 | 8/2015 | Sakamoto | |
| 2016/0200841 | A1 * | 7/2016 | Sakamoto | C07D 277/82 526/257 |
| 2016/0280672 | A1 | 9/2016 | Sakamoto et al. | |
| 2017/0008862 | A1 | 1/2017 | Sanuki et al. | |

FOREIGN PATENT DOCUMENTS

| | | | | |
|---|---|---|---|---|
| JP | 2016-190818 | A | 11/2016 | |
| JP | 2016190818 | A * | 11/2016 | C07D 277/82 |
| WO | 2012/147904 | A1 | 11/2012 | |
| WO | WO-2012147904 | A1 * | 11/2012 | G02B 5/3016 |
| WO | 2013/046781 | A1 | 4/2013 | |
| WO | 2014/010325 | A1 | 1/2014 | |
| WO | 2014/057884 | A1 | 4/2014 | |
| WO | WO 2015/025793 | A1 * | 2/2015 | C08F 23/38 |
| WO | 2015/129654 | A1 | 9/2015 | |

OTHER PUBLICATIONS

JP-2016190818-A (Nov. 10, 2016); Sanuki, Kanako et al.; machine translation. (Year: 2016).*

Tang et al, "A New Method for N—N Bond Cleavage of N,N-Disubstituted Hydrazines to Secondary Amines and Direct Ortho Amination of Naphthol and Its Analogues", Journal of the American Chemical Society, 2008, vol. 130, pp. 5840-5841, (Supporting Information pp. 1-17), cited in ISR (19 pages).

Rosamilia et al, "Insight into the Hard-Soft Acid-Base Properties of Differently Substituted Phenylhydrazines in Reactions with Dimethyl Carbonate", Journal of Physical Chemistry B, 2008, vol. 112, pp. 14525-14529, (Supporting Information pp. S1-S7), cited in ISR (12 pages).

Ali et al, "Discovery of ectoparasiticidal hydrazonotrifluoromethanesulfonanilides", Bioorganic & Medicinal Chemistry Letters, 2010, vol. 20, pp. 649-652, cited in ISR (4 pages).

International Search Report dated Jun. 6, 2017, issued in counterpart International Application No. PCT/JP2017/010629 (4 pages).

* cited by examiner

*Primary Examiner* — Rip A Lee
(74) *Attorney, Agent, or Firm* — Westerman, Hattori, Daniels & Adrian, LLP

(57) ABSTRACT

The present invention provides a novel method for producing a 2-hydrazinobenzothiazole derivative. The present invention also provides a method for producing a compound by using the 2-hydrazinobenzothiazole derivative obtained by the production method, and a composition that contains the compound. The present invention also provides a polymerizable composition that is useful in producing film-shaped polymers and contains the compound obtained by the production method. The invention of the present application provides a method for producing a compound represented by general formula (I-C), the method including a step of reacting a compound represented by general formula (I-B) with a compound represented by general formula (I-A) in the presence of at least one compound selected from the group consisting of metal amides, metal hydrides, metal alkoxides, and organic alkali metals. A compound derived from the compound produced by the production method, and a composition that contains the compound are also provided.

8 Claims, No Drawings

METHOD FOR PRODUCING 2-HYDRAZINOBENZOTHIAZOLE DERIVATIVE

TECHNICAL FIELD

The present invention relates to a method for producing a 2-hydrazinobenzothiazole derivative, a method for producing a compound by using the 2-hydrazinobenzothiazole derivative, a polymerizable composition and a polymerizable liquid crystal composition containing the compound, and an optically anisotropic body that uses the polymerizable liquid crystal composition.

BACKGROUND ART

In order to improve the viewing angle of liquid crystal displays, it is required to decrease or reverse the wavelength dispersibility of the birefringence of a retardation film. Various compounds having reverse wavelength dispersibility or low wavelength dispersibility have been developed to serve as the materials therefor. An example of such a compound known heretofore is a compound that has a hydrazone moiety in which a substituent, such as an alkyl group, is introduced into a nitrogen atom, and a benzothiazole moiety. An example of the key intermediate for producing this compound is a 2-hydrazinobenzothiazole derivative having a substituent, such as an alkyl group, on a nitrogen atom. In the production of the key intermediate, there has been used a method that involves reacting 2-hydrazinobenzothiazole with a halogenated alkyl etc., in the presence of potassium carbonate, cesium carbonate, or lithium bis(trimethylsilyl)amide (PTL 1 to PTL 3). However, according to this existing method, the isolated yield of the target substance has not always been satisfactory.

CITATION LIST

Patent Literature

PTL 1: International Publication No. WO 2014/010325 A1
PTL 2: International Publication No. WO 2013/046781 A1
PTL 3: International Publication No. WO 2012/147904 A1

SUMMARY OF INVENTION

Technical Problem

The existing method for producing a 2-hydrazinobenzothiazole derivative also has a problem in that, not only the isolated yield is low, but also the target compound obtained is likely to have a color derived from anions of 2-hydrazinobenzothiazole.

The present invention provides a method for producing a 2-hydrazinobenzothiazole derivative that can resolve the problem described above. The present invention also provides a method for producing a compound by using the 2-hydrazinobenzothiazole derivative obtained by this method, and a composition that contains the compound. The present invention also provides a polymerizable composition that contains a compound obtained by the method and that is useful in producing a film-shaped polymer that rarely undergoes a change in color or degradation of orientation under long-term UV irradiation.

Solution to Problem

The inventors of the present invention addressing the problem described above have conducted extensive research and have developed a novel method for producing a 2-hydrazinobenzothiazole derivative. That is, the invention of the present application provides a method for producing a compound represented by general formula (I-C), the method including a step of reacting a compound represented by general formula (I-B) with a compound represented by general formula (I-A) in the presence of at least one compound selected from the group consisting of metal amides, metal hydrides, metal alkoxides, and organic alkali metals. The present invention also provides a method for producing a compound by using the compound represented by general formula (I-C) as a precursor; a polymerizable composition containing the compound; a resin, a resin additive, oil, a filter, an adhesive, a pressure-sensitive adhesive, an oil/fat, an ink, a pharmaceutical product, a cosmetic product, a detergent, a building material, a packaging material, a liquid crystal material, an organic EL material, an organic semiconductor material, an electronic material, a display device, an electronic device, a communication device, an automotive part, an airplane part, a mechanical part, an agrichemical, or food that uses the compound, and a product that uses any of the foregoing; a polymerizable liquid crystal compound that uses the compound; a polymer obtained by polymerizing the polymerizable liquid crystal composition; and an optically anisotropic body that uses the polymer.

Advantageous Effects of Invention

According to the production method of the invention of the present application, it becomes possible to produce 2-hydrazinobenzothiazole derivatives in high yield and with less coloration. Since the compound obtained by the production method of the invention of the present application has less coloration, the compound is particularly useful as a raw material for products that do not allow even the slightest coloration or changes in color. An optical material and the like that are prepared by using, as a raw material, the compound obtained by the production method of the invention of the present application rarely undergo coloration or changes in color, and high transparency is ensured. The optically anisotropic body obtained from the polymerizable liquid crystal composition that contains the compound produced by the production method of the invention of the present application rarely undergoes changes in color and degradation of orientation under long-term UV irradiation; thus, the compound produced by the production method of the invention of the present application is useful as optical materials for optical compensation films and the like.

DESCRIPTION OF EMBODIMENTS

The present invention provides a method for producing a 2-hydrazinobenzothiazole derivative; a method for producing a compound by using the 2-hydrazinobenzothiazole derivative; a polymerizable composition containing the compound; a resin, a resin additive, oil, a filter, an adhesive, a pressure-sensitive adhesive, an oil/fat, an ink, a pharmaceutical product, a cosmetic product, a detergent, a building material, a packaging material, a liquid crystal material, an organic EL material, an organic semiconductor material, an electronic material, a display device, an electronic device, a communication device, an automotive part, an airplane part, a mechanical part, an agrichemical, or food that uses the compound, and a product that uses any of the foregoing; a polymerizable liquid crystal compound that uses the compound; a polymer obtained by polymerizing the polymerizable liquid crystal composition; and an optically anisotropic body that uses the polymer.

In the step of reacting the compound represented by general formula (I-B) with the compound represented by general formula (I-A), metal amides are preferably selected from alkali metal amides and alkaline earth metal amides from the viewpoints of yield, reaction rate, availability, and handling ease, and are more preferably selected from lithium amide, sodium amide, magnesium amide, potassium amide, calcium amide, cesium amide, and lithium diisopropylamide. In particular, from the viewpoint of handling ease, the metal amides are preferably selected from lithium amide, sodium amide, and potassium amide. The metal hydrides are preferably selected from alkali metal hydrides and alkaline earth metal hydrides, and are more preferably selected from lithium hydride, sodium hydride, magnesium hydride, potassium hydride, calcium hydride, cesium hydride, lithium aluminum hydride, and lithium borohydride. In particular, from the viewpoint of handling ease, the metal hydrides are more preferably selected from lithium hydride, sodium hydride, and potassium hydride. The metal alkoxides are preferably selected from alkali metal alkoxides, alkaline earth metal alkoxides, metal methoxides, metal ethoxides, metal propoxides, metal isopropoxides, metal butoxides, and metal tert-butoxides, and are more preferably selected from lithium methoxide, sodium methoxide, magnesium methoxide, potassium methoxide, calcium methoxide, cesium methoxide, lithium ethoxide, sodium ethoxide, magnesium ethoxide, potassium ethoxide, calcium ethoxide, cesium ethoxide, lithium propoxide, sodium propoxide, magnesium propoxide, potassium propoxide, calcium propoxide, cesium propoxide, lithium isopropoxide, sodium isopropoxide, magnesium isopropoxide, potassium isopropoxide, calcium isopropoxide, cesium isopropoxide, lithium butoxide, sodium butoxide, magnesium butoxide, potassium butoxide, calcium butoxide, cesium butoxide, lithium tert-butoxide, sodium tert-butoxide, magnesium tert-butoxide, potassium tert-butoxide, calcium tert-butoxide, and cesium tert-butoxide. In particular, from the viewpoint of handling ease, the metal alkoxides are more preferably selected from lithium methoxide, sodium methoxide, potassium methoxide, lithium ethoxide, sodium ethoxide, potassium ethoxide, lithium tert-butoxide, sodium tert-butoxide, and potassium tert-butoxide. The organic alkali metals are preferably selected from alkyl alkali metals, aryl alkali metals, lithium tri-tert-butoxyaluminum hydride, lithium tri-sec-butylborohydride, lithium triethylborohydride, and lithium bis(fluorosulfonyl)imide, more preferably selected from alkyl lithium, aryl lithium, lithium tri-tert-butoxyaluminum hydride, lithium tri-sec-butylborohydride, lithium triethylborohydride, and lithium bis(fluorosulfonyl)imide, yet more preferably selected from C1-C8 alkyl lithium and C6-C12 aryl lithium, and still more preferably selected from methyl lithium, ethyl lithium, propyl lithium, butyl lithium, sec-butyl lithium, tert-butyl lithium, pentyl lithium, hexyl lithium, and phenyl lithium. In particular, from the viewpoint of handling ease, the organic alkali metals are particularly preferably selected from methyl lithium, butyl lithium, sec-butyl lithium, tert-butyl lithium, and phenyl lithium. The organic alkali metal is preferably one in which an organic group solely composed of C, O, N, and H as the constituent atoms is bonded to an alkali metal. From the viewpoint of yield, a compound having a carbon-alkali metal bond is preferable.

In general formula (I-A), $W^2$ represents a linear or branched alkyl group having 1 to 20 carbon atoms, in which any hydrogen atom in the group may be substituted with a fluorine atom, and one —$CH_2$— or two or more non-adjacent —$CH_2$— may each independently be substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—. Alternatively, $W^2$ represents a group represented by $P^W$—$(Sp^W\text{-}X^W)_{kW}$—. From the viewpoints of availability of the raw material and ease of synthesis, $W^2$ preferably represents a linear or branched alkyl group having 1 to 20 carbon atoms, in which any hydrogen atom in the group may be substituted with a fluorine atom, and one —$CH_2$— or two or more non-adjacent —$CH_2$— may each independently be substituted with —O—, —S—, —CO—, —COO—, —OCO—, —CH═CH—COO—, —OCO—CH═CH—, —CH═CH—, —CF═CF—, or —C≡C—, or a group represented by $P^W$—$(Sp^W\text{-}X^W)_{kW}$—. More preferably, $W^2$ represents a linear or branched alkyl group having 1 to 20 carbon atoms, in which any hydrogen atom in the group may be substituted with a fluorine atom, and one —$CH_2$— or two or more non-adjacent —$CH_2$— may each independently be substituted with —O—, —CO—, —COO—, or —OCO—, or a group represented by $P^W$—$(Sp^W\text{-}X^W)_{kW}$—. Yet more preferably, $W^2$ represents a linear alkyl group having 1 to 12 carbon atoms, in which any hydrogen atom in the group may be substituted with a fluorine atom, and one —$CH_2$— or two or more non-adjacent —$CH_2$— may each independently be substituted with —O—, Still more preferably, $W^2$ preferably represents a linear alkyl group having 1 to 12 carbon atoms, in which one —$CH_2$— or two or more non-adjacent each —$CH_2$— may each independently be substituted with —O—, More specifically, a compound represented by general formula (I-A), in which the group represented by W is selected from following formulae (W2-a-1) (W2-a-6), is preferable:

[Chem. 1]

$$H\text{—}(CH_2)_{k2a}\text{—} \quad \text{(W2-a-1)}$$

$$H\text{—}(CH_2CH_2O)_{k2b}\text{—}CH_2\text{—} \quad \text{(W2-a-2)}$$

$$H\text{—}(CH_2CH_2O)_{k2b}\text{—}CH_2CH_2\text{—} \quad \text{(W2-a-3)}$$

$$HO\text{—}(CH_2)_{k2c}\text{—} \quad \text{(W2-a-4)}$$

$$HO\text{—}(CH_2CH_2O)_{k2d}\text{—}CH_2\text{—} \quad \text{(W2-a-5)}$$

$$HO\text{—}(CH_2CH_2O)_{k2d}\text{—}CH_2CH_2\text{—} \quad \text{(W2-a-6)}$$

(In the formulae, k2a represents an integer of 2 to 20, k2b represents an integer of 1 to 6, k2c represents an integer of 3 to 20, and k2d represents an integer of 1 to 6.) From the viewpoints of liquid crystallinity, reverse wavelength dispersibility, and solubility in solvents, k2a in formula (W2-a-1) more preferably represents an integer of 4 to 12, yet more preferably represents an integer of 4 to 8, and particularly preferably represents 6. In formula (W2-a-2) k2b more preferably represents an integer of 1 to 4, yet more preferably represents an integer of 1 to 3, and particularly preferably represents 2. In formula (W2-a-3), k2b more preferably represents an integer of 1 to 4, yet more preferably represents an integer of 1 to 3, and particularly preferably represents 1 or 2. In formula W2-a-4), k2c more preferably represents an integer of 3 to 12, yet more preferably represents an integer of 3 to 8, yet more preferably represents an integer of 3 to 8, and particularly preferably represents an integer of 4 to 6. In formulae (W2-a-5) and (W2-a-6), k2d more preferably represents an integer of 1 to 4, yet more preferably represents an integer of 1 to 3, and particularly preferably represents 2. Among formulae (W2-a-1) to (W2-a-6), the group represented by formula (W2-a-1), formula (W2-a-3), formula (W2-a-4), or formula (W2-a-6) is more preferable.

When W2 represents the group represented by $P^W$—($Sp^W$-$X^W$)$_{kW}$—, $P^W$ represents a polymerizable group, preferably represents a group polymerizable by radical polymerization, radical addition polymerization, cation polymerization, or anion polymerization, and preferably represents the same polymerizable group as $P^1$ described below. $Sp^W$ represents a spacer group and preferably represents the same group as $Sp^1$ described below. When there are more than one $Sp^W$, they may be the same or different. $X^W$ represents —O—, —S—, —OCH—, —$CH_2$O—, —CO—, —COO—, —OCO—, —CO—S—, —S—CO—, —O—CO—O—, —CO—NH—, —NH—CO—, —$SCH_2$—, —$CH_2$S—, —$CF_2$—, —$OCF_2$—, —$CF_2$S—, —$SCF_2$—CH═CH—COO—, —CH═CH—OCO—, —COO—CH═CH—, —OCO—CH═CH—, —COO—$CH_2$CH—, —OCO—$CH_2CH_2$—, —$CH_2$CH—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—N═CH—, —CF═CF—, —C≡C—, or a single bond. When there are more than one $X^W$, they may be the same or different. From the viewpoints of availability of raw materials and ease of synthesis, when there are more than one $X^W$, they may be the same or different and preferably each independently represent —O—, —S—, —$OCH_2$—, —$CH_2$O—, —COO—, —OCO—, —CO—S—, —S—CO—, —O—CO—O—, —CO—NH—, —NH—CO—, —COO—$CH_2CH_2$—, —OCO—$CH_2$CH—, —$CH_2CH_2$—COO—, —$CH_2CH_2$—OCO—, or a single bond. When there are more than one $X^W$, they may be the same or different and more preferably each independently represent —O—, —$OCH_2$—, —$CH_2$O—, —COO—, —OCO—, —COO—$CH_2CH_2$—, —OCO—$CH_2CH_2$—, —$CH_2CH_2$—COO—, —$CH_2CH_2$—OCO—, or a single bond. When there are more than one $X^W$, they may be the same or different and particularly preferably each independently represent —O—, —COO—, —OCO—, or a single bond. kW represents an integer of 0 to 10. From the viewpoints of solubility in solvent and liquid crystallinity in the case the compound is added to a liquid crystal composition, kW preferably represents an integer of 0 to 5, more preferably represents an integer of 1 to 3, and particularly preferably represents 1.

When $W^2$ represents a group represented by $P^W$—($Sp^W$-$X^W$)$_{kW}$—, $W^2$ preferably represents a group selected from groups represented by formula (P3-1), formula (P3-2), and formula (P3-3) below:

[Chem. 2]

$$P^3\text{—}(CH_2)_{k3a}\text{—} \quad (P3\text{-}1)$$

-continued

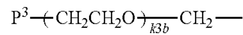

(P3-2)

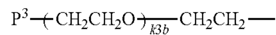

(P3-3)

(In the formulae, $P^3$ represents a polymerizable group, preferably represents a group polymerizable by radical polymerization, radical addition polymerization, cation polymerization, or anion polymerization and preferably represents the same polymerizable group as $P^1$ below, k3a represents an integer of 2 to 20, and k3b represents an integer of 1 to 6.) In formula (P3-1), from the viewpoint of liquid crystallinity, k3a more preferably represents an integer of 2 to 12 and yet more preferably represents an integer of 2 to 8. In formulae (P3-2) and (P3-3), from the viewpoint of liquid crystallinity, k3b more preferably represents an integer of 1 to 3 and yet more preferably represents an integer of 1 or 2.

In general formula (I-A), $LG^2$ represents a leaving group. Here, $LG^2$ may be any group that is eliminated as a result of the reaction between the compound represented by general formula (I-B) and the compound represented by general formula (I-A). However, from the viewpoints of ease of synthesis, availability of raw materials, and reactivity, LG preferably represents a group selected from a fluorine atom, a chlorine atom, a bromine atom, an iodine atom, a carbonyloxy group, an alkoxy group, a sulfonyloxy group, and a diazonium group, and more preferably represents a group selected from a fluorine atom, a chlorine atom, a bromine atom, an iodine atom, an alkylcarbonyloxy group, an arylcarbonyloxy group, an alkoxy group, an aryloxy group, an alkylsulfonyloxy group, an arylsulfonyloxy group, an alkyldiazonium group, and an aryldiazonium group. From the viewpoints of yield and reaction rate, $LG^2$ preferably represents a group selected from a chlorine atom, a bromine atom, an iodine atom, an alkylcarbonyloxy group, an arylcarbonyloxy group, an alkylsulfonyloxy group, and an arylsulfonyloxy group, and more preferably represents a group selected from a chlorine atom, a bromine atom, an iodine atom, an alkylsulfonyloxy group, and an arylsulfonyloxy group. More specifically, $LG^2$ more preferably represents a group selected from a chlorine atom, a bromine atom, an iodine atom, a p-toluenesulfonyloxy group, a methanesulfonyloxy group, and a trifluoromethanesulfonyloxy group, and, from the viewpoint of cost, $LG^2$ particularly preferably represents a group selected from a chlorine atom, a bromine atom, an iodine atom, a p-toluenesulfonyloxy group, and a methanesulfonyloxy group.

In general formula (I-B), $L^{W1}$ represents a fluorine atom, a chlorine atom, a bromine atom, an iodine atom, a pentafluorosulfuranyl group, a nitro group, a cyano group, a dimethylamino group, a diethylamino group, a diisopropylamino group, or a linear or branched alkyl group having 1 to 20 carbon atoms, in which any hydrogen atom in the group may be substituted with a fluorine atom, and one —$CH_2$— or two or more non-adjacent —$CH_2$— may each independently be substituted with —O—, —S—, —CH═CH—, —CF═CF—, or —C≡C—. From the viewpoints of ease of synthesis and availability of raw materials, $L^{W1}$ preferably represents a fluorine atom, a chlorine atom, a nitro group, a cyano group, a dimethylamino group, or a linear alkyl group having 1 to 12 carbon atoms, in which one —$CH_2$— or two or more non-adjacent —$CH_2$— may each independently be substituted with —O— or —S—, and more preferably represents a fluorine atom, a chlorine atom, a nitro group, a cyano group, a dimethylamino group, a methyl group, or a methoxy group.

In general formula (I-B), r represents an integer of 0 to 4. From the viewpoints of ease of synthesis and availability of raw materials, r preferably represents an integer of 0 to 2, more preferably represents 0 or 1, and particularly preferably represents 0.

From the viewpoints of scarcity of by-products and ease of purification, 0.01 to 100 molar equivalent, more preferably 0.1 to 10 molar equivalent, yet more preferably 0.5 to 3 molar equivalent, and particularly preferably 0.8 to 1.5 molar equivalent of the compound represented by general formula (I-A) is preferably used relative to the compound represented by general formula (I-B). Furthermore, 0.01 to 100 molar equivalent, more preferably 0.1 to 10 molar equivalent, yet more preferably 0.5 to 3 molar equivalent, and particularly preferably 0.8 to 1.5 molar equivalent of a base is preferably used relative to the compound represented by general formula (I-B).

The order of adding the compounds when the reactivity between the compound represented by general formula (I-A) and the base is high is preferably that, after the compound represented by general formula (I-B) is mixed with a base, the compound represented by general formula (I-A) is added. In this case, the base may be added to the compound represented by general formula (I-B), or the compound represented by general formula (I-B) may be added to the base. In contrast, when the reactivity between the compound represented by general formula (I-A) and the base is low, there is no limitation on the order of adding the compounds.

The reaction temperature is preferably −100° C. to 200° C., and, from the viewpoints of yield and reaction rate, is more preferably −5° C. to 150° C., yet more preferably −20° C. to 120° C., and still more preferably 0° C. to 100° C.

The reaction solvent may be one or a mixture of an organic solvent, water, an ionic liquid, and a super critical fluid, or a two-phase system, or the reaction may be solventless. From the viewpoint of yield, the reaction solvent preferably has low reactivity with metal amides, metal hydrides, metal alkoxides, or organic alkali metals. Examples of the organic solvent include ethers, aliphatic hydrocarbons, halogenated hydrocarbons, aromatic hydrocarbons, alcohols, and esters. More specific examples include chloroform, carbon tetrachloride, dichloromethane, 1,2-dichloroethane, acetone, acetonitrile, N,N-dimethylformamide, N,N-dimethylacetamide, dimethyl sulfoxide, diethyl ether, ethylene glycol monoethyl ether, diethylene glycol diethyl ether, xylene, ethyl acetate, butyl acetate, propyl acetate, cyclohexanone, 1,4-dioxane, dichloromethane, tetrahydrofuran, 1,2-dimethoxyethane, pyridine, 1-methyl-2-pyrrolidinone, toluene, hexane, pentane, cyclohexane, cyclopentane, heptane, benzene, methyl isobutyl ketone, tert-butyl methyl ether, and methyl ethyl ketone.

When the reaction is carried out in a two-phase system involving an organic solvent and water, it is possible to add a phase transfer catalyst. Examples of the phase transfer catalyst include benzalkonium chloride, benzyltrimethylammonium bromide, polyoxyethylene (10) octylphenyl ether [Triton X-100], polyoxyethylene(20) sorbitan monolaurate [Tween 20], polyoxyethylene (20) sorbitan monopalmitate [Tween 40], polyoxyethylene(20) sorbitan monostearate [Tween 60], polyoxyethylene(23) lauryl ether [Brij 35], and sorbitan monopalmitate [Span 40].

The amount of the reaction solvent may be any amount enough to take away heat of reaction; however, if the amount of the solvent is excessively small, the heat of reaction accumulates in the reaction system, and by-products are likely to be generated. Meanwhile, if the amount of the solvent is excessively large, the concentrations of the reactants are decreased, and the reaction rate is significantly decreased. From the above-described viewpoints, the amount of the solvent is preferably 0.01 mL to s L relative to 1 gram of the compound represented by general formula (I-B), more preferably 0.1 mL to 100 mL relative to 1 gram of the compound represented by general formula (I-B), yet more preferably 1 mL to 20 mL relative to 1 gram of the compound represented by general formula (I-B), and particularly preferably 2 mL to 10 mL relative to 1 gram of the compound represented by general formula (I-B).

According to the production method of the invention of the present application, the yield of the compound represented by general formula (I-C) relative to the amount of the compound represented by general formula (I-B), which is the raw material, can be 70% or more, 80% or more, or 90% or more. Since the extent of coloration of the reaction solution after the reaction is presumably derived from the by-products of the reaction between the compound represented by general formula (I-B) and the compound represented by general formula (I-A), the yield of the product can be increased, and the coloration of the reaction solution can be suppressed by the present invention. According to the production method of the present invention, since the step of purifying the product can be simplified or omitted, the productivity of the production process can be improved.

The compound derived from the compound represented by general formula (I-C) is preferably a compound represented by general formula (I). In general formula (I), $R^1$ represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms in which any hydrogen atom in the group may be substituted with a fluorine atom and one —$CH_2$— or two or more non-adjacent —$CH_2$— may each independently be substituted with —O—, —S—, —$OCH_2$, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2$—COO—, —$CH_2CH_2$—OCO—, —COO—$CH_2$—, —OCO—$CH_2$—, —CH—COO—, —$CH_2$—OCO—, —CH═CH—, —N═N—, —CH═N—N═CH—, —CF═CF—, or —C≡C—, or $R^1$ represents a group represented by $P^1$—$(Sp^1\text{-}X^1)_{k1}$—. When $R^1$ represents a group other than the group represented by $P^1$—$(Sp^1\text{-}X^1)_{k1}$—, from the viewpoints of liquid crystallinity and ease of synthesis, $R^1$ more preferably represents a hydrogen atom, a fluorine atom, a chlorine atom, or a linear or branched alkyl group having 1 to 12 carbon atoms, in which one —$CH_2$— or two or more non-adjacent —$CH_2$— may each independently be substituted with —O—, —COO—, —OCO—, or —O—CO—O—, more preferably represents a hydrogen atom, a fluorine atom, a chlorine atom, or a linear alkyl group or linear alkoxy group having 1 to 12 carbon atoms, and yet more preferably represents a linear alkyl group or linear alkoxy group having 1 to 12 carbon atoms.

When $R^1$ represents a group represented by $P^1$—$(Sp^1\text{-}X^1)_{k1}$—, $P^1$ present in $R^1$ represents a polymerizable group, preferably represents a group polymerizable by radical polymerization, radical addition polymerization, cation polymerization, or anion polymerization, and yet more preferably represents a group selected from formula (P-1) to formula (P-20) below:

[Chem. 3]

(P-1)

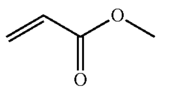

(P-2)

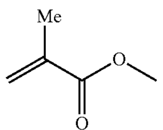

(P-3)

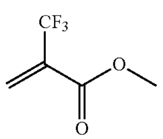

(P-4)

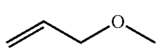

(P-5)

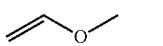

(P-6)

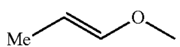

(P-7)

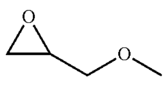

(P-8)

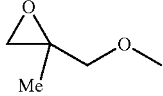

(P-9)

(P-10)

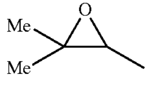

(P-11)

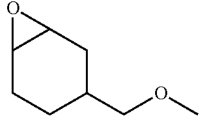

(P-12)

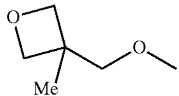

(P-13)

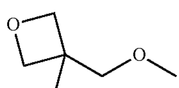

(P-14)

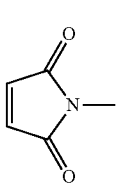

-continued (P-15)

(P-16)

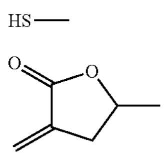

(P-17)

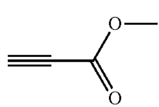

(P-18)

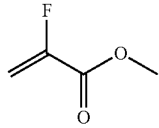

(P-19)

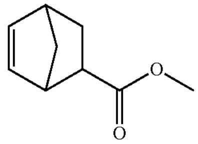

(P-20)

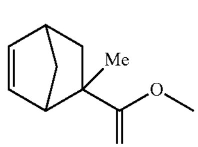

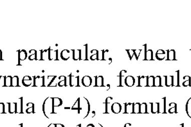

In particular, when the polymerization method is UV polymerization, formula (P-1), formula (P-2), formula (P-3), formula (P-4), formula (P-5), formula (P-7), formula (P-11), formula (P-13), formula (P-15), or formula (P-18) is preferable, formula (P-1), formula (P-2), formula (P-3), formula (P-7), formula (P-11), or formula (P-13) is more preferable, formula (P-1), formula (P-2), or formula (P-3) is yet more preferable, and formula (P-1) or formula (P-2) is particularly preferable.

$Sp^1$ present in $R^1$ represents a spacer group, and when there are more than one $Sp^1$, they may be the same or different. The spacer group preferably represents an alkylene group having 1 to 20 carbon atoms, in which one —$CH_2$— or two or more non-adjacent —$CH_2$— may each independently be substituted with —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2$—O—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—CH—, —OCO—$CH_2$—, —$CH_2$—COO—, —$CH_2$—OCO—, —CH═CH—, —N═N—, —CH═N—N═CH—, —CF═CF—, —C≡C—. From the viewpoints of availability of raw materials and ease of synthesis, when there are more than one $Sp^1$, they may be the same or different, and preferably each independently represent an alkylene group having 1 to 20 carbon atoms, in which one —$CH_2$— or two or more non-adjacent —$CH_2$— may each independently be substituted with —O—, —COO—, —OCO—, —OCO—O—, —CO—NH—, —NH—CO—, —CH═CH—, or —C≡C—. When there are more than one $Sp^1$, they may be the same or different, and more preferably each independently represent an alkylene group having 1 to 10 carbon atoms, in which one —$CH_2$— or two or more non-adjacent —$CH_2$— may each independently be substituted with —O—, —COO—, or —OCO—. When there are more than one $Sp^1$, they may be the same or different, and yet more preferably each independently represent an alkylene group having 1 to 10 carbon atoms. When there are more than one $Sp^1$, they may be the same or different, and particularly preferably each independently represent an alkylene group having 2 to 8 carbon atoms.

$X^1$ present in $R^1$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —CH—OCO—, —CH═CH—, —N═N—, —CH═N—N═CH—, —CF═CF—, —C≡C—, or a single bond, and when there are more than one $X^1$, they may be the same or different. From the viewpoints of availability of raw materials and ease of synthesis, when there are more than one X, they may be the same or different and preferably each independently represent —O—, —S—, —$OCH_2$—, —$CH_2O$—, —COO—, —OCO—, —CO—S—, —S—CO—, —O—CO—O—, —CO—NH—, —NH—CO—, —COO—$CH_2H_2$—, —OCO—$CH_2CH_2$—, —$CH_2CH_2$—COO—, —$CH_2CH_2$—OCO—, or a single bond. When there are more than one $X^1$, they may be the same or different and more preferably each independently represent —O—, —$OCH_2$—, —$CH_2O$—, —CO—, —OCO—, —COO—$CH_2CH_2$—, —OCO—$CH_2CH_2$—, —$CH_2CH_2$—CO—, —$CH_2CH_2$—OCO—, or a single bond. When there are more than one $X^1$, they may be the same or different and particularly preferably each independently represent —O—, —COO—, —OCO—, or a single bond.

In $R^1$, k1 represents an integer of 0 to 10. From the viewpoints of solubility in solvents and liquid crystallinity in the case the compound is added to a liquid crystal composition, k1 preferably represents an integer of 0 to 5, more preferably an integer of 1 to 3, and particularly preferably 1.

In general formula (i), $R^2$ represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms in which any hydrogen atom in the group may be substituted with a fluorine atom and one —$CH_2$— or two or more non-adjacent —$CH_2$— may each independently be substituted with —O—, —S—, —$OCH_2$—, —$CH_2O$—, —CO—, —COO—, —OCO—, —CO—S—, —S—CO—, —O—CO—, —NH—, —NH—CO—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2$—$CH_2$—OCO—, —COO—$CH_2$—, —OCO—$CH_2$—, —$CH_2$—COO—, —$CH_2$—OCO—, —CH═CH—, —N═N—, —CH═N—N═CH—, —CF═CF—, or —C≡C—, or $R^2$ represents a group represented by —$(X^2—Sp^2)_{k2}$—$P^2$. When $R^1$ represents a group other than the group represented by $P^1$—$(Sp^1\text{-}X^1)_{k1}$—, the preferable structure for $R^2$ is the same as the preferable structure for $R^1$. Moreover, when R represents a group represented by —$(X^2—Sp^2)_{k2}$—$P^2$, the preferable structures for $P^2$, $Sp^2$, $X^2$, and k2 present in $R^2$ are respectively the same as the preferable structures for $P^1$, $Sp^1$, $X^1$, and k1.

In general formula (i), $A^1$ and $A^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or 1,3-dioxane-2,5-diyl group, which may be unsubstituted or substituted with one or more substituents L. When there are more than one $A^1$, they may be the same or different. When there are more than one $A^2$, they may be the same or different. From the viewpoints of liquid crystallinity, ease of synthesis, and availability of raw materials, when there are more than one $A^1$, they may be the same or different, and when there are more than one $A^2$, they may be the same or different. They preferably each independently represent a 1,4-phenylene group, a 1,4-cyclohexylene group, or a naphthalene-2,6-diyl group which may be unsubstituted or substituted with one or more substituents L. When there are more than one $A^1$ and/or $A^2$, they may be the same or different, and preferably each independently represent a group selected from formula (A-1) to formula (A-11) below:

[Chem. 4]

(A-1)

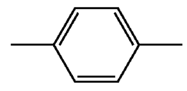

(A-2)

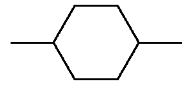

(A-3)

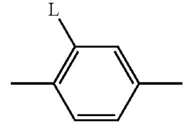

(A-4)

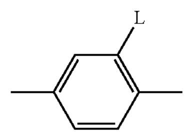

(A-5)

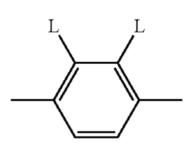

(A-6)

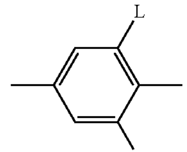

(A-7)

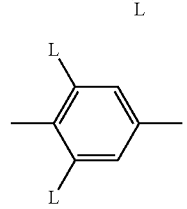

-continued (A-8)

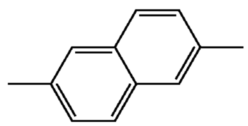

(A-9)

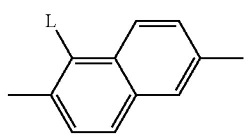

(A-10)

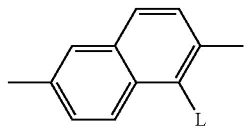

(A-11)

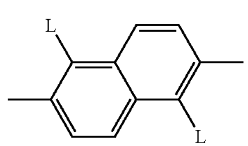

When there are more than one $A^1$ and/or $A^2$, they may be the same or different, and more preferably each independently represent a group selected from formula (A-1) to formula (A-8). When there are more than one $A^1$ and/or $A^2$, they may be the same or different, and yet more preferably each independently represent a group selected from formula (A-1) to formula (A-4). When there are more than one $A^1$ and/or $A^2$ they may be the same or different, and particularly preferably each independently represent formula (A-1) or (A-2).

In general formula (I), L each independently represent a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —$CH_2$— or two or more non-adjacent —$CH_2$— may each independently be substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—. In the alkyl group, any hydrogen atom may be substituted with a fluorine atom. Alternatively, L may represent a group represented by $P^L$—$(Sp^L$—$X^L)_{kL}$—, where $P^L$ represents a polymerizable group and preferably represents a group polymerizable by radical polymerization, radical addition polymerization, cation polymerization, or anion polymerization. $Sp^L$ represents a single bond or a linear alkylene group having 1 to 10 carbon atoms, in which one —CH— or two or more non-adjacent —$CH_2$— may each independently be substituted with —O—, —COO—, or —OCO—, When there are more than one $Sp^L$, they may be the same or different. $X^L$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—N═CH—, —CF═CF—, —C≡C—, or a single bond, and when there are more than one $X^L$, they may be the same or different (however, $P^L$—$(Sp^L$—$X^L)_{kL}$— does not have an —O—O— bond). kL represents an integer of 0 to 10, and when there are more than one kL in the compound, they may be the same or different. From the viewpoints of liquid crystallinity and ease of synthesis, when there are more than one L, they may be the same or different and preferably each independently represent a fluorine atom, a chlorine atom, a pentafluorosulfuranyl group, a nitro group, a methylamino group, a dimethylamino group, a diethylamino group, a diisopropylamino group, or a linear or branched alkyl group having 1 to 20 carbon atoms, in which any hydrogen atom may be substituted with a fluorine atom and one —$CH_2$— or two more non-adjacent —$CH_2$— may each independently be substituted with a group selected from —O—, —S—, —CO—, —COO—, —OCO—, —O—CO—O—, —CH═CH—, —CF═CF—, and —C≡C—. When there are more than one L, they may be the same or different, and more preferably each independently represent a fluorine atom, a chlorine atom, or a linear or branched alkyl group having 1 to 12 carbon atoms, in which any hydrogen atom may be substituted with a fluorine atom and one —$CH_2$— or two or more non-adjacent —$CH_2$— may each independently be substituted with a group selected from —O—, —COO—, and —OCO—, When there are more than one L, they may be the same or different, and yet more preferably each independently represent a fluorine atom, a chlorine atom, or a linear or branched alkyl group or alkoxy group having 1 to 12 carbon atoms, in which any hydrogen may be substituted with a fluorine atom. When there are more than one L, they may be the same or different, and particularly preferably each independently represent a fluorine atom, a chlorine atom, or a linear alkyl group or linear alkoxy group having 1 to 8 carbon atoms.

In general formula (I), $Z^1$ and $Z^2$ each independently represent —C—, —S—, —$OCH_2$—, —$CH_2$—, —$CH_2CH_2$—, —CO—, —COO—, —OCO—, —CO—S—, —S—CO—, —O—CO—O—, —CO—NH—, —NH—CO—, —OCO—NH—, —NH—COO—, —NH—CO—N—, —NH—O—, —O—NH—, —$SCH_2$—, —$CH_2S$—, —$CF_2$—, —$OCF_2$—, —$CF_2S$—, —$SCF_2$—, —CH═CH—COO—, —CH═CH—OCO—, —COO—CH═CH—, —OCO—CH═CH—, —COO—$CH_2C_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—, —N═CH—, —CH═N—N═CH—, —CF═CF—, —C═C—, or a single bond. When there are more than one $Z^1$, they may be the same or different. When there are more than one $Z^2$, they may be the same or different. From the viewpoint of liquid crystallinity, availability of raw materials, and ease of synthesis, when there are more than one Z or when there are more than one $Z^2$, they may be the same or different and preferably each independently represent —$OCH_2$—, —$CH_2O$—, —COO—, —OCO—, —$CF_2O$—, —$OCF_2$—, —$CH_2CH_2$—, —$CF_2CF_2$—, —CH═CH—COO—, —CH═CH—OCO—, —COO—CH═CH—, —OCO—CH═CH—, —COO—$CH_2C_2$—, —OCO—$CH_2CH_2$—, —$CH_2CH_2$—COO—, —$CH_2CH_2$—OCO—, —CH═CH—, —CF═CF—, —C≡C—, or a single bond. When there are more than one $Z^1$ and/or $Z^2$, they may be the same or different, and more preferably each independently represent —$OCH_2$—, —$CH_2O$—, —COO—, —OCO—, —$CF_2O$—, —$OCF_2$—, —$CH_2CH_2$—, or a single bond. When there are more than one $Z^1$ and/or $Z^2$, they may be the same or different, and particularly preferably each independently represent —$OCH_2$—, —$CH_2O$—, —COO—, —OCO—, or a single bond. $Z^1$ and $Z^2$ directly bonded to M each independently represent —$OCH_2$— or —$CH_2O$— and $Z^1$ and $Z^2$ not directly bonded to M preferably each independently represent —$OCH_2$—, —$CH_2O$—, —CCO—, —OCO—, or a single bond.

In general formula (I), m1 and m2 each independently represent an integer of 0 to 6, and m1+m2 is an integer of 0 to 6. From the viewpoints of solubility in solvents, liquid crystallinity, and changes in color and orientation under UV irradiation, m1 and m2 preferably each independently represent an integer of 1 to 3 and particularly preferably each independently represent 1 or 2.

In general formula (I), M represents a substituted or unsubstituted trivalent aromatic group. From the viewpoints of ease of synthesis and availability of raw materials, M preferably represents a group selected from formula (M-1) to formula (M-6) below:

[Chem. 5]

(M-1)

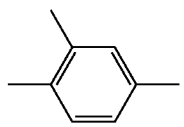

(M-2)

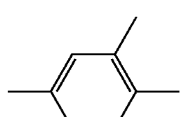

(M-3)

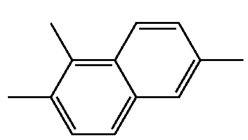

(M-4)

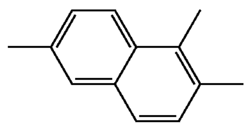

(M-5)

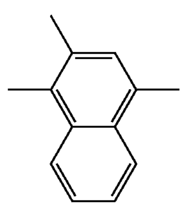

(M-6)

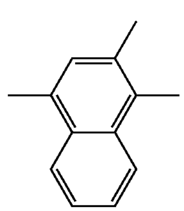

(In the formulae, the groups represented by $Z^1$ and $Z^2$ respectively bond to the bonds on the left-hand side and the right-hand side, the remaining group bonds to the bond on the upper side, and these groups may be unsubstituted or substituted with one or more substituents $L^M$, and any —CH= may each independently be substituted with —N=.) M more preferably represents a group selected from formula (M-1), formula (M-2), formula (M-5), and formula (M-6) which may be unsubstituted or substituted with one or more substituents $L^M$. M yet more preferably represents a group selected from formula (M-1) and formula (M-2) which may be unsubstituted or substituted with one or more substituents $L^M$, and particularly preferably represents a group selected from formula (M-1) and formula (M-2) which are unsubstituted.

In general formula (I), $L^M$ each independently represent a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —$CH_2$— or two or more non-adjacent —$CH_2$— may each independently be substituted with —O—, —S—, —CO—, —COO—, —CO—, —CO—S—, —S—CO—, —O—CO—O—, —CO—NH—, —NH—CO—, —CH=CH—COO—, —CH=CH—OCO—, —COO—CH=CH—, —OCO—; CH=CH—, —CH=CH—, —CF=CF—, or —C≡C—. In the alkyl group, any hydrogen atom may be substituted with a fluorine atom. Alternatively, $L^M$ may represent a group represented by $P^{LM}$—$(Sp^{LM}$—$X^{LM})_{kLM}$—, where $P^{LM}$ represents a polymerizable group and preferably represents a group polymerizable by radical polymerization, radical addition polymerization, cation polymerization, or anion polymerization. Sp represents a spacer group, and the preferable spacer groups are the same as those for $Sp^1$ described above. When there are more than one $Sp^{LM}$, they may be the same or different. $X^{LM}$ represents —O—, —S—, —$OCH_2$—, —$CH^2O$—, —CO—, —COO—, —OCO—, —CO—S—, —S—CO—, —O—CO—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond, and when there are more than one $X^{LM}$, they may be the same or different (however, $P^{LM}$—$(Sp^{LM}$—$X^{LM})_{kLM}$— does not contain an —O—O— bond), and kLM represents an integer of 0 to 10. When there are more than one $L^M$ in the compound, they may be the same or different. From the viewpoints of liquid crystallinity and ease of synthesis, when there are more than one $L^M$, they may be the same or different and may each independently represent a fluorine atom, a chlorine atom, a pentafluorosulfuranyl group, a nitro group, a cyano group, a methylamino group, a dimethylamino group, a diethylamino group, or a linear or branched alkyl group having 1 to 20 carbon atoms, in which any hydrogen atom may be substituted with a fluorine atom and one —$CH_2$— or two more non-adjacent —$CH_2$— may each independently be substituted with a group selected from —O—, —S—, —CO—, —COO—, —OCO—, —O—CO—O—, —CH=CH—, —CF=CF—, and —C≡C—. When there are more than one LP, they may be the same or different, and may each independently represent a fluorine atom, a chlorine atom, a nitro group, a cyano group, or a linear or branched alkyl group having 1 to 12 carbon atoms, in which any hydrogen atom may be substituted with a fluorine atom, and one —$CH_2$— or two or more non-adjacent —$CH_2$— may each independently be substituted with a group selected from —O—, —COO—, and —OCO—, When there are more than one $L^M$, they may be the same or different, and may each independently represent a fluorine atom, a chlorine atom, a nitro group, a cyano group, or a linear or branched alkyl group or alkoxy group having 1 to 12 carbon atoms, in which any hydrogen may be substituted with a fluorine atom. When there are more than one $L^M$, they may be the same or different and particularly preferably each independently represent a fluorine atom, a chlorine atom, a nitro group, a cyano group, a methyl group, or a methoxy group.

In general formula (I), Y represents a hydrogen atom, a fluorine atom, a chlorine atom, a bromine atom, an iodine atom, a pentafluorosulfuranyl group, a nitro group, a cyano, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which any hydrogen atom in the alkyl group may be substituted with a fluorine atom and one —$CH_2$— or two more non-adjacent —$CH_2$— may each independently be substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—. From the viewpoints of liquid crystallinity and ease of synthesis, Y more preferably represents a hydrogen atom or a linear or branched alkyl group having 1 to 12 carbon atoms, in which any hydrogen atom may be substituted with a fluorine atom and one —$CH_2$— or two more non-adjacent —$CH_2$— may each independently be substituted with —O—, —COO—, or —OCO—, Y more preferably represents a hydrogen atom or a linear alkyl group having 1 to 12 carbon atoms, and particularly preferably represents a hydrogen atom.

Note that the compound represented by general formula (I) does not contain an —O—O— bond.

The compound represented by general formula (I) may be a polymerizable compound or a non-polymerizable compound. For optical film raw material usage, the compound represented by general formula (I) is preferably a polymerizable compound. In such a case, a group represented by $P^1$ or $P^2$ is more preferably present in at least one of $R^1$ and $R^2$, and particularly preferably, a group represented by $P^1$ or $P^2$ is present in both $R^1$ and $R^2$.

Preferable specific examples of the compound represented by general formula (I) are those represented by general formula (I-ia), general formula (I-ib), and general formula (I-ii) below:

[Chem. 6]

(I-ia)

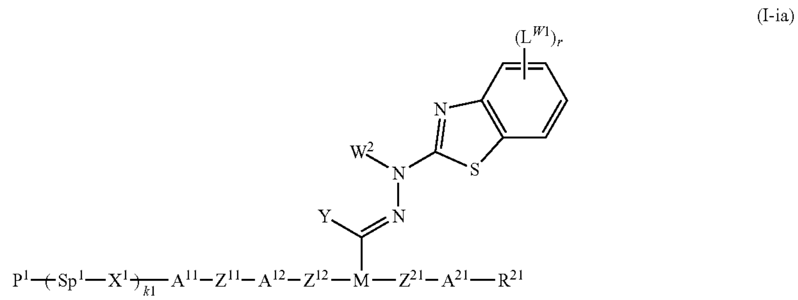

(I-ib)

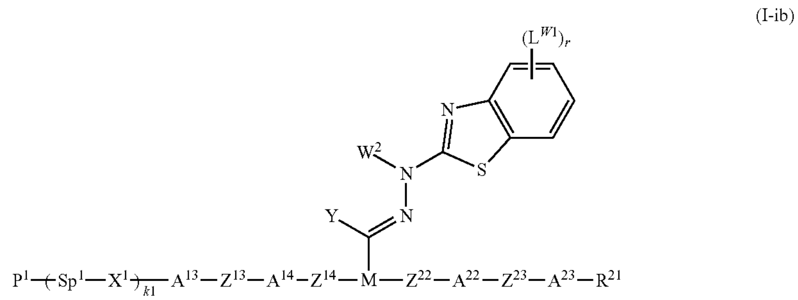

-continued (I-ii)

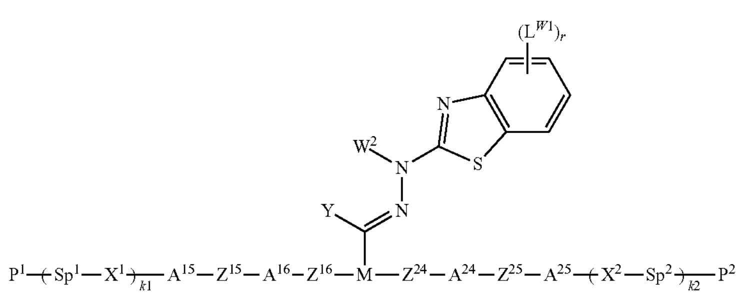

(In the formulae, $P^1$, $P^2$, $Sp^1$, $Sp^2$, $X^1$, $X^2$, k1, k2, M, Y, $W^2$, $L^{W1}$, and r are the same as those in general formula (I); $R^{21}$ represents a hydrogen atom, a fluorine atom, a chlorine atom, or a linear or branched alkyl group having 1 to 12 carbon atoms, in which one —$CH_2$— or two more non-adjacent —$CH_2$— may each independently be substituted with —O—, —COO—, —OCO—, or —O—CO—O—; $A^{11}$, $A^{21}$, $A^{13}$, $A^{22}$, $A^{23}$, $A^{15}$, and $A^{25}$ each independently represent a 1,4-phenylene group or a 1,4-cyclohexylene group, which may be unsubstituted or substituted with one or more substituents $L^1$; $A^{12}$, $A^{14}$, $A^{16}$, and $A^{24}$ each independently represent a 1,4-cyclohexylene group, which may be unsubstituted or substituted with one or more substituents $L^2$; $L^1$ and $L^2$ are each the same as L in general formula (I), when there are more than one $L^1$ in the compound, they may be the same or different, and when there are more than one $L^2$ in the compound, they may be the same or different; $Z^{11}$, $Z^{21}$, $Z^{13}$, $Z^{22}$, $Z^{23}$, $Z^{15}$, and $Z^{25}$ each independently represent —$OCH_2$—, —$CH_2O$—, —$CH_2CH_2$—, —COO—, —OCO—, —$CF_2O$—, —$OCF_2$—, or a single bond; and $Z^{12}$, $Z^{14}$, $Z^{16}$, and $Z^{24}$ each independently represent —$OCH_2$—, —$CH_2O$—, —$CH_2CH_2$—, —COO—, —OCO—, —$CF_2O$—, or —$OCF_2$—.

Preferable and more specific examples of the compound represented by general formula (I) are those represented by general formula (I-ia-i), general formula (I-ib-i), and general formula (I-ii-i) below:

[Chem. 7]

(I-ia-i)

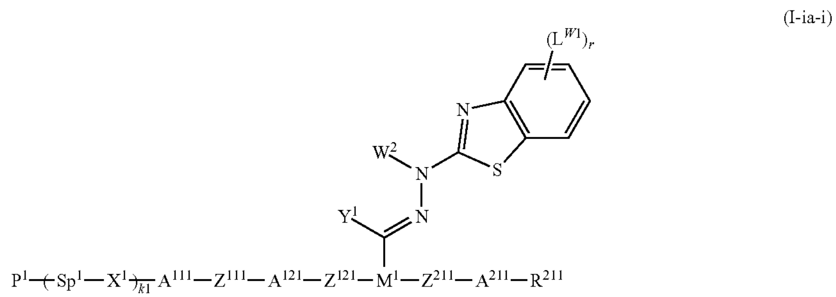

(I-ib-i)

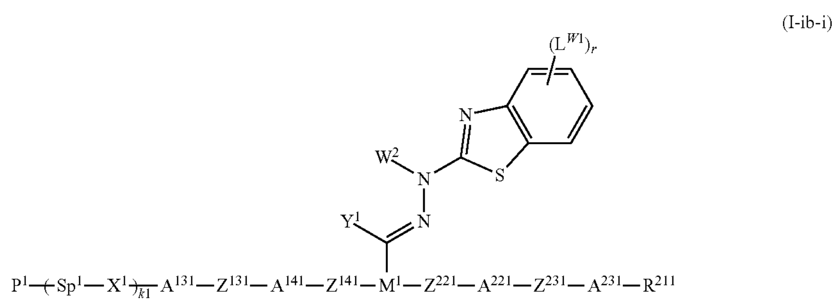

-continued (I-ii-i)

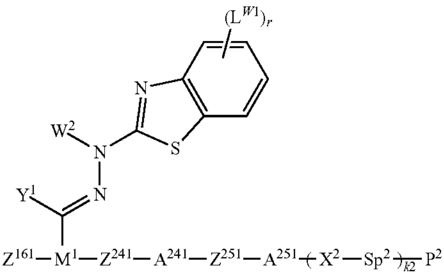

(In the formulae, $P^1$, $P^2$, $Sp^1$, $Sp^2$, $X^1$, $X^2$, k1, k2, $W^2$, $L^{W1}$, and r are the same as those in general formula (I); $R^{211}$ represents a linear alkyl group or linear alkoxy group having 1 to 12 carbon atoms; $A^{111}$, $A^{131}$, $A^{151}$, and $A^{251}$ each represent a 1,4-phenylene group, which may be unsubstituted or substituted with one or more substituents $L^{11}$; $A^{121}$, $A^{141}$, $A^{221}$, $A^{231}$, $A^{161}$, and $A^{241}$ each represent a 1,4-cyclohexylene group; $A^{211}$ represents a 1,4-phenylene group or a 1,4-cyclohexylene group, and the 1,4-phenylene group may be unsubstituted or substituted with one or more substituents $L^{11}$; $L^{11}$ represents a fluorine atom, a chlorine atom, or a linear or branched alkyl group having 1 to 20 carbon atoms, in which one —$CH_2$— or two more non-adjacent —$CH_2$— may each independently be substituted with —O—, —CO—, —COO—, or —OCO— and any hydrogen in the alkyl group may be substituted with a fluorine atom; when there are more than one $L^{11}$ in the compound, they may be the same or different; $Z^{111}$, $Z^{121}$, $Z^{131}$, $Z^{141}$, $Z^{151}$, $Z^{161}$, $Z^{241}$, and $Z^{251}$ each independently represent —$OCH_2$—, —$CH_2O$—, —COO—, or —OCO—; $Z^{211}$, $Z^{221}$, and $Z^{231}$ each independently represent a single bond; $M^1$ represents a group selected from formula (M-1-1) and formula (M-2-1) below:

[Chem. 8]

(M-1-1)

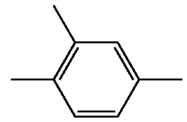

(M-2-1)

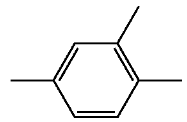

and $Y^1$ represents a hydrogen atom.)

Preferable examples of the compound represented by general formula (I) are those represented by general formula (I-ia-i-1) to formula (I-ii-i-2) below:

[Chem. 9]

(I-ia-i-1)

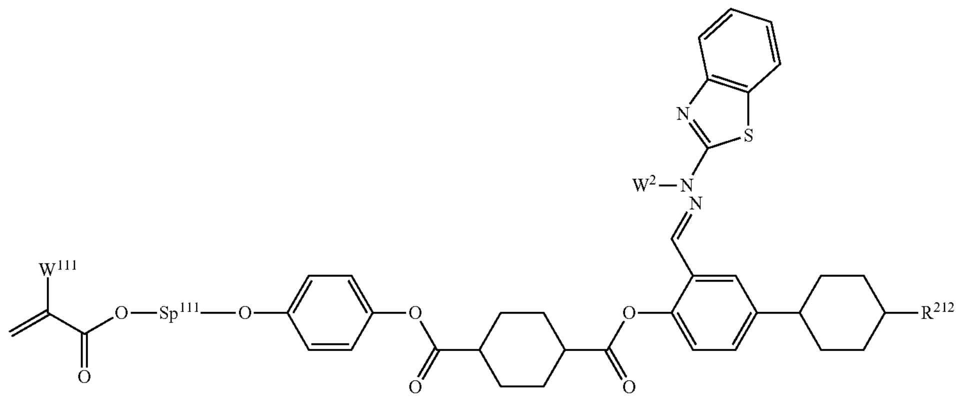

-continued
(I-ia-i-2)
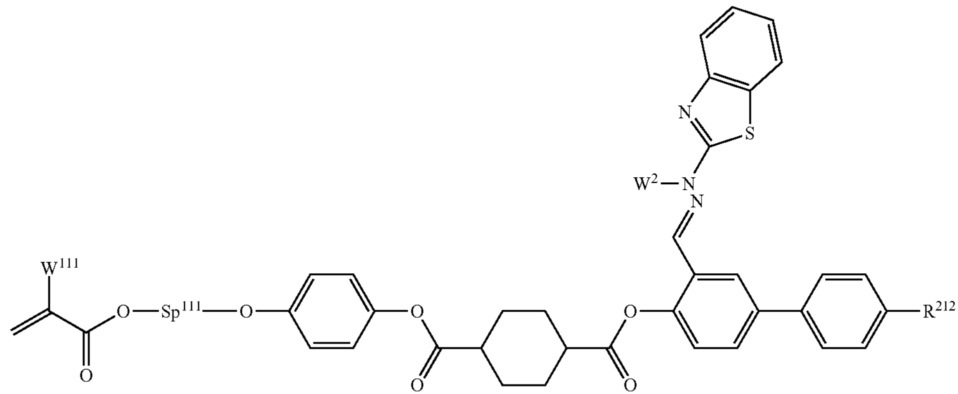
(I-ia-i-3)
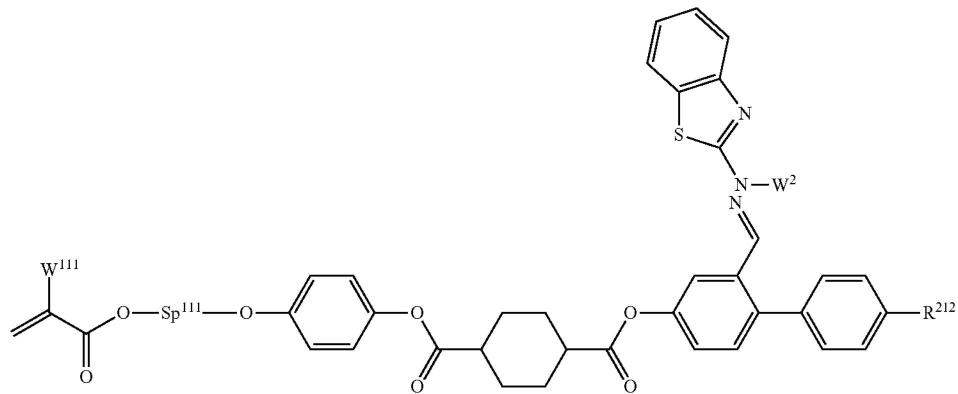
[Chem. 10]
(I-ia-i-4)
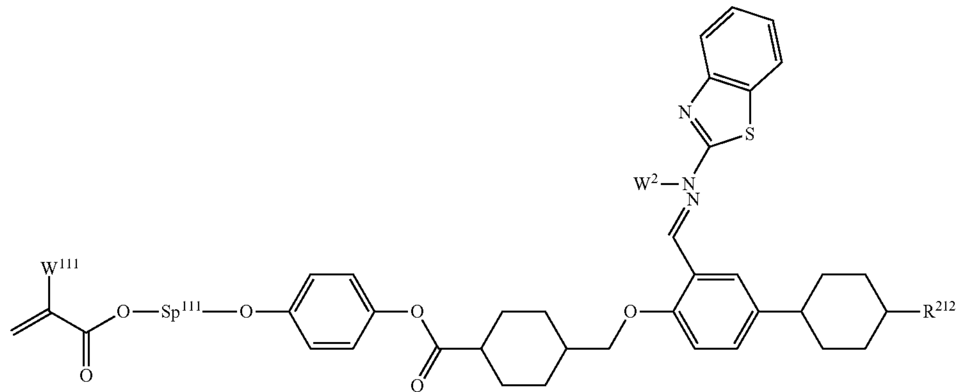
(I-ia-i-5)
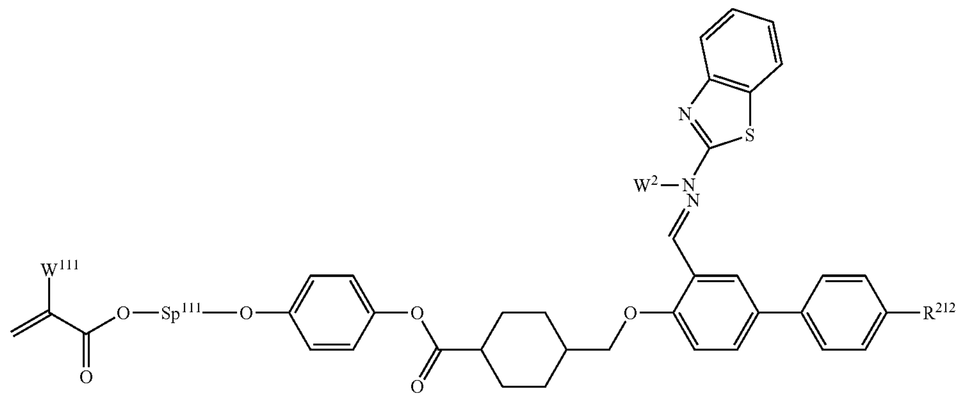

-continued
(I-ia-i-6)
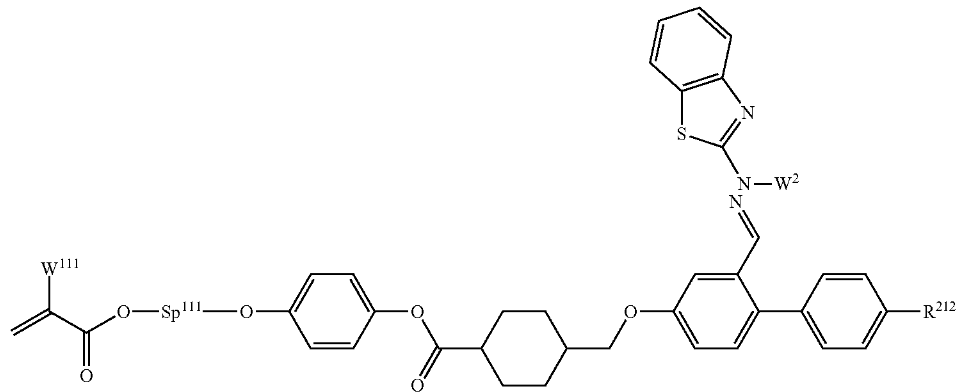
[Chem. 11]
(I-ib-i-1)
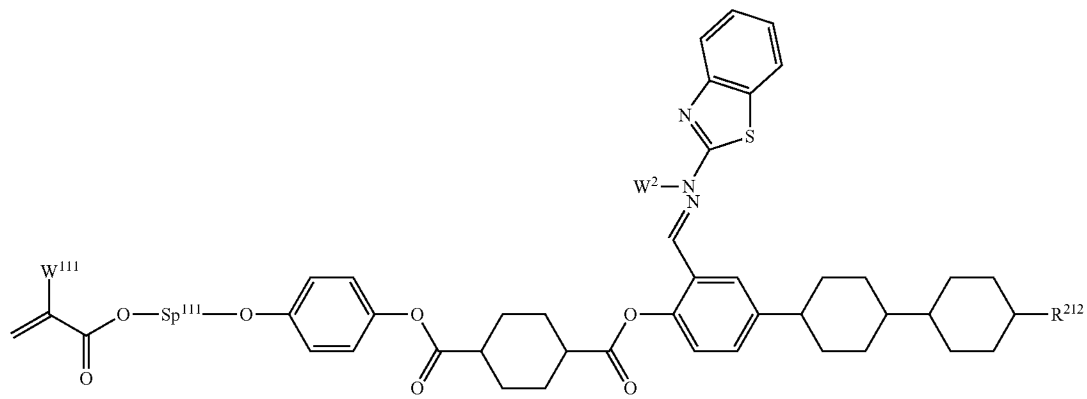
(I-ib-i-2)
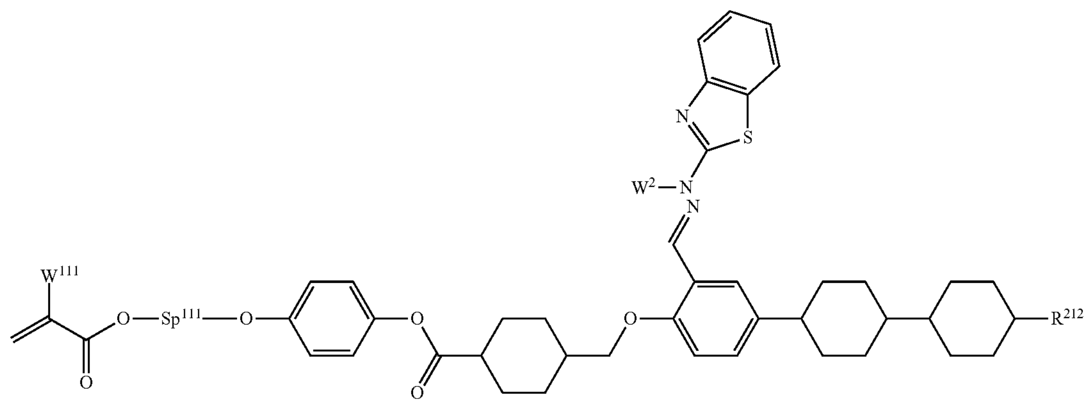

-continued

[Chem. 12]

(I-ii-i-1)

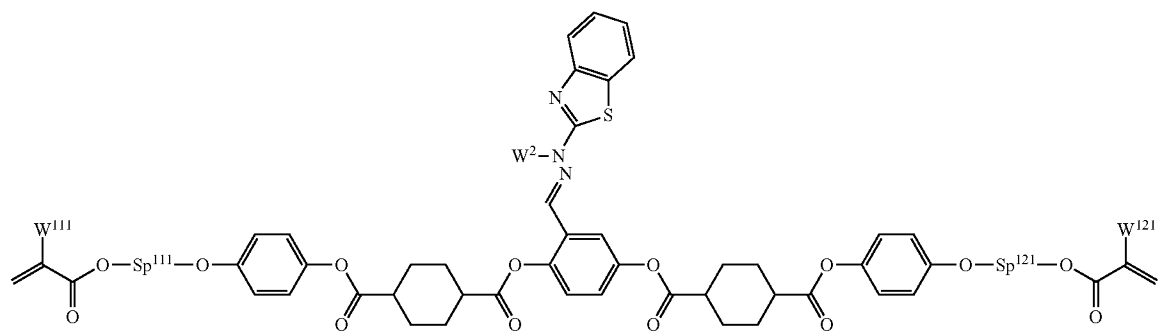

(I-ii-i-2)

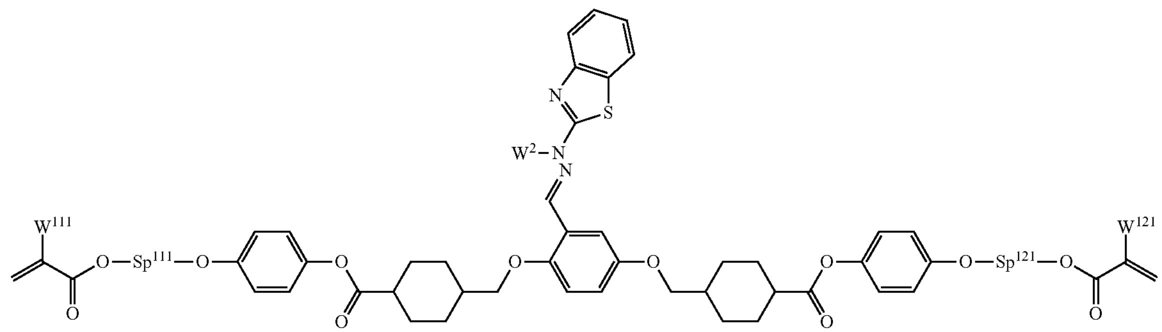

(In the formulae $W^{111}$ and $W^{121}$ each represent a hydrogen atom or a methyl group, $Sp^{111}$ and $Sp^{121}$ each represent an alkylene group having 2 to 8 carbon atoms, $R^{212}$ represents a linear alkyl group or linear alkoxy group having 1 to 8 carbon atoms, and $W^2$ is the same as that in general formula (I).

More preferable examples of the compound represented by general formula (I) are those represented by formula (I-ia-i-1-1) to formula (I-ii-i-2-2) below:

[Chem. 13]

(I-ia-i-1-1)

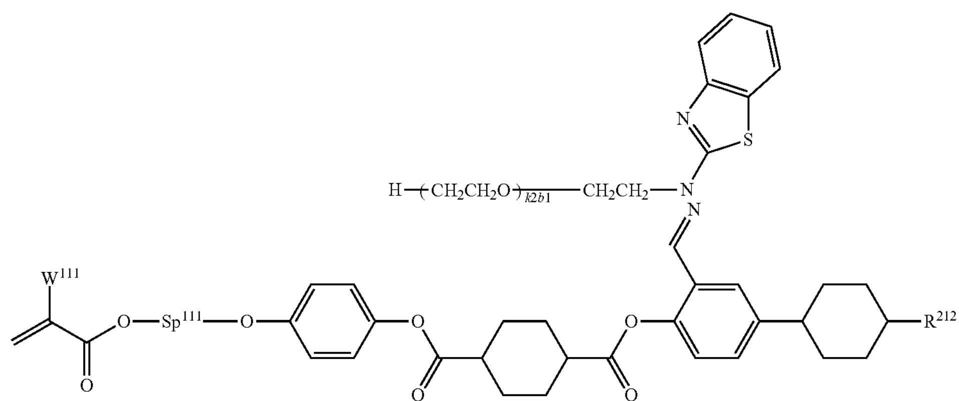

-continued
(I-ia-i-4-1)
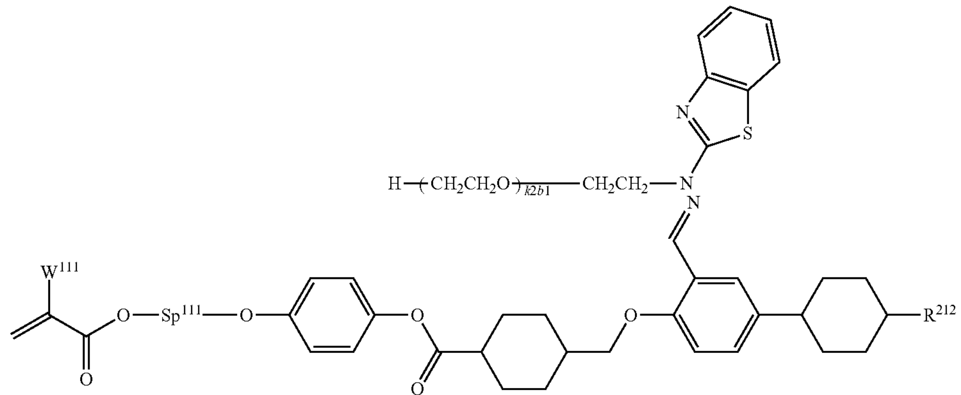
(I-ia-i-6-1)
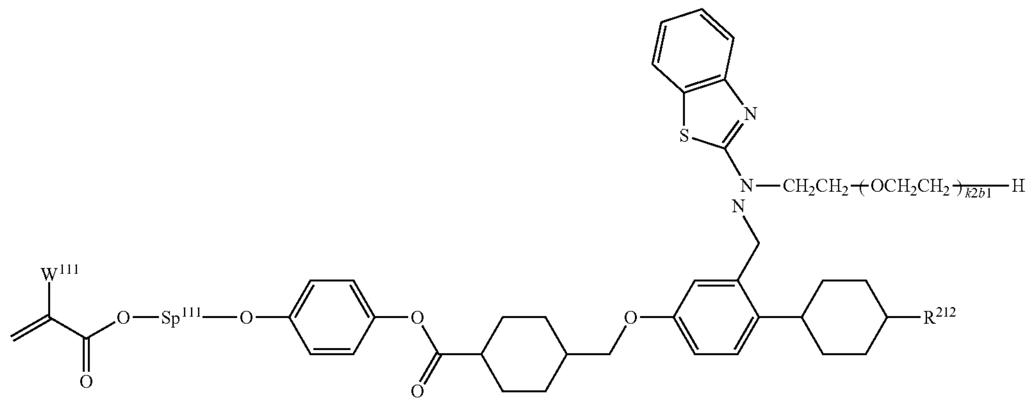
[Chem. 14]
(I-ii-i-1-1)
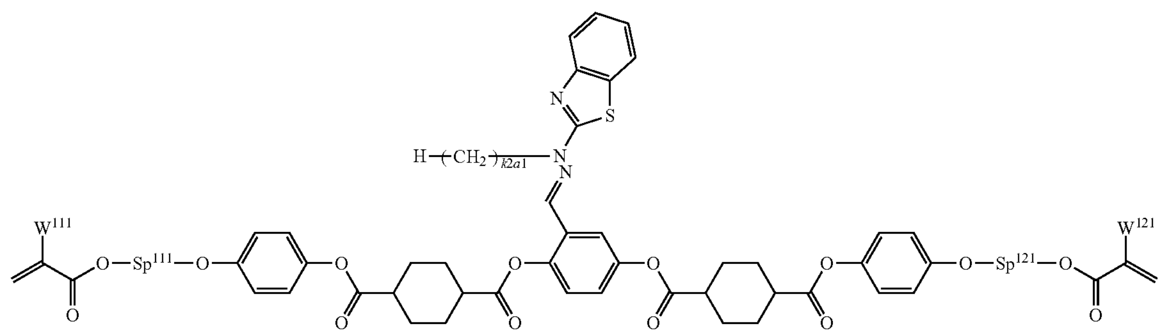
(I-ii-i-2-1)
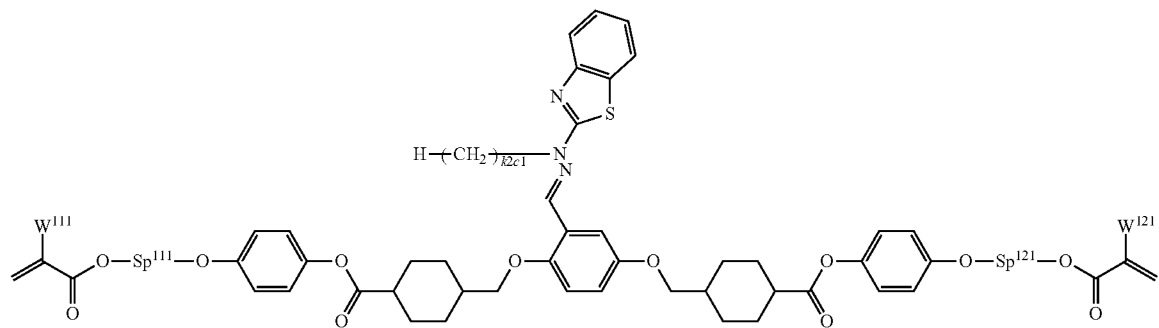

-continued (I-ii-i-2-2)

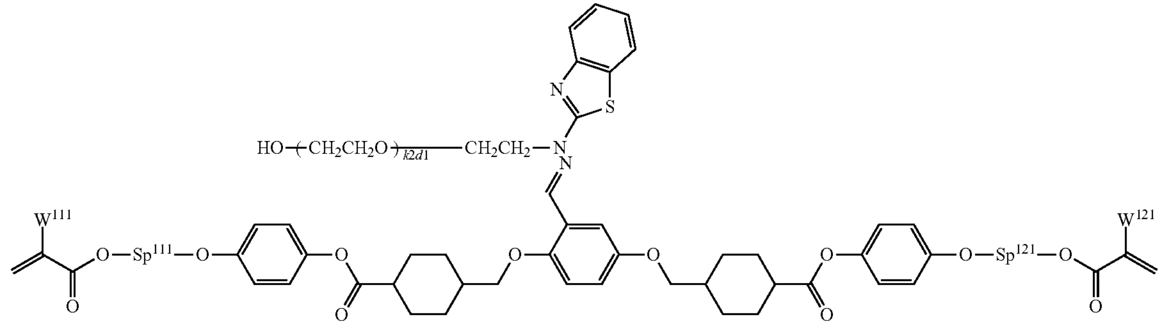

(In the formulae, $W^{111}$ and $W^{121}$ each represent a hydrogen atom or a methyl group, $Sp^{111}$ and $Sp^{121}$ each represent an alkylene group having 2 to 8 carbon atoms, $R^{212}$ represents a linear alkyl group or linear alkoxy group having 1 to 8 carbon atoms, k2a1 represents an integer of 2 to 10, k2b1 represents 1 or 2, k2c1 represents an integer of 3 to 8, and k2d1 represents 1 or 2.)

A compound represented by general formula (II) can be produced by using the compound represented by general formula (I) as an intermediate. The polymerizable compound (II) is preferably a compound represented by formula (II-ii-i-2-1) or formula (II-ii-i-2-2) below:

[Chem. 15]

(II-ii-i-2-1)

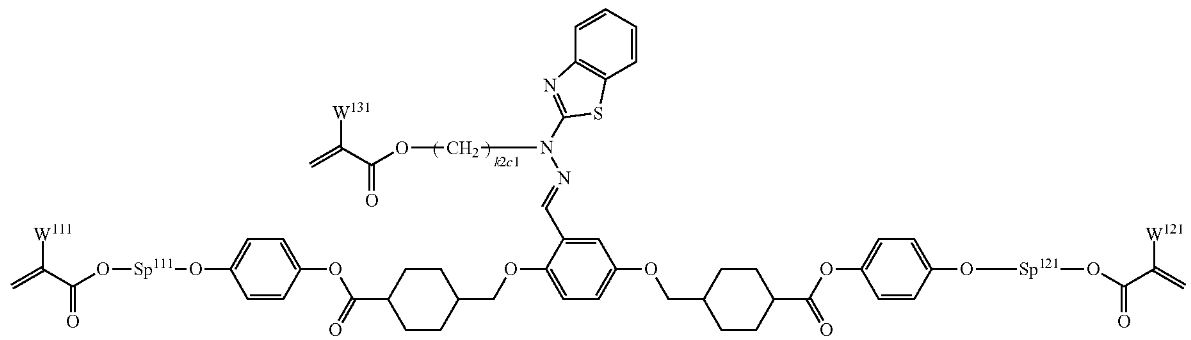

(II-ii-i-2-2)

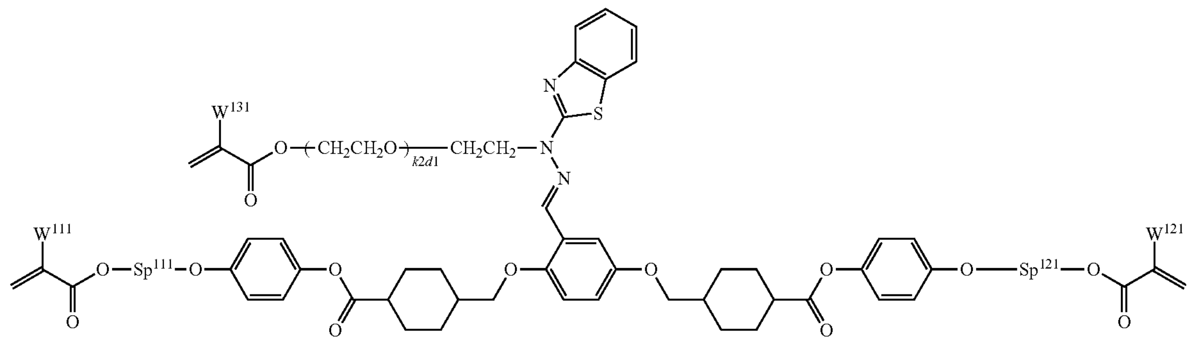

(In the formulae, $W^{111}$, $W^{121}$, and $W^{131}$ each represent a hydrogen atom or a methyl group, $Sp^{111}$ and $Sp^{121}$ each represent an alkylene group having 2 to 8 carbon atoms, k2c1 represents an integer of 3 to 8, and k2d1 represents 1 or 2.)

The compound represented by general formula (I) is preferably produced by the reaction between the compound represented by general formula (I-C) described above and a compound represented by general formula (I-D) below:

[Chem. 16]

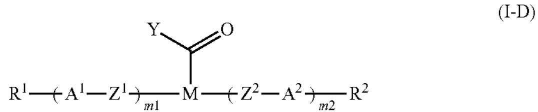

(In the formula, $R^1$ represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms, in which any hydrogen atom may be substituted with a fluorine atom, and one —$CH_2$— or two more non-adjacent —$CH_2$— may each independently be substituted with —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2$—O—, —$OCF_2$—, —$CF_2S$—, —$SCF_2$—, —CH═CH—COO—, —CH═—CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—CH—, —OCO—$CH_2$—, —$CH_2$—COO—, —$CH_2$—OCO—, —CH═CH—, —N═N—, —CH═N—N═CH—, —CF═CF—, or —C≡C—, or $R^1$ represents a group represented by $P^1$—($Sp^1$—$X^1$)$_{k1}$— (in the formula, $P^1$ represents a polymerizable group and preferably represents a group polymerizable by radical polymerization, radical addition polymerization, cation polymerization, or anion polymerization; $Sp^1$ represents a spacer group, and when there are more than one $Sp^1$, they may be the same or different; $X^1$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2$—O—, —$OCF_2$—, —$CF_2S$—, —$SCF_2$—, —CH═CH—COO—, —CH═—CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—CH—, —OCO—$CH_2$—, —$CH_2$—COO—, —CH—OCO—, —CH═CH—, —N═N—, —CH═N—N═CH—, —CF═CF—, —C≡C—, or a single bond, and when there are more than one $X^1$, they may be the same or different; and k1 represents an integer of 0 to 10), $R^2$ represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms, in which any hydrogen atom may be substituted with a fluorine atom and one —$CH_2$— or two more non-adjacent —$CH_2$— may each independently be substituted with —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═C—, —COO—$CH_2CH_2$—, —OCO—$CH_2$—$CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—N═CH—, —CF═CF—, or —C≡C, or $R^2$ represents a group represented by —($X^2$—$Sp^2$)$_{k2}$—$P^2$ (in the formula, $P^2$ represents a polymerizable group and preferably represents a group polymerizable by radical polymerization, radical addition polymerization, cation polymerization, or anion polymerization; $Sp^2$ represents a spacer group, and when there are more than one $Sp^2$, they may be the same or different; $X^2$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—N═CH—, —CF═CF—, —C≡C—, or a single bond, and when there are more than one $X^2$, they may be the same or different; and k2 represents an integer of 0 to 10), $A^1$ and $A^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, which may be unsubstituted or substituted with one or more substituents L; when there are more than one $A^1$, they may be the same or different; when there are more than one $A^2$, they may be the same or different; L represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —$CH_2$— or two more non-adjacent —$CH_2$— may each independently be substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, and any hydrogen atom in the alkyl group may be substituted with a fluorine atom, or L may represent a group represented by $P^L$—($Sp^L$—$X^L$)$_{kL}$—, where: $P^L$ represents a polymerizable group and preferably represents a group polymerizable by radical polymerization, radical addition polymerization, cation polymerization, or anion polymerization; $Sp^L$ represents a spacer group, preferable examples of which are the same as those for $Sp^1$ described above; when there are more than one $Sp^L$, they may be the same or different; $X^L$ represents —O—, —S—, —$OCH_2$—, —$CH^2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—

N═CH—, —CF═CF—, —C═C—, or a single bond, and when there are more than one $X^L$, they may be the same or different; and kL represents an integer of 0 to 10, and when there are more than one kL in the compound, they may be the same or different, $Z^1$ and $Z^2$ each independently represent —O—, —S—, —$OCH_2$—, —$CH_2O$—, —$CH_2CH_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—, —N═CH—, —CH═N—N═CH—, —CF═CF—, —C≡C—, or a single bond; when there are more than one $Z^1$, they may be the same or different; when there are more than one $Z^2$, they may be the same or different; m1 and m2 each independently represent an integer of 0 to 6, and m1+m2 is an integer of 0 to 6; M represents a substituted or unsubstituted trivalent aromatic group; Y represents a hydrogen atom, a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —$CH_2$— or two more non-adjacent —$CH_2$— may each independently be substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, and any hydrogen atom in the alkyl group may be substituted with a fluorine atom; however, the compound represented by general formula (I-D) does not contain an —O—O— bond).

In other words, the compound represented by general formula (I) is preferably produced by a method that includes a first step of obtaining a compound represented by general formula (I-C) by the production method of the invention of the present application; and a second step of obtaining a compound represented by general formula (I) by reacting the obtained compound represented by general formula (I-C) with a compound represented by general formula (I-D). The compound represented by general formula (I) obtained by this production method is particularly preferable as a raw material for optically anisotropic body products since the degree of coloration and the impurity content derived from the first step are low.

The compound represented by general formula (I-D) may be a polymerizable compound or a non-polymerizable compound, but the compound represented by general formula (I-D) is preferably a polymerizable compound. In such a case, a group represented by $P^1$ or $P^2$ is preferably present in at least one of $R^1$ and $R^2$, and particularly preferably, a group represented by $P^1$ or $P^2$ is present in both $R^1$ and $R^2$.

The compounds represented by general formula (I-ia), general formula (I-ib), and general formula (I-ii) above are preferably produced by the reaction between the compound represented by general formula (I-C) described above and compounds represented by general formula (I-D-ia), general formula (I-D-ib), and general formula (I-D-ii) below:

[Chem. 17]

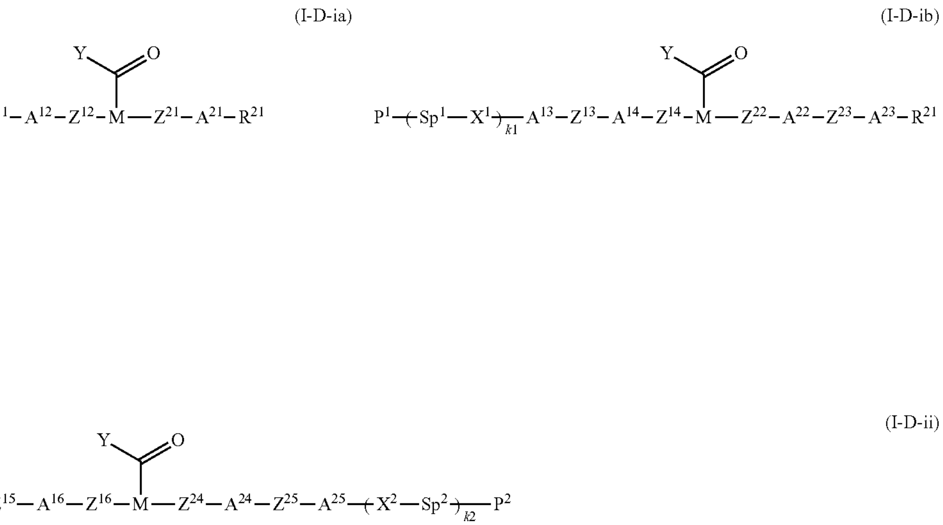

(In the formulae, $P^1$, $P^2$, $Sp^1$, $Sp^2$, $X^1$, $X^2$, k1, k2, M, and Y are the same as those in general formula (I), and $R^{21}$, $A^{11}$, $A^{12}$, $A^{13}$, $A^{14}$, $A^{15}$, $A^{16}$, $A^{21}$, $A^{22}$, $A^{23}$, $A^{24}$, $A^{25}$, $Z^{11}$, $Z^{12}$, $Z^{13}$, $Z^{14}$, $Z^{15}$, $Z^{16}$, $Z^{21}$, $Z^{22}$, $Z^{23}$, $Z^{24}$, and $Z^{25}$ are the same as $R^{21}$, $A^{11}$, $A^{12}$, $A^{13}$, $A^{14}$, $A^{15}$, $A^{16}$, $A^{21}$, $A^{22}$, $A^{23}$, $A^{24}$, $A^{25}$, $Z^{11}$, $Z^{12}$, $Z^{13}$, $Z^{14}$, $Z^{15}$, $Z^{16}$, $Z^{21}$, $Z^{22}$, $Z^{23}$, $Z^{24}$, and $Z^{25}$ in general formula (I-ia), general formula (I-ib), and general formula (I-ii).) The compounds represented by general formula (I-ia-i), general formula ((I-ib-i), and general formula (I-ii-i) are preferably produced by the reaction between the compound represented by general formula (I-C) described above and compounds represented by general formula (I-D-ia-i), general formula (I-D-ib-i), and general formula (I-D-ii-i) below:

[Chem. 18]

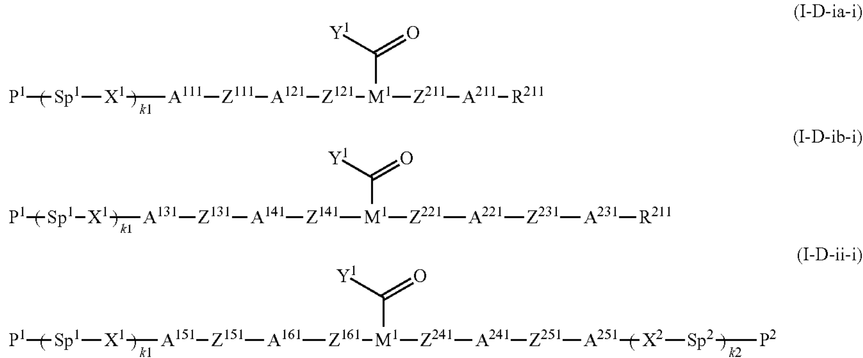

(In the formulae, $P^1$, $P^2$, $Sp^1$, $Sp^2$, $X^1$, $X^2$, k1, and k2 are the same as those in general formula (I), and $R^{211}$, $A^{111}$, $A^{121}$, $A^{131}$, $A^{141}$, $A^{151}$, $A^{161}$, $A^{211}$, $A^{221}$, $A^{231}$, $A^{241}$, $A^{251}$, $Z^{111}$, $Z^{121}$, $Z^{131}$, $Z^{141}$, $Z^{151}$, $Z^{161}$, $Z^{211}$, $Z^{221}$, $Z^{231}$, $Z^{241}$, $Z^{251}$, $M^1$ and $Y^1$ are the same as $R^{211}$, $A^{111}$, $A^{121}$, $A^{131}$, $A^{141}$, $A^{151}$, $A^{161}$, $A^{211}$, $A^{221}$, $A^{231}$, $A^{241}$, $A^{251}$, $Z^{111}$, $Z^{121}$, $Z^{131}$, $Z^{141}$, $Z^{151}$, $Z^{161}$, $Z^{211}$, $Z^{221}$, $Z^{231}$, $Z^{241}$, $Z^{251}$, $M^1$, and $Y^1$ in general formula (I-D-ia-i), general formula (I-D-ib-i), and general formula (I-D-ii-i).) The compounds represented by formula (I-ia-i-1) to formula (I-ii-i-2) are preferably produced by the reaction between a compound represented by general formula (I-C-i) below:

[Chem. 19]

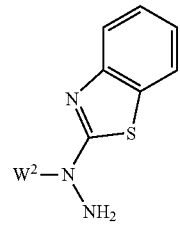

(In the formula, $W^2$ is the same as $W^2$ in general formula (I-C)), and compounds represented by formula (I-D-ia-i-1) to formula (I-D-ii-i-2) below:

[Chem. 20]

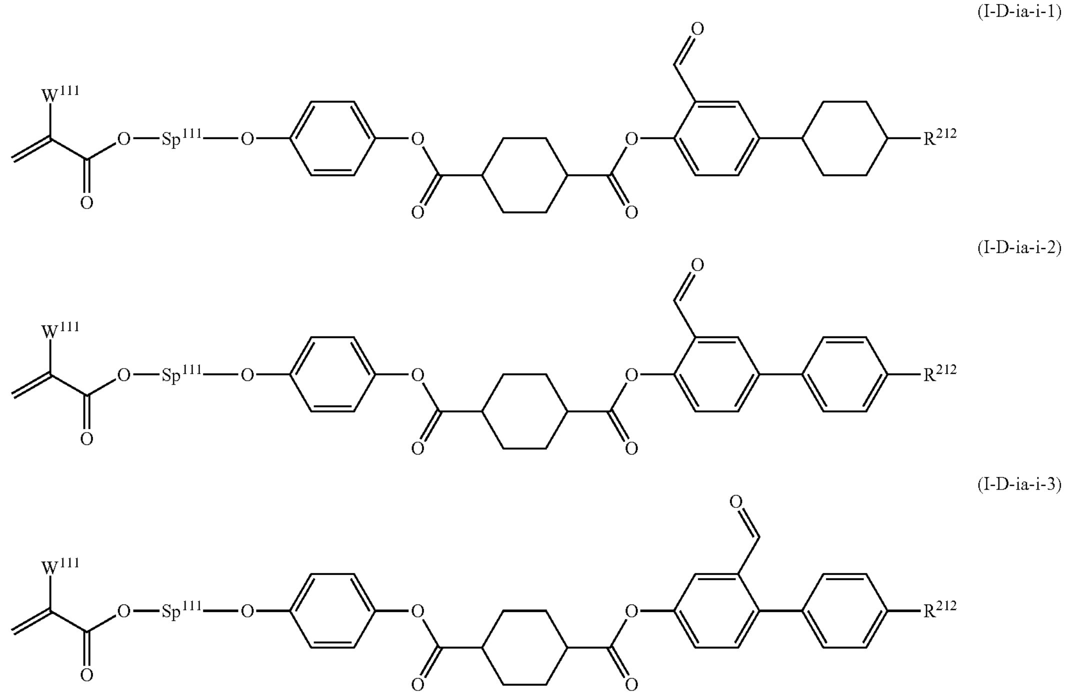

-continued
[Chem. 21]
(I-D-ia-i-4)
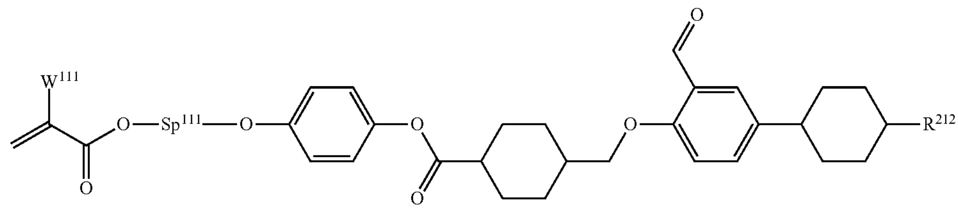
(I-D-ia-i-5)
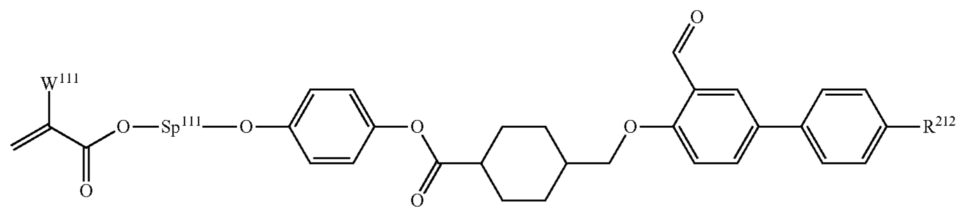
(I-D-ia-i-6)
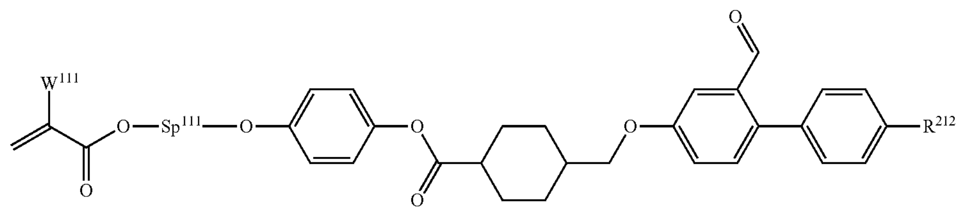
[Chem. 22]
(I-D-ib-i-1)
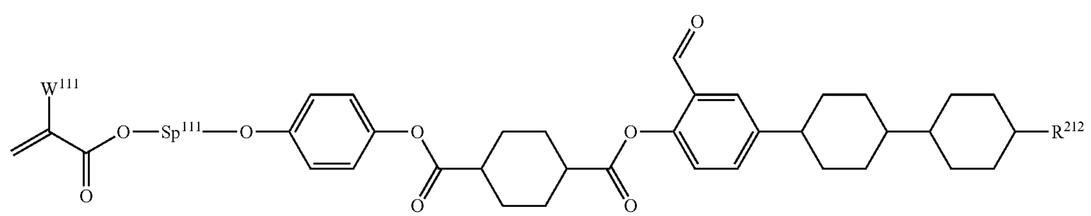
(I-D-ib-i-2)
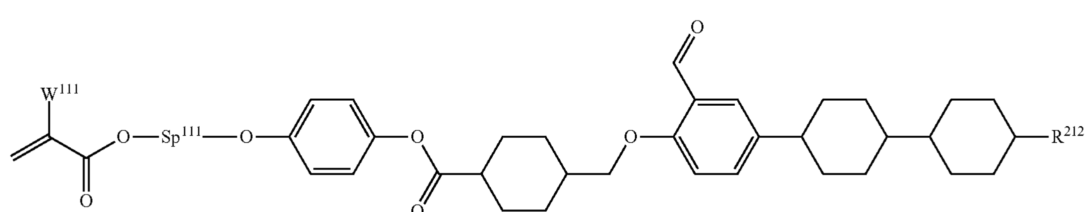
(I-D-ii-i-1)
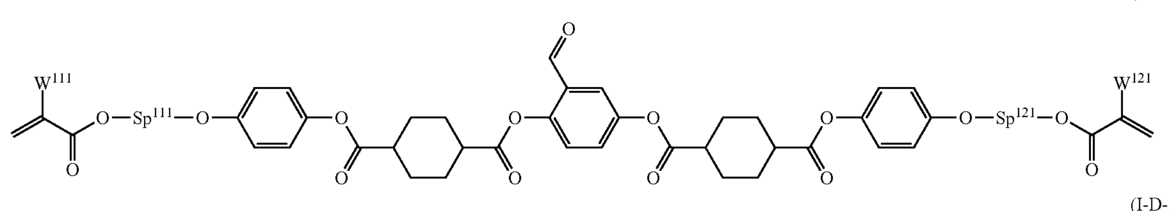
(I-D-ii-i-2)
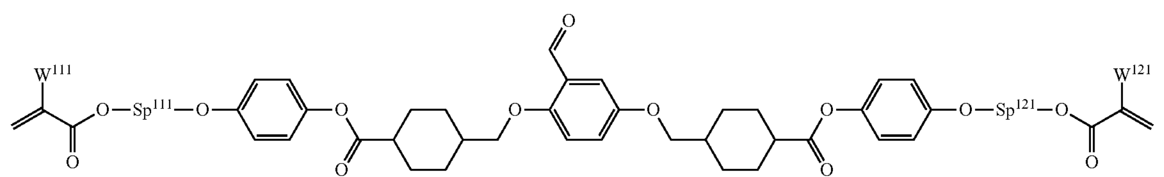

(In the formulae, $W^{111}$, $W^{121}$, $Sp^{111}$, $Sp^{121}$, and $R^{212}$ are the same as $W^{111}$, $W^{121}$, $Sp^{111}$, $Sp^{121}$, and $R^{212}$ in formula (I-ia-i-1) to formula (I-ii-i-2).) The compounds represented by formula (I-ia-i-1-1) to formula (I-ii-i-2-2) are preferably produced by the reaction between a compound represented by general formula (I-C-a-3), general formula (I-C-a-1), general formula (I-C-a-1), or general formula (I-C-a-6) below:

[Chem. 23]

(I-C-a-3)

(I-C-a-1)

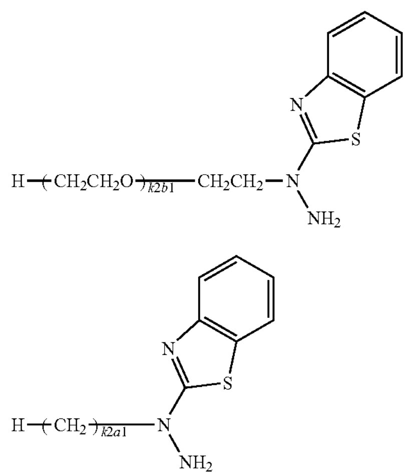

-continued (I-C-a-4)

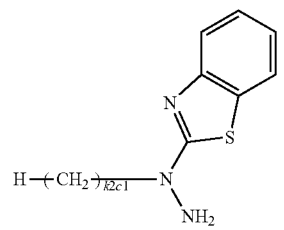

(I-C-a-6)

(In the formulae, k2a1, k2b1, k2c1, and k2d1 are the same as k2a1, k2b1, k2c1, and k2d1 in formula (I-ia-i-1-1) to formula (I-ii-i-2-2).), and compounds represented by formula (I-D-ia-i-1-1) to formula (I-D-ii-i-2-2) below:

[Chem. 24]

(I-D-ia-i-1-1)

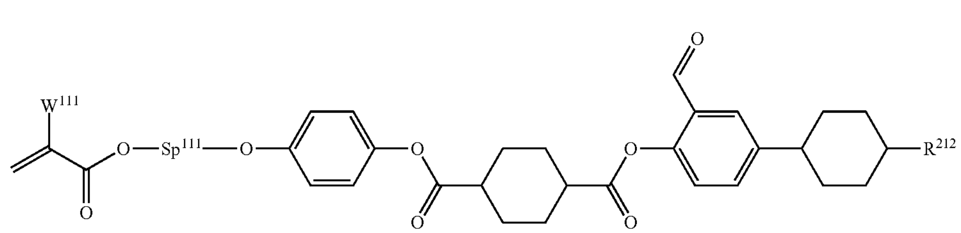

(I-D-ia-i-4-1)

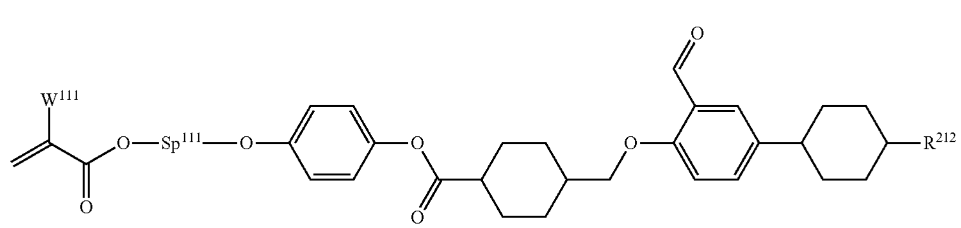

(I-D-ia-i-6-1)

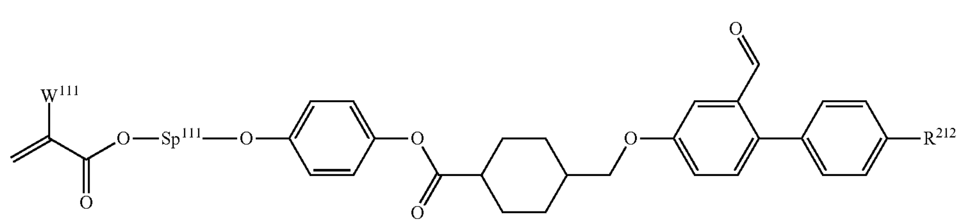

-continued

[Chem. 25]

(I-D-ii-i-1-1)

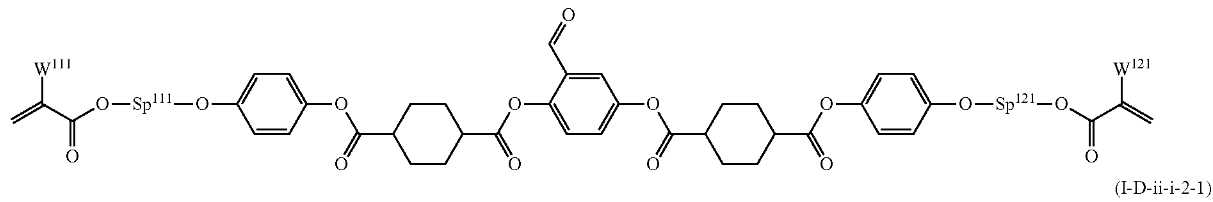

(I-D-ii-i-2-1)

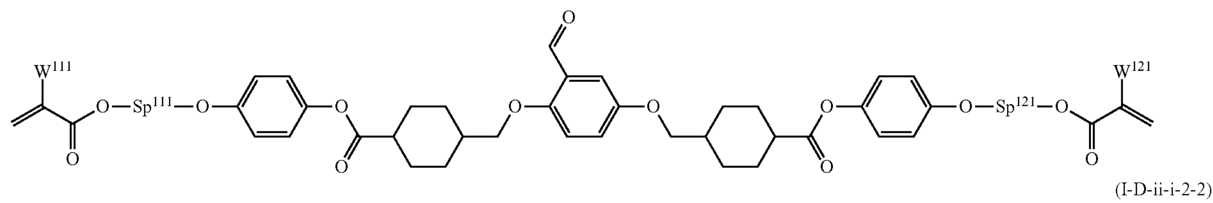

(I-D-ii-i-2-2)

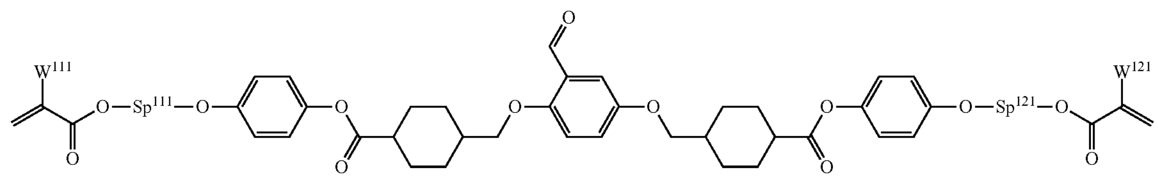

(In the formulae, $W^{111}$, $W^{121}$, $Sp^{111}$, $Sp^{121}$, and $R^{212}$ are the same as $W^{111}$, $W^{121}$, $Sp^{111}$, $Sp^{121}$, and $R^{212}$ in formula (I-ia-i-1-1) to formula (I-ii-i-2-2).)

In the reaction between the compound represented by general formula (I-C) and the compound represented by general formula (I-D), an acid is preferably added from the viewpoint of the reaction rate. The acid may be an inorganic acid or an organic acid. Examples of the inorganic acid include hydrochloric acid, sulfuric acid, and nitric acid. Examples of the organic acid include acetic acid, formic acid, oxalic acid, p-toluenesulfonic acid, p-toluenesulfonic acid monohydrate, pyridinium p-toluenesulfonate, and (±)-10-camphorsulfonic acid. From the viewpoint of ease of purification, p-toluenesulfonic acid monohydrate, pyridinium p-toluenesulfonate, (±)-10-camphorsulfonic acid, etc., are preferable. The amount of the acid added relative to the compound represented by general formula (I-D) is preferably 0.001 to 10 equivalent, more preferably 0.001 to 1 equivalent, and particularly preferably 0.01 to 0.5 equivalent.

The reaction temperature in the reaction described above is preferably −100° C. to 200° C., and, from the viewpoints of yield and reaction rate, is more preferably −50° C. to 150° C., yet more preferably −20° C. to 120° C., still more preferably 0° C. to 80° C., and particularly preferably room temperature to 50° C.

The reaction solvent is preferably an alcohol or an ether, and is more preferably a mixed solvent containing an alcohol and an ether. More specific examples are those described above.

Moreover, if needed, the reaction product may be purified after the reaction. Examples of the purification method include chromatography, filtration, recrystallization, distillation, sublimation, reprecipitation, adsorption, centrifugation, liquid separation treatment, and dispersion washing. When a purifier is to be used, examples of the purifier include silica gel, alumina, activated carbon, activated clay, celite, zeolite, mesoporous silica, carbon nanotube, carbon nanohorn, Bincho charcoal, charcoal, graphene, ion exchange resin, acid clay, silicon dioxide, diatomaceous earth, pearlite, cellulose, organic polymer, and porous gel.

In the steps described above, in handling the substances that are instable with oxygen and/or moisture, the operation is preferably performed in inert gas, such as nitrogen gas or argon gas.

EXAMPLES

The present invention will now be described in further details through examples, but the examples do not limit the scope of the present invention. Moreover, for the compositions of Examples and Comparative Examples described below, "%" means "% by mass". In the respective steps, in handling the substances that are instable with oxygen and/or moisture, the operation was performed in inert gas, such as nitrogen gas or argon gas.

(GC Analysis Conditions)

Columns: Agilent Technologies, J & W Column DB-1HT, 15 m×0.25 mm×0.10 μm

Temperature program: 100° C. (1 minute)-(20° C./minute)-250° C.-(10° C./minute)-380° C.-(7° C./minute)-400° C. (2.64 minutes)

Inlet temperature: 350° C.

Detector temperature: 400° C.

(UPLC Analysis Conditions)

Columns: Waters ACQUITY UPLC BEH $C_{18}$, 2.1×100 mm, 1.7 μm

Elution solvent: acetonitrile/water (90:10), acetonitrile/water (85:15), 0.1% formic acid-acetonitrile/water (90:10), or 0.1% formic acid-acetonitrile/water (70:30)

Flow rate: 0.4 mL/min

Detector: UV (PDA)

Column oven: 40° C.

(Example 1) Production of Compound Represented by Formula (C-1)

[Chem. 26]

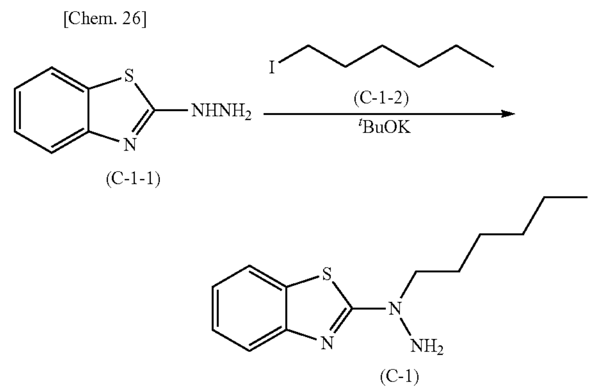

In a nitrogen atmosphere, 2.00 g of a compound represented by formula (C-1-1) and 20 mL of tetrahydrofuran were added into a reactor. While the mixture was being cooled over ice, 1.49 g of potassium tert-butoxide was added, followed by stirring for 2 hours. A solution prepared by dissolving 2.82 g of a compound represented by formula (C-1-2) in 3 mL of tetrahydrofuran was added thereto dropwise. After the resulting mixture was stirred for 5 hours at room temperature, the mixture was diluted with 100 mL of dichloromethane and was poured into water. The organic layer was washed with brine and dried over sodium sulfate, and the solvent was distilled away. Purification was performed by column chromatography (silica gel, hexane/ethyl acetate (75:25)) so as to obtain 2.35 g of a compound represented by formula (C-1). The yield from the compound represented by formula (C-1-1) was 78%. The reaction solution after the reaction had slight coloration.

(Comparative Example 1) Production of Compound Represented by Formula (C-1R) by Method Described in PTL 3

[Chem. 27]

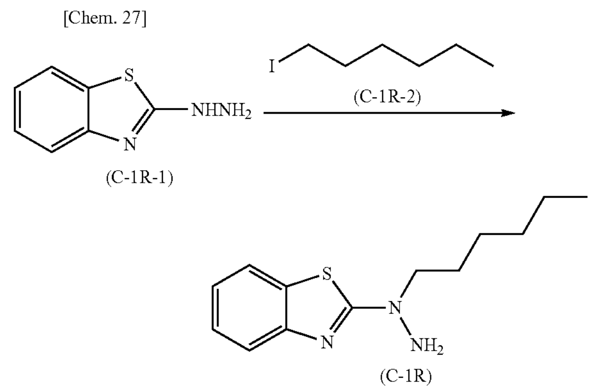

In a nitrogen atmosphere, 2.00 g of a compound represented by formula (C-1R-1), 20 mL of N,N-dimethylformamide, 8.36 g of potassium carbonate, and 3.08 g of a compound represented by formula (C-1R-2) were added into a reactor, and the resulting mixture was stirred at 50° C. for 7 hours. After cooling, the mixture was poured into 200 mL of water, and extracted with 300 mL of ethyl acetate. After drying over sodium sulfate, the solvent was distilled away. Purification was performed by column chromatography (silica gel, hexane/ethyl acetate (75:25)) so as to obtain 2.10 g of a compound represented by formula (C-1R). The yield from the compound represented by formula (C-1R-1) was 70%. The reaction solution after the reaction had extensive coloration.

(Example 2) Production of Compound Represented by Formula (C-2)

[Chem. 28]

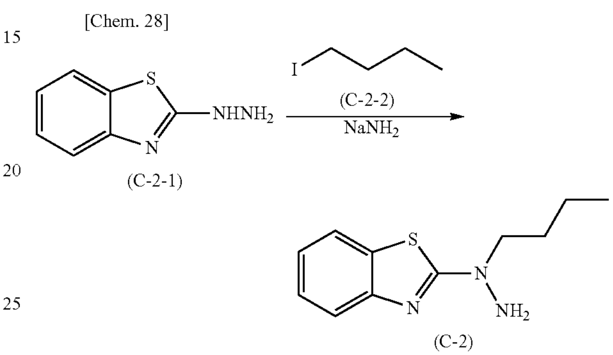

In a nitrogen atmosphere, 2.00 g of a compound represented by formula (C-2-1) and 20 mL of tetrahydrofuran were added into a reactor. While the mixture was being cooled over ice, 0.52 g of sodium amide was added, followed by stirring at room temperature for 2 hours. A solution prepared by dissolving 2.45 g of a compound represented by formula (C-2-2) in 5 mL of tetrahydrofuran was added thereto dropwise. After the resulting mixture was stirred for 5 hours at room temperature, the mixture was diluted with 100 mL of dichloromethane and was poured into water. The organic layer was washed with brine and dried over sodium sulfate, and the solvent was distilled away. Column chromatography (silica gel, dichloromethane) and recrystallization (dichloromethane/hexane) were performed to obtain 2.49 g of a compound represented by formula (C-2). The yield from the compound represented by formula (C-2-1) was 93%. The reaction solution after the reaction had slight coloration.

(Comparative Example 2) Production of Compound Represented by Formula (C-2R) by Method Described in PTL 3

[Chem. 29]

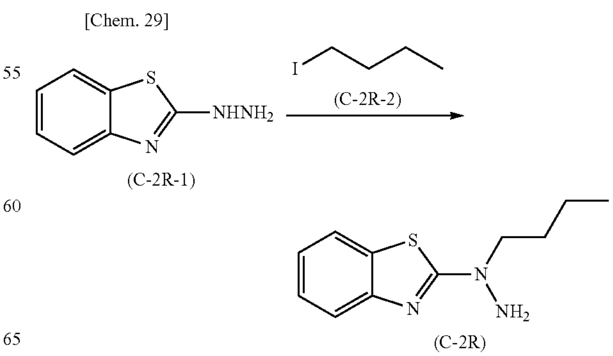

In a nitrogen atmosphere, 2.00 g of a compound represented by formula (C-2R-1), 20 mL of N,N-dimethylformamide, 8.36 g of potassium carbonate, and 2.67 g of a compound represented by formula (C-2R-2) were added into a reactor, and the resulting mixture was stirred at 50° C. for 7 hours. After cooling, the mixture was poured into 200 mL of water, and extracted with 300 mL of ethyl acetate. After drying over sodium sulfate, the solvent was distilled away. Purification was performed by column chromatography (silica gel, hexane/ethyl acetate (75:25)) so as to obtain 2.34 g of a compound represented by formula (C-2R). The yield from the compound represented by formula (C-2R-1) was 87%. The reaction solution after the reaction had extensive coloration.

(Example 3) Production of Compound Represented by Formula (C-3)

[Chem. 30]

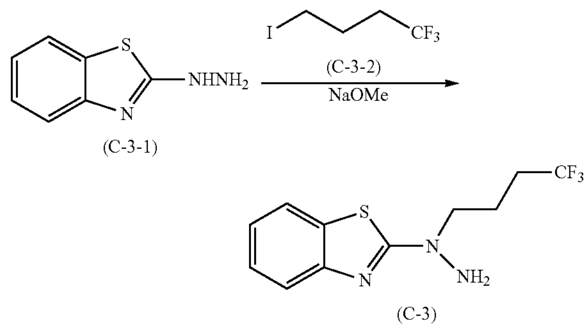

In a nitrogen atmosphere, 2.00 g of a compound represented by formula (C-3-1) and 20 mL of tetrahydrofuran were added into a reactor. While the mixture was being cooled over ice, 0.69 g of sodium methoxide was added, followed by stirring at room temperature for 2 hours. A solution prepared by dissolving 3.17 g of a compound represented by formula (C-3-2) in 5 mL of tetrahydrofuran was added thereto dropwise. After the resulting mixture was stirred for 5 hours at room temperature, the mixture was diluted with 100 mL of dichloromethane and was poured into water. The organic layer was washed with brine and dried over sodium sulfate, and the solvent was distilled away. Column chromatography (silica gel, dichloromethane) and recrystallization (dichloromethane/hexane) were performed to obtain 2.67 g of a compound represented by formula (C-3). The yield from the compound represented by formula (C-3-I) was 80%. The reaction solution after the reaction had slight coloration.

(Comparative Example 3) Production of Compound Represented by Formula (C-3R) by Method Described in PTL 3

[Chem. 31]

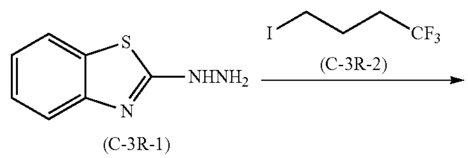

-continued

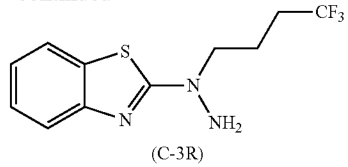

In a nitrogen atmosphere, 1.45 g of a compound represented by formula (C-3R-1), 20 mL of N,N-dimethylformamide, 3.63 g of potassium carbonate, and 2.50 g of a compound represented by formula (C-3R-2) were added into a reactor, and the resulting mixture was stirred at 80° C. for 8 hours. After cooling, the mixture was poured into 200 mL of water, and extracted with 300 mL of ethyl acetate. After drying over sodium sulfate, the solvent was distilled away. Purification by column chromatography (silica gel, hexane/ethyl acetate (85:15)) was performed so as to obtain 0.96 g of a compound represented by formula (C-3R). The yield from the compound represented by formula (C-3R-1) was 40%. The reaction solution after the reaction had extensive coloration.

(Example 4) Production of Compound Represented by Formula (C-4)

[Chem. 32]

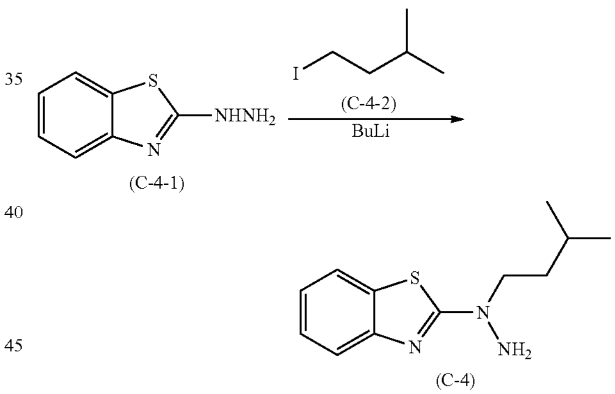

In a nitrogen atmosphere, 2.00 g of a compound represented by formula (C-4-1) and 20 mL of tetrahydrofuran were added into a reactor. The mixture was cooled to −70° C., 8.3 mL of butyl lithium (1.6 mol/L hexane solution) was added dropwise, and the mixture was warmed to −10° C., followed by stirring for 1 hour. A solution prepared by dissolving 2.52 g of a compound represented by formula (C-4-2) in 5 mL of tetrahydrofuran was added thereto dropwise. After the resulting mixture was stirred for 5 hours at room temperature, the mixture was diluted with 100 mL of dichloromethane and was poured into water. The organic layer was washed with brine and dried over sodium sulfate, and the solvent was distilled away. Purification by column chromatography (silica gel, hexane/ethyl acetate (75:25)) was performed so as to obtain 1.99 g of a compound represented by formula (C-4). The yield from the compound represented by formula (C-4-1) was 70%. The reaction solution after the reaction had slight coloration.

(Comparative Example 4) Production of Compound Represented by Formula (C-4R) by Method Described in PTL 3

[Chem. 33]

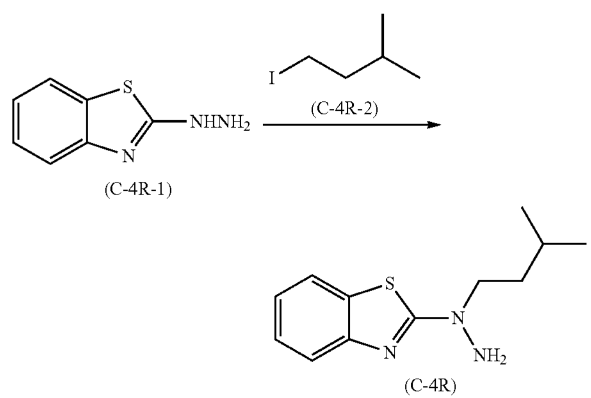

In a nitrogen atmosphere, 3.00 g of a compound represented by formula (C-4R-1) and 20 mL of tetrahydrofuran were added into a reactor. At 0° C., 11.4 mL of lithium bis(trimethylsilyl)amide (26% tetrahydrofuran solution) was added thereto dropwise, followed by stirring for 30 minutes. Thereto, 2.9 mL of a compound represented by formula (C-4R-2) was added, and the mixture was stirred at 25° C. for 6 hours. The mixture was poured into 100 mL of water, and extracted with 150 mL of ethyl acetate. After drying over sodium sulfate, the solvent was distilled away. Purification was performed by column chromatography (silica gel, hexane/ethyl acetate (75:25)) so as to obtain 2.07 g of a compound represented by formula (C-4R). The yield from the compound represented by formula (C-4R-1) was 48%. The reaction solution after the reaction had extensive coloration.

(Example 5) Production of Compound Represented by Formula (C-5)

[Chem. 34]

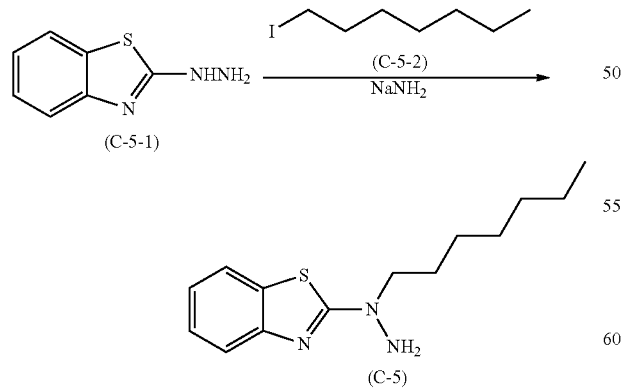

In a nitrogen atmosphere, 2.00 g of a compound represented by formula (C-5-1), 3.01 g of a compound represented by formula (C-5-2), and 20 mL of tetrahydrofuran were added into a reactor. While the mixture was being cooled over ice, 0.50 g of sodium amide was added, followed by stirring at room temperature for 5 hours. The mixture was diluted with 100 mL of dichloromethane and was poured into water. The organic layer was washed with brine and dried over sodium sulfate, and the solvent was distilled away. Column chromatography (silica gel, dichloromethane) and recrystallization (dichloromethane/hexane) were performed to obtain 3.00 g of a compound represented by formula (C-5). The yield from the compound represented by formula (C-5-1) was 94%. The reaction solution after the reaction had slight coloration.

(Comparative Example 5) Production of Compound Represented by Formula (C-5R) by Method Described in PTL 1

[Chem. 35]

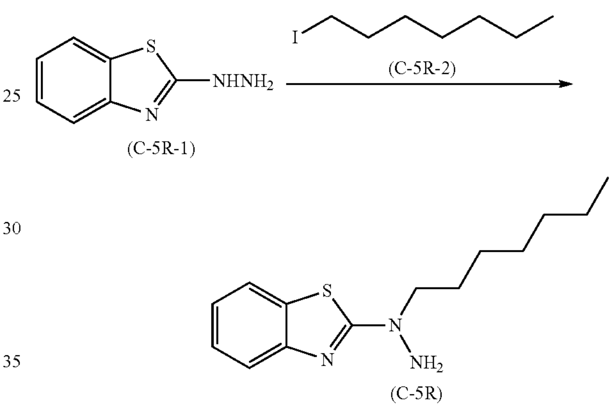

In a nitrogen atmosphere, 2.00 g of a compound represented by formula (C-5R-1), 30 mL of N,N-dimethylformamide, and 7.88 g of cesium carbonate were added into a reactor. Thereto, 3.28 g of a compound represented by formula (C-5R-2) was added dropwise at 0° C., and the mixture was stirred at 25° C. for 3 hours. The mixture was poured into 200 mL of water, and extracted with 100 mL of ethyl acetate twice. After drying over sodium sulfate, the solvent was distilled away. Purification was performed by column chromatography (silica gel, hexane/ethyl acetate (85:15)) so as to obtain 1.81 g of a compound represented by formula (C-5R). The yield from the compound represented by formula (C-5R-1) was 57%. The reaction solution after the reaction had extensive coloration.

(Example 6) Production of Compound Represented by Formula (C-6)

[Chem. 36]

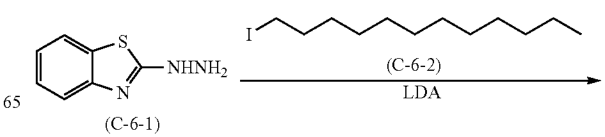

-continued

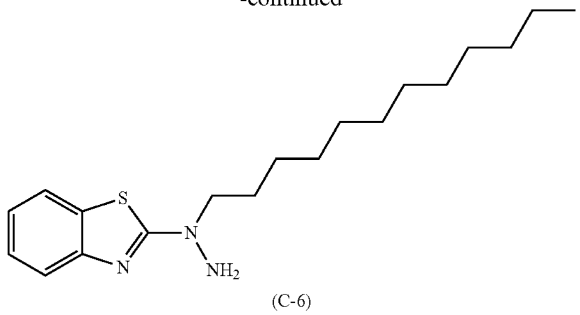

(C-6)

In a nitrogen atmosphere, 9.7 mL of lithium diisopropylamide (1.5 mol/L tetrahydrofuran/ethylbenzene/heptane solution) was added into a reactor. The solution was cooled to −20° C., and a solution prepared by dissolving 2.00 g of a compound represented by formula (C-6-1) in 20 mL of tetrahydrofuran was added thereto dropwise, followed by stirring for 1 hour. A solution prepared by dissolving 3.94 g of a compound represented by formula (C-6-2) in 8 mL of tetrahydrofuran was added thereto dropwise. After the resulting mixture was stirred for 5 hours at room temperature, the mixture was diluted with 100 mL of dichloromethane and was poured into water. The organic layer was washed with brine and dried over sodium sulfate, and the solvent was distilled away. Purification was performed by column chromatography (alumina, dichloromethane) so as to obtain 2.95 g of a compound represented by formula (C-6). The yield from the compound represented by formula (C-6-1) was 73%. The reaction solution after the reaction had slight coloration.

(Comparative Example 6) Production of Compound Represented by Formula (C-6R) by Method Described in PTL 1

[Chem. 37]

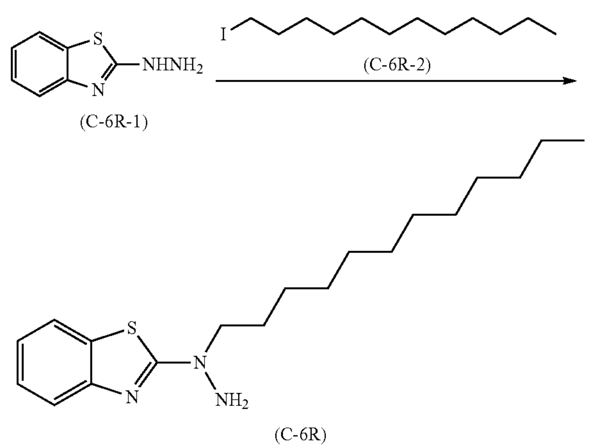

(C-6R)

In a nitrogen atmosphere, 3.00 g of a compound represented by formula (C-6R-1), 45 mL of N,N-dimethylformamide, 11.9 g of cesium carbonate, and 6.45 g of a compound represented by formula (C-6R-2) were added into a reactor, and the resulting mixture was stirred at 25° C. for 20 hours. The mixture was poured into 200 mL of water, and extracted with 300 mL of ethyl acetate. After drying over sodium sulfate, the solvent was distilled away. Purification was performed by column chromatography (silica gel, toluene/ethyl acetate (95:5)) so as to obtain 2.93 g of a compound represented by formula (C-6R). The yield from the compound represented by formula (C-6R-1) was 48%. The reaction solution after the reaction had extensive coloration.

(Example 7) Production of Compound Represented by Formula (C-7)

[Chem. 38]

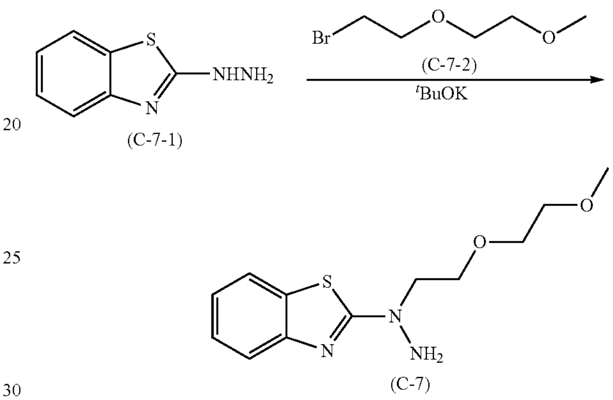

In a nitrogen atmosphere, 2.00 g of a compound represented by formula (C-7-1) and 20 mL of N,N-dimethylformamide were added into a reactor. While the mixture was being cooled over ice, 1.49 g of potassium tert-butoxide was added, followed by stirring for 1 hour at room temperature. While the mixture was cooled over ice, a solution prepared by dissolving 2.44 g of a compound represented by formula (C-7-2) in 3 mL of N,N-dimethylformamide was added thereto dropwise. After the resulting mixture was stirred for 5 hours at room temperature, the mixture was diluted with 100 mL of dichloromethane and was poured into water. The organic layer was washed with brine and dried over sodium sulfate, and the solvent was distilled away. Column chromatography (alumina, dichloromethane) and recrystallization (dichloromethane/hexane) were performed to obtain 3.04 g of a compound represented by formula (C-7). The yield from the compound represented by formula (C-7-1) was 94%. The reaction solution after the reaction had slight coloration.

(Example 8) Production of Compound Represented by Formula (C-8)

[Chem. 39]

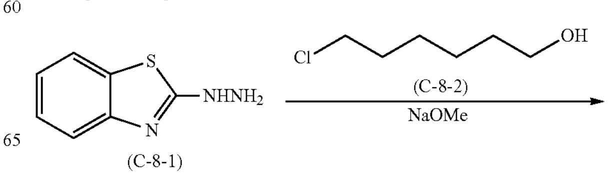

-continued

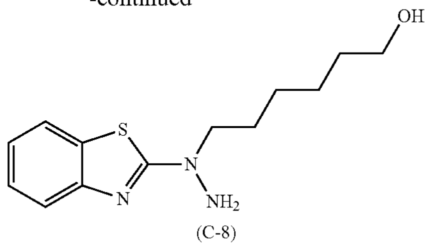

In a nitrogen atmosphere, 2.00 g of a compound represented by formula (C-8-1) and 20 mL of tetrahydrofuran were added into a reactor. While the mixture was being cooled over ice, 0.85 g of sodium methoxide was added, followed by stirring at room temperature for 1 hour. While the mixture was being cooled over ice, a solution prepared by dissolving 1.98 g of a compound represented by formula (C-8-2) in 3 mL of tetrahydrofuran was added thereto dropwise. After the resulting mixture was stirred for 5 hours at room temperature, the mixture was diluted with 100 mL of dichloromethane and was poured into water. The organic layer was washed with brine and dried over sodium sulfate, and the solvent was distilled away. Column chromatography (alumina, dichloromethane) and recrystallization (dichloromethane/hexane) were performed to obtain 2.73 g of a compound represented by formula (C-8). The yield from the compound represented by formula (C-8-1) was 85%. The reaction solution after the reaction had slight coloration.

(Example 9) Production of Compound Represented by Formula (C-9)

[Chem. 40]

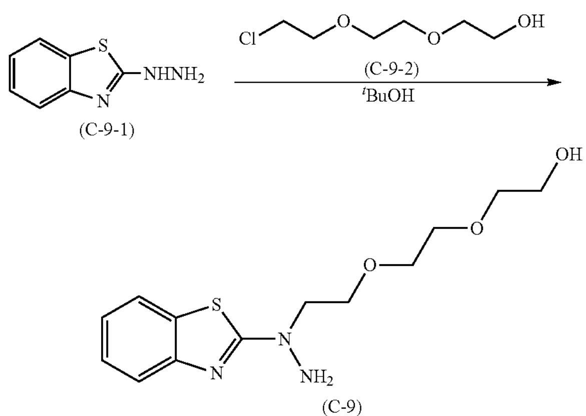

In a nitrogen atmosphere, 2.00 g of a compound represented by formula (C-9-1), 2.45 g of a compound represented by formula (C-9-2), and 20 mL of N,N-dimethylformamide were added into a reactor. While the mixture was being cooled over ice, a tetrahydrofuran solution of 1.49 g of potassium tert-butoxide was added dropwise. After the resulting mixture was stirred for 5 hours at room temperature, the mixture was diluted with 100 mL of dichloromethane and was poured into water. The organic layer was washed with brine and dried over sodium sulfate, and the solvent was distilled away so as to obtain 3.24 g of a compound represented by formula (C-9). The yield from the compound represented by formula (C-9-1) was 90%. The reaction solution after the reaction had slight coloration.

(Example 10) Production of Compound Represented by Formula (C-10)

[Chem. 41]

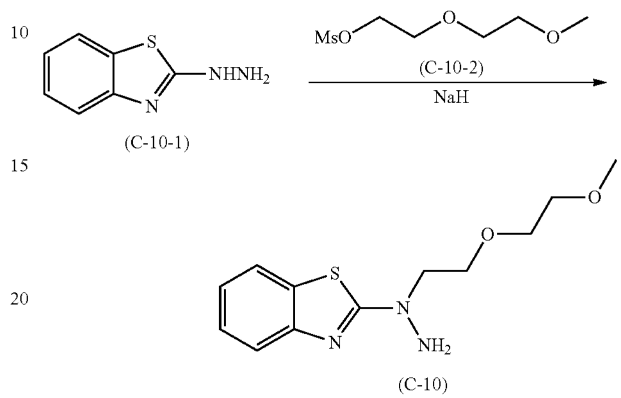

In a nitrogen atmosphere, 2.00 g of a compound represented by formula (C-10-1) and 20 mL of N,N-dimethylformamide were added into a reactor. While the mixture was being cooled over ice, 0.32 g of sodium hydride was added, followed by stirring at room temperature for 1 hour. While the mixture was being cooled over ice, a solution prepared by dissolving 2.64 g of a compound represented by formula (C-10-2) (in the formula, MsO represents a methanesulfonyloxy group) in 3 mL of N,N-dimethylformamide was added thereto dropwise. After the resulting mixture was stirred for 5 hours at room temperature, the mixture was diluted with 100 mL of dichloromethane and was poured into water. The organic layer was washed with brine and dried over sodium sulfate, and the solvent was distilled away. Column chromatography (alumina, dichloromethane) and recrystallization (dichloromethane/hexane) were performed to obtain 2.95 g of a compound represented by formula (C-10). The yield from the compound represented by formula (C-7-1) was 91%. The reaction solution after the reaction had slight coloration.

Compounds represented by formula (C-11) to formula (C-22) below were produced by the same method as that described above.

[Chem. 42]

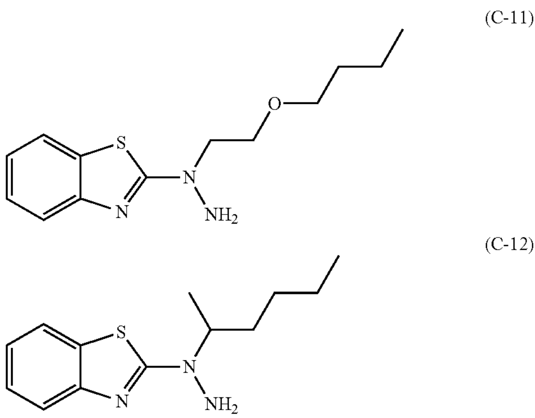

-continued (C-13)

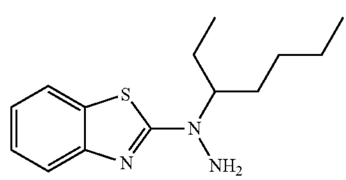

(C-14)

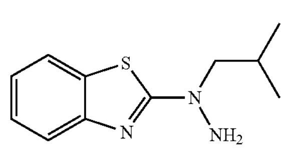

(C-15)

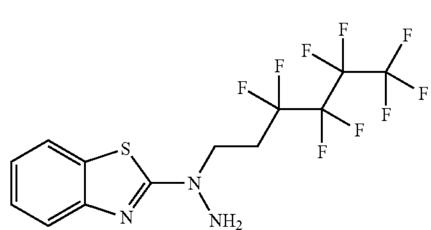

(C-16)

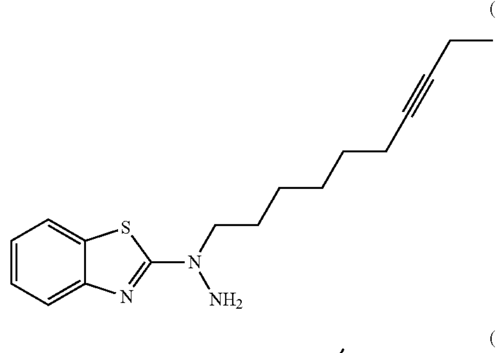

(C-17)

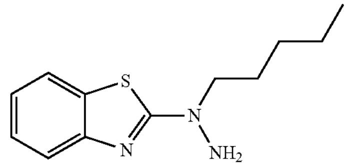

(C-18)

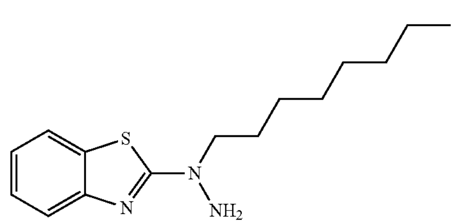

(C-19)

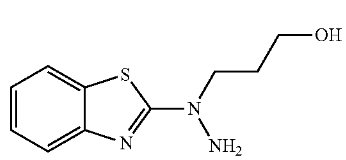

(C-20)

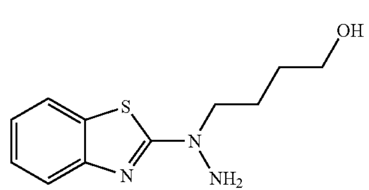

-continued (C-21)

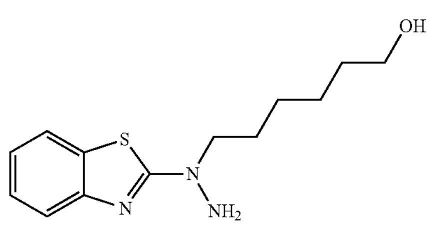

(C-22)

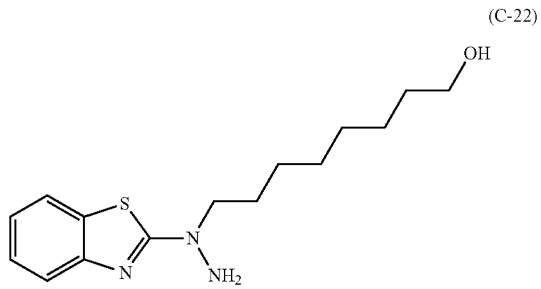

(Example 11) Production of Compound Represented by Formula (C-23)

[Chem. 43]

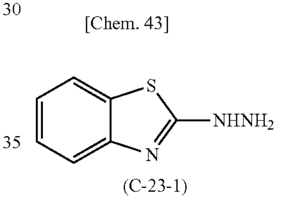

(C-23-1)

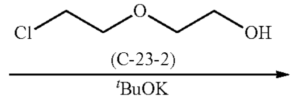

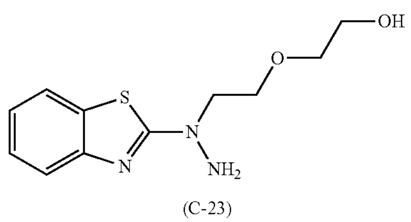

(C-23)

In a nitrogen atmosphere, 2.00 g of a compound represented by formula (C-23-1), 1.81 g of a compound represented by formula (C-23-2), and 20 mL of N,N-dimethylformamide were added into a reactor. While the mixture was being cooled over ice, a tetrahydrofuran solution of 1.49 g of potassium tert-butoxide was added dropwise. After the resulting mixture was stirred for 5 hours at room temperature, the mixture was diluted with 100 mL of dichloromethane and was poured into water. The organic layer was washed with brine and dried over sodium sulfate, and the solvent was distilled away so as to obtain 2.79 g of a compound represented by formula (C-23). The yield from the compound represented by formula (C-23-1) was 91%. The reaction solution after the reaction had slight coloration.

(Example 12) Production of Compound Represented by Formula (I-1)

[Chem. 44]

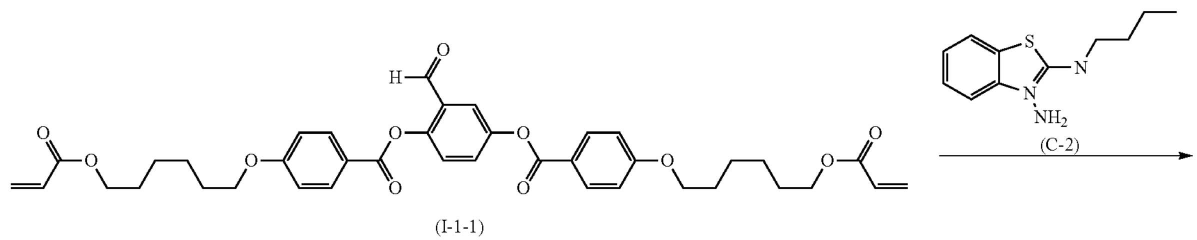

(I-1-1)

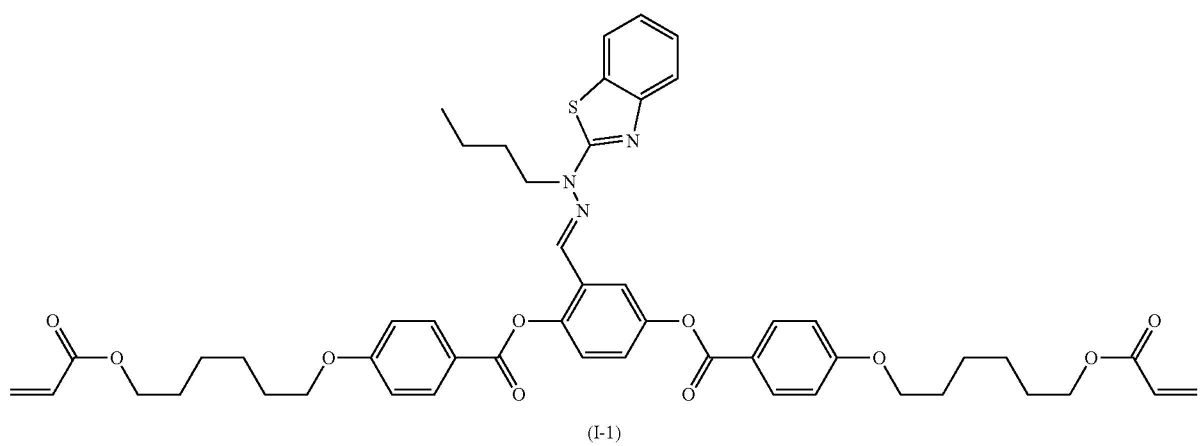

(I-1)

A compound represented by formula (I-1-1) was produced by the method described in International Publication No. WO 2012/147904 A1. Into a reactor, 3.00 g of a compound represented by formula (I-1-1), a 0.97 g of a compound represented by formula (C-2) prepared in Example 2, 0.10 g of p-toluenesulfonic acid monohydrate, 20 mL of tetrahydrofuran, and 10 mL of 2-propanol were added, followed by heating and stirring at 50° C. for 6 hours. The mixture was diluted with 100 mL of dichloromethane and was washed with brine. Purification by column chromatography (silica gel, dichloromethane) and recrystallization (dichloromethane/methanol) was performed to obtain 2.33 g of a compound represented by formula (I-1).

(Example 7) Production of Compound Represented by Formula (I-1R)

[Chem. 45]

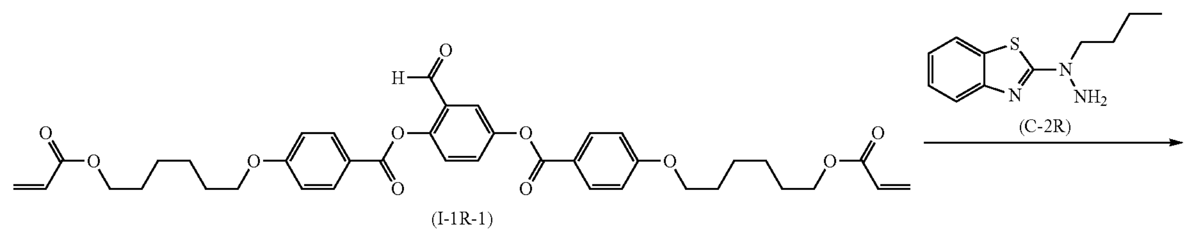

(I-1R-1)

-continued

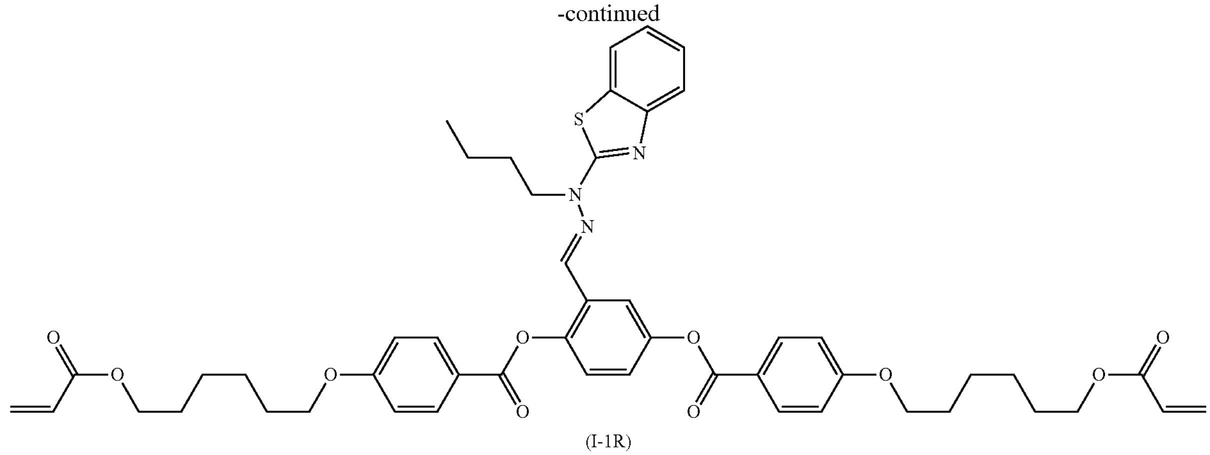

(I-1R)

A compound represented by formula (I-1R) was produced by the same method as in Example 12 by using the compound represented by formula (C-2R) prepared in Comparative Example 2.

In the same manner as described above, the compound represented by formula (C-1) prepared in Example 1, the compound represented by formula (C-3) prepared in Example 3, and the compound represented by formula (C-4) prepared in Example 4 were used to respectively produce compounds represented by formula (I-2), formula (I-3), and formula (I-4) below.

[Chem. 46]

(I-2)

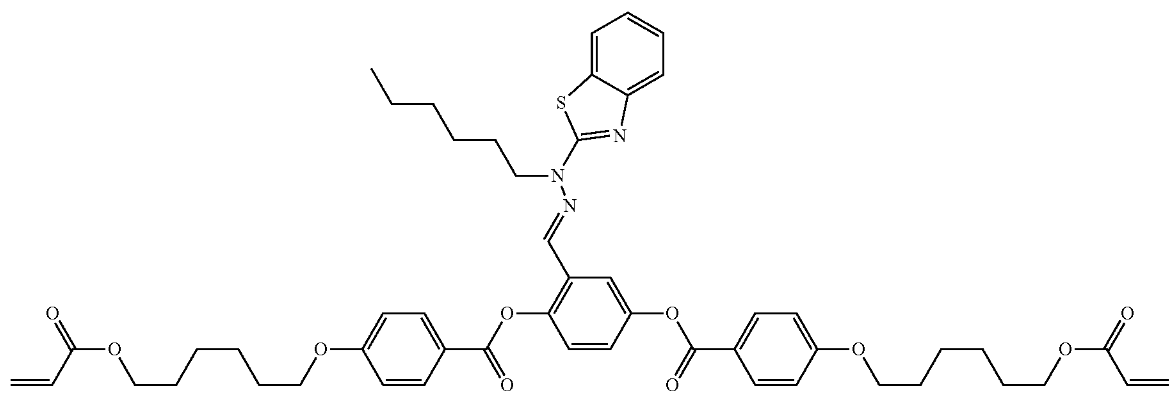

(I-3)

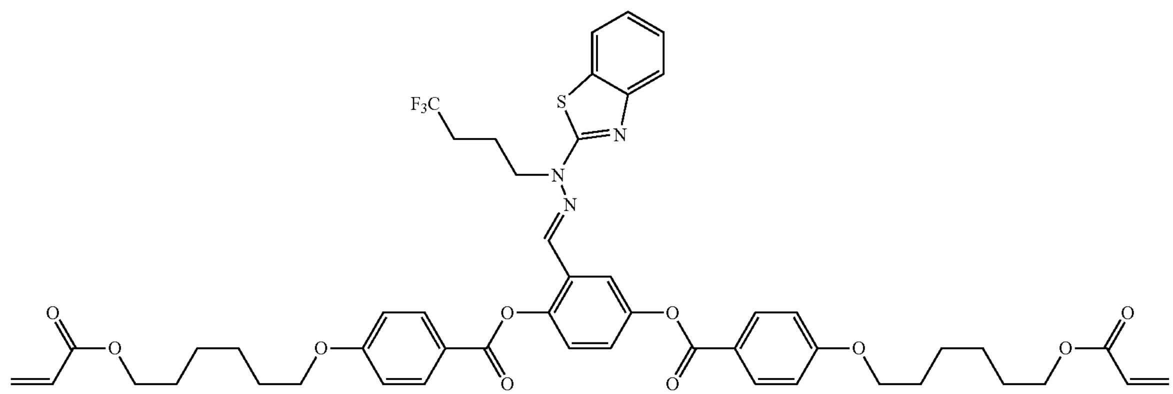

-continued (I-4)

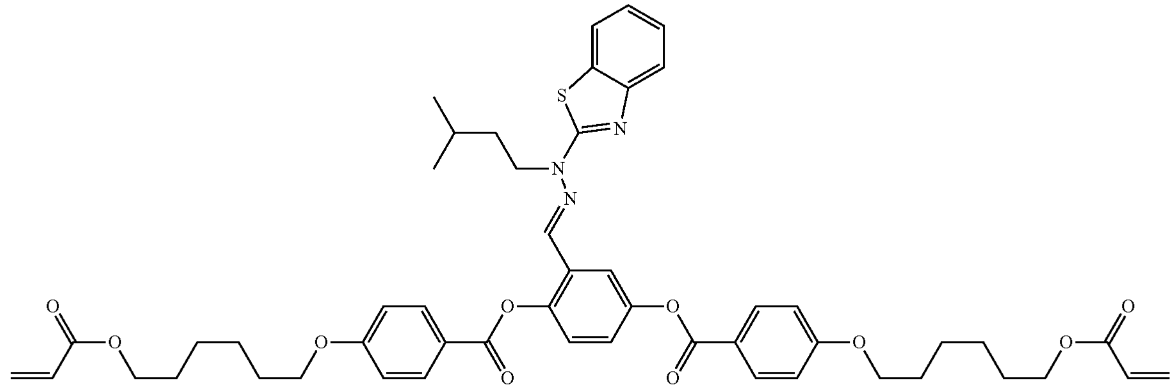

In the same manner as described above, the compound represented by formula (C-1R) prepared in Comparative Example 1, the compound represented by formula (C-3R) prepared in Comparative Example 3, and the compound represented by formula (C-4R) prepared in Comparative Example 4 were used to respectively produce compounds represented by formula (I-2R), formula (I-3R), and formula (I-4R) below.

[Chem. 47]

(I-2R)

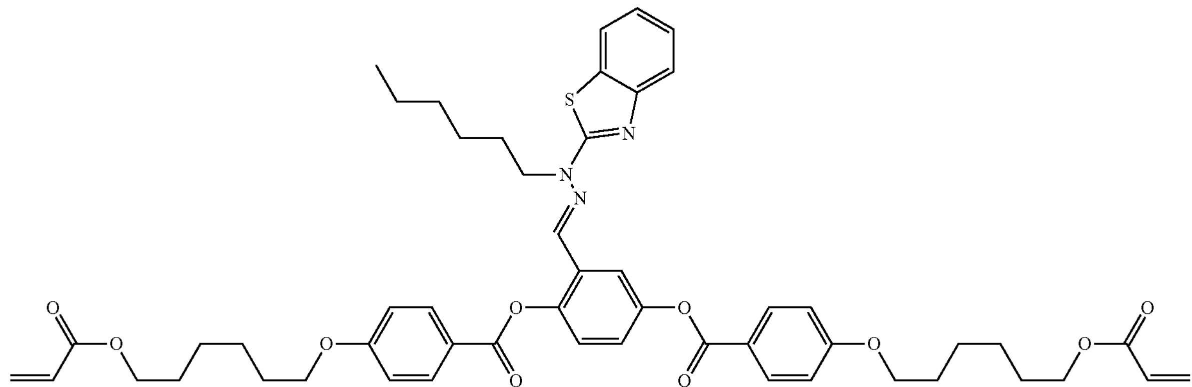

(I-3R)

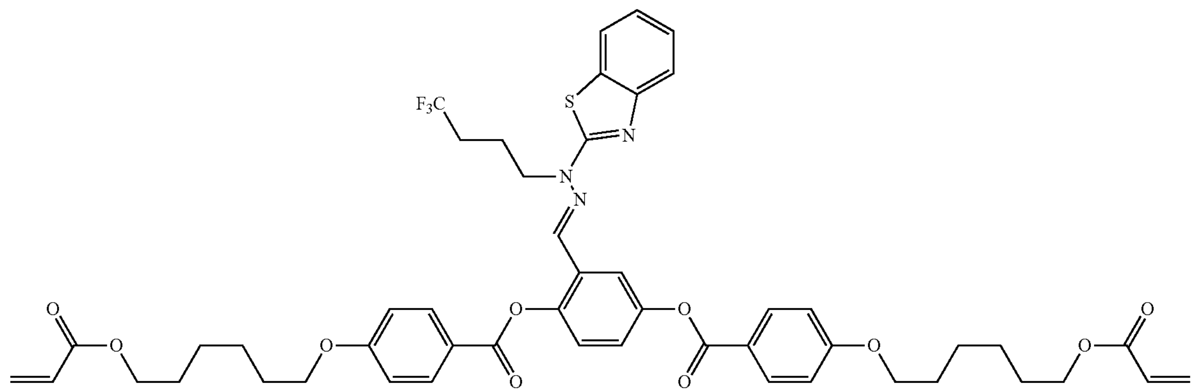

-continued
(I-4R)
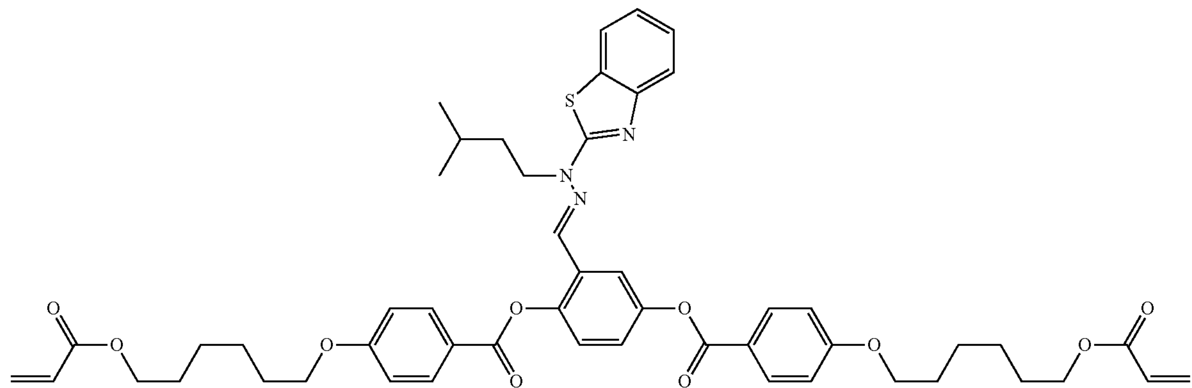
(Example 13) Production of Compound Represented by Formula (I-5)

[Chem. 48]
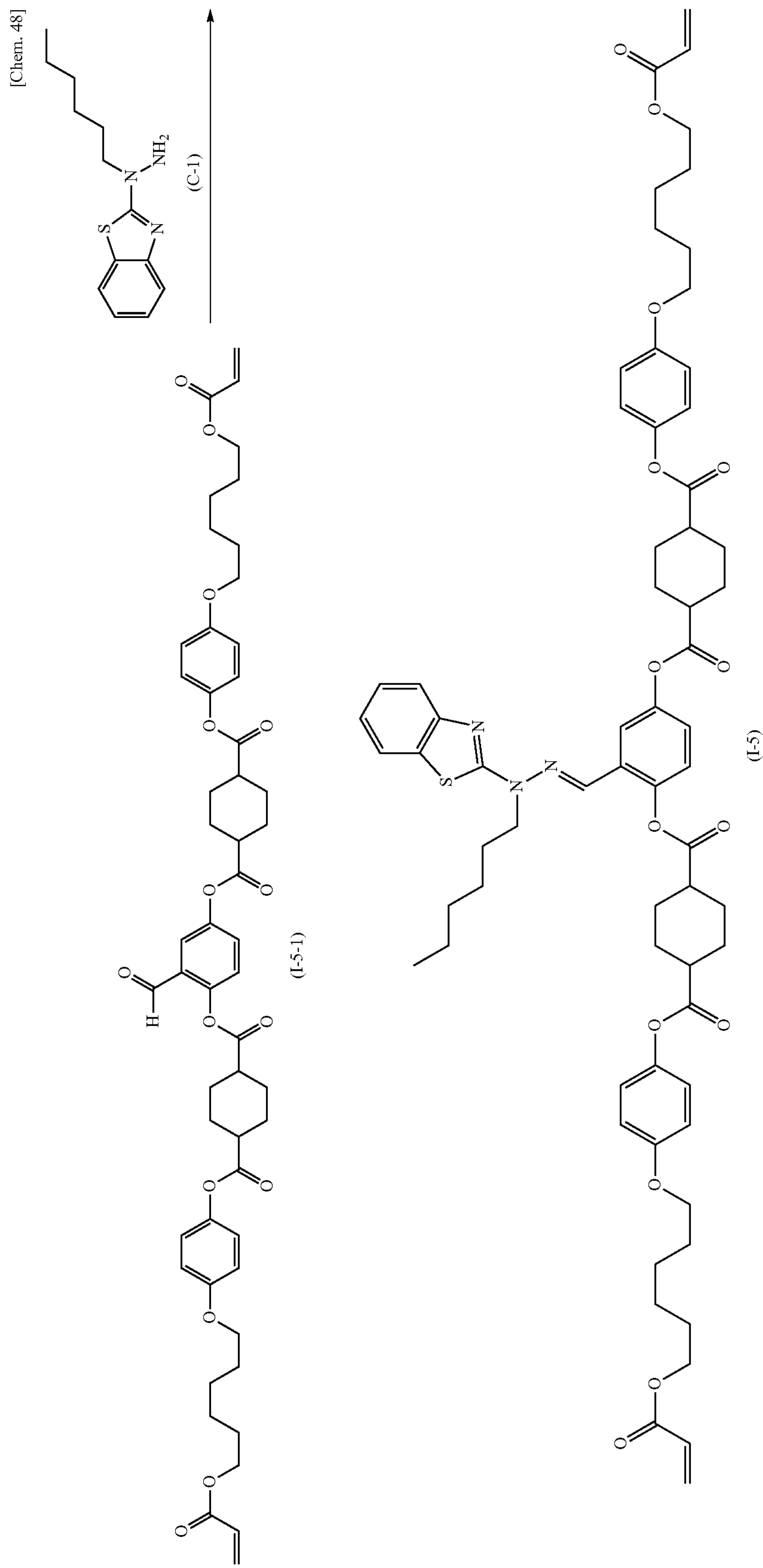

A compound represented by formula (I-5-1) was produced by the method described in International Publication No. WO 2014/010325 A1. Into a reactor purged with nitrogen, 3.0 g of a compound represented by formula (I-5-1), 0.8 g of the compound represented by formula (C-*i*) prepared in Example 1, 0.5 g of (±)-10-camphorsulfonic acid, 30 mL of tetrahydrofuran, and 15 mL of ethanol were added, followed by heating and stirring at 50° C. After the solvent was distilled away, methanol was added, and the precipitated solid was filtered. Purification by column chromatography (silica gel, dichloromethane) and recrystallization (dichloromethane/methanol) was performed to obtain 2.6 g of a compound represented by formula (I-5).

(Comparative Example 8) Production of Compound Represented by Formula (I-5R)

[Chem. 49]

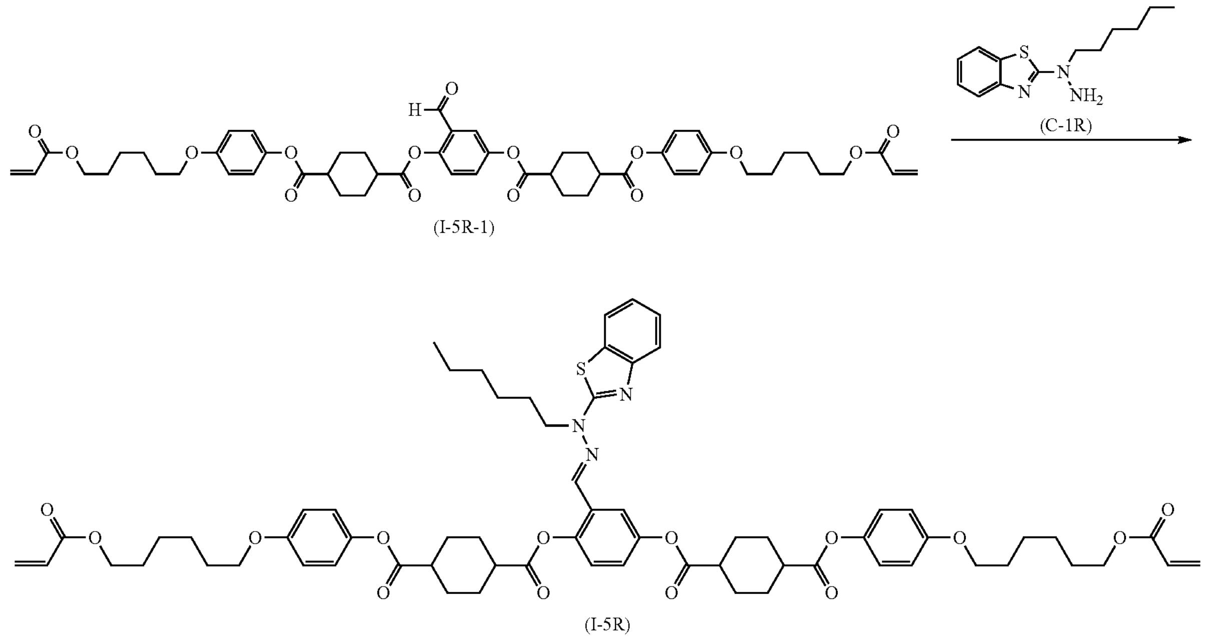

A compound represented by formula (I-5R) was produced by the same method as in Example 13 by using the compound represented by formula (C-1R) prepared in Comparative Example 1.

In the same manner as described above, the compound represented by formula (C-5) prepared in Example 5, the compound represented by formula (C-6) prepared in Example 6, and the compound represented by formula (C-3) prepared in Example 3 were used to respectively produce compounds represented by formula (I-6), formula (I-7), and formula (I-8) below.

[Chem. 50]

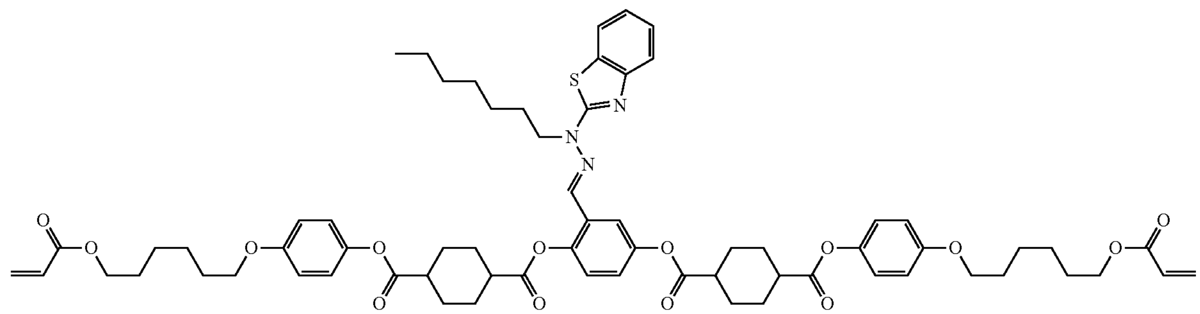

-continued (I-7)

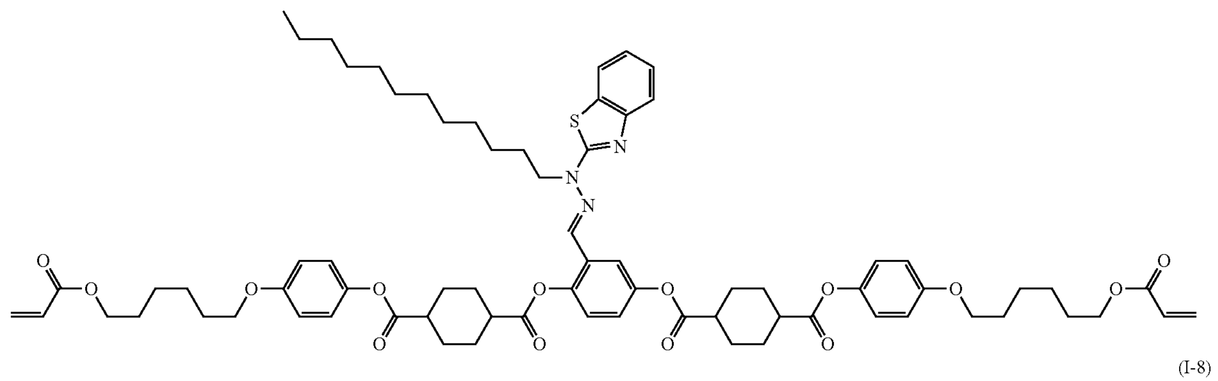

(I-8)

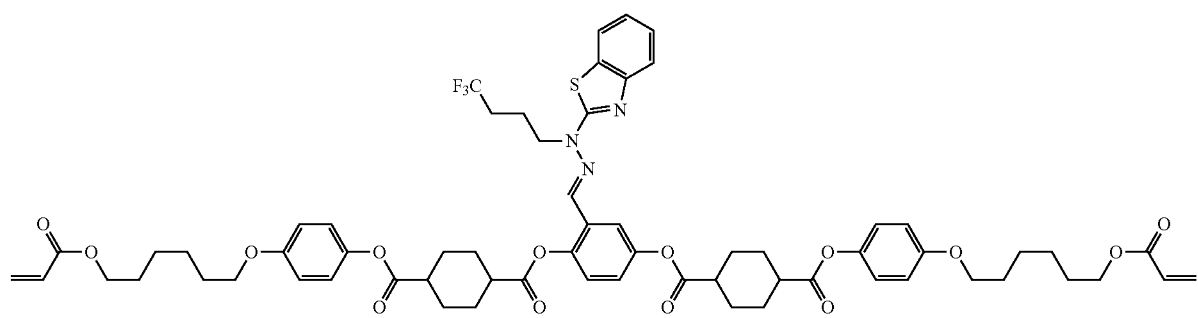

In the same manner as described above, the compound represented by formula (C-5R) prepared in Comparative Example 5, the compound represented by formula (C-6R) prepared in Comparative Example 6, and the compound represented by formula (C-3R) prepared in Comparative Example 3 were used to respectively produce compounds represented by formula (I-6R), formula (I-7R), and formula (I-8R) below.

[Chem. 51]

(I-6R)

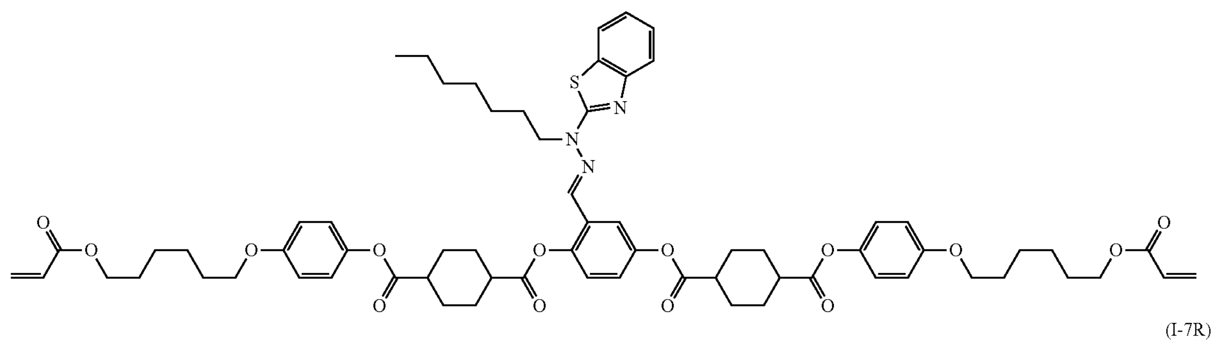

(I-7R)

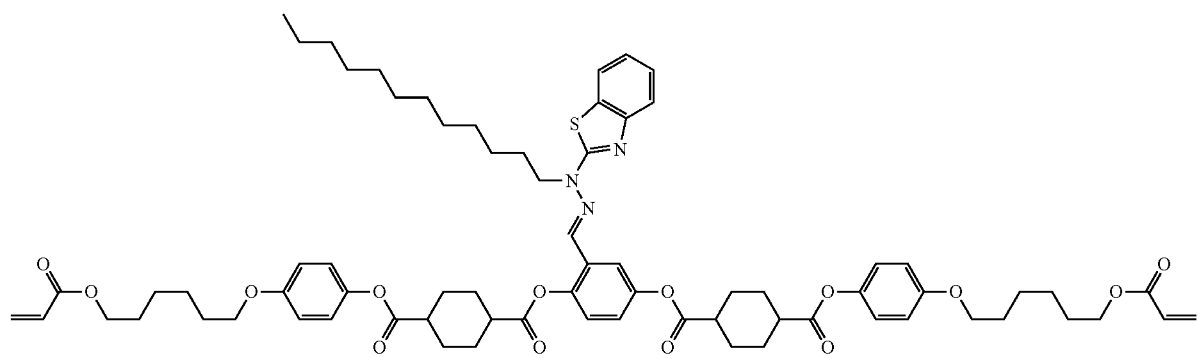

-continued
(I-8R)
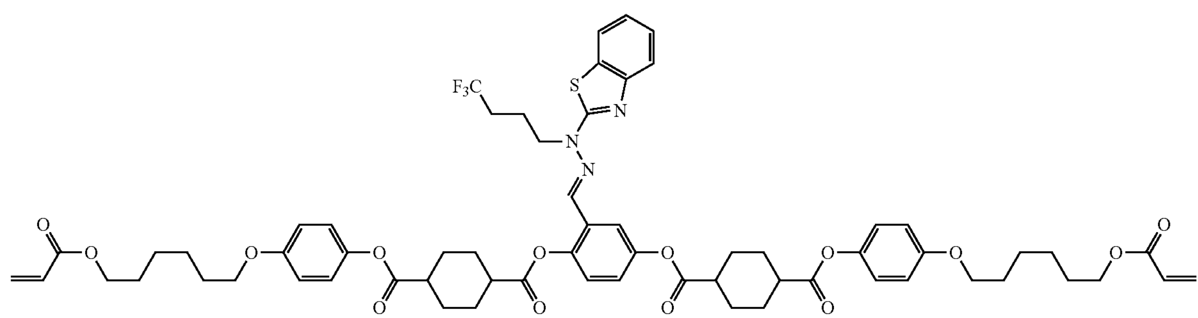
(Example 14) Production of Compound Represented by Formula (I-9)

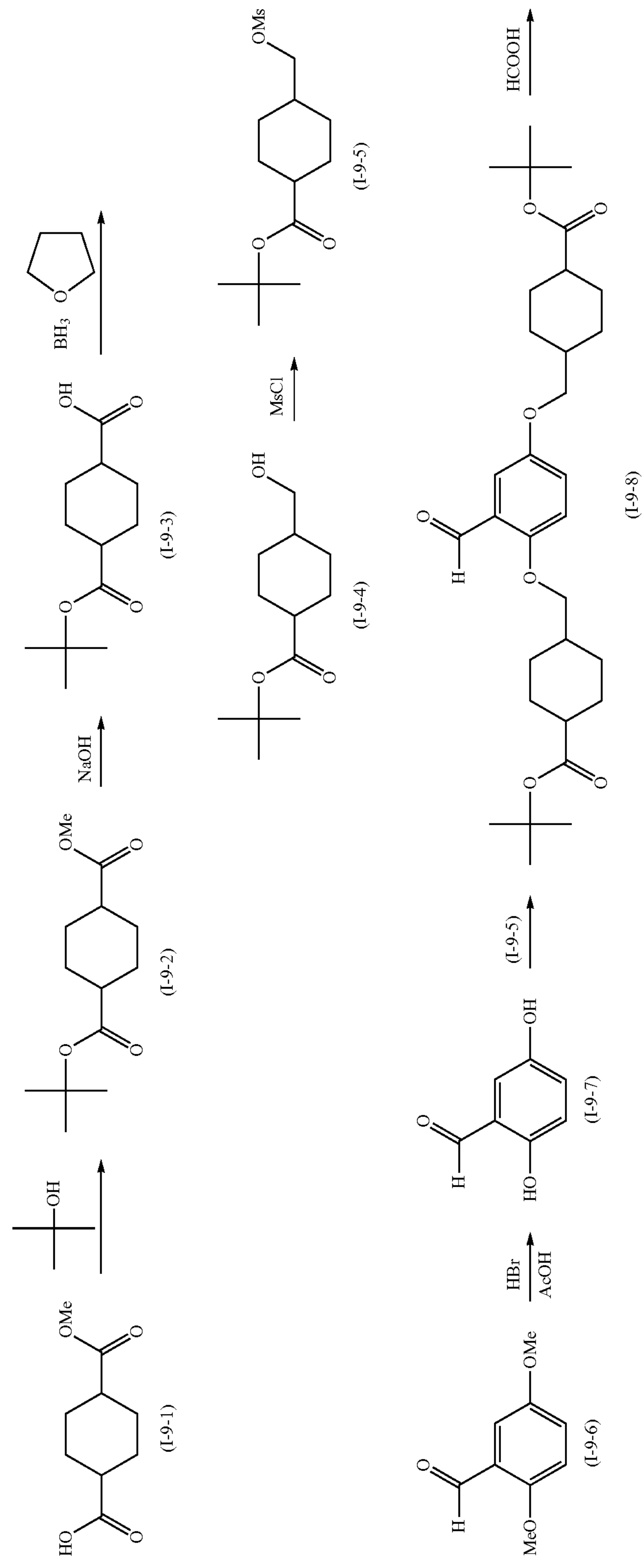
[Chem. 52]
(I-9-1)
(I-9-2)
NaOH
(I-9-3)
BH3
(I-9-4)
MsCl
(I-9-5)
(I-9-6)
HBr
AcOH
(I-9-7)
(I-9-5)
(I-9-8)
HCOOH -continued
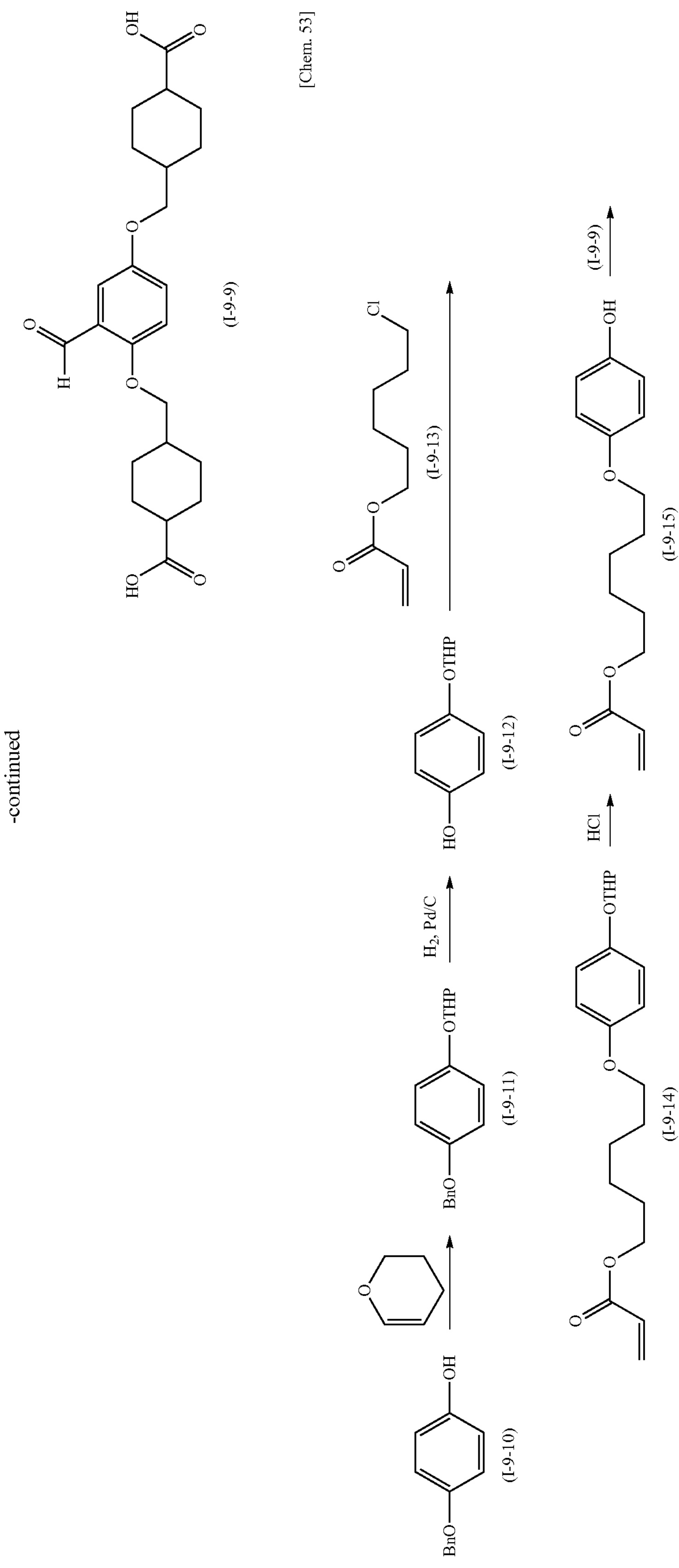

-continued
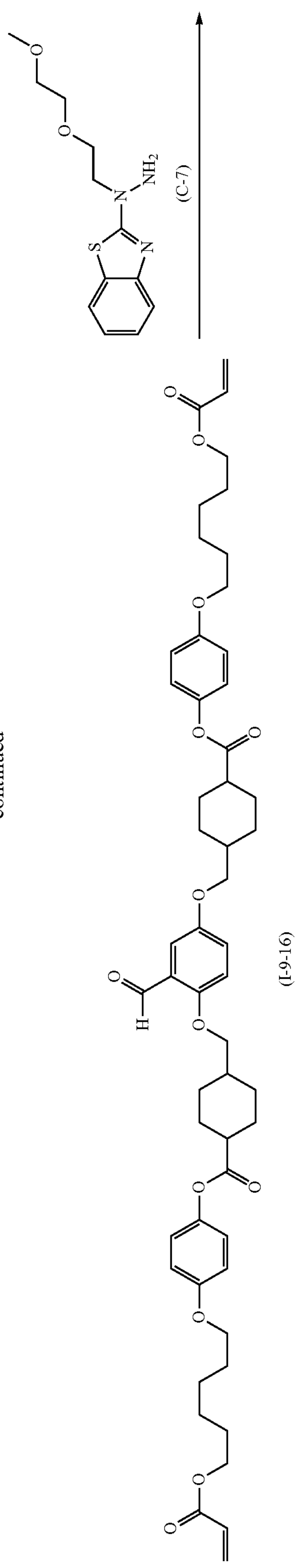
(I-9-16)
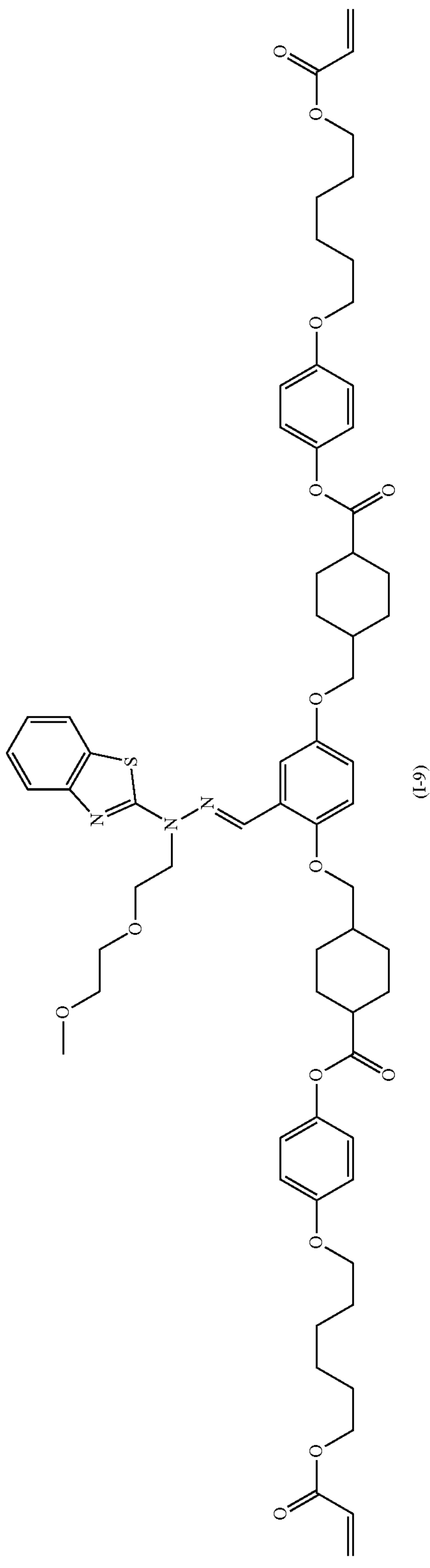
(I-9)

In a nitrogen atmosphere, 20.0 g of a compound represented by formula (I-9-1), 9.6 g of tert-butyl alcohol, 0.7 g of 4-dimethylaminopyridine, and 160 mL of dichloromethane were added into a reactor. While the mixture was being cooled over ice, 16.3 g of diisopropylcarbodiimide was added dropwise, followed by stirring at room temperature for 8 hours. The precipitates were removed by filtration, and were washed with a 5% hydrochloric acid and brine. Purification was performed by column chromatography (silica gel, dichloromethane/hexane) so as to obtain 24.7 g of a compound represented by formula (I-9-2).

Into a reactor, 24.7 g of a compound represented by formula (I-9-2), 200 mL of methanol, and 33 mL of a 25% aqueous sodium hydroxide solution were added, followed by stirring at room temperature for 8 hours. After neutralization with a 5% hydrochloric acid, the mixture was extracted with ethyl acetate and dried over sodium sulfate so as to obtain 22.1 g of a compound represented by formula (I-9-3).

In a nitrogen atmosphere, 20.0 g of a compound represented by formula (I-9-3) and 120 mL of tetrahydrofuran were added into a reactor. While the mixture was being cooled over ice, 105 mL of a borane-tetrahydrofuran complex (1 mol/L) was added dropwise, followed by stirring for 2 hours. After dropwise addition of 100 mL of a 5% hydrochloric acid, a liquid separation process was performed by using 200 mL of ethyl acetate. After drying over sodium sulfate, the solvent was distilled away so as to obtain 16.9 g of a compound represented by formula (I-9-4).

In a nitrogen atmosphere, 16.9 g of a compound represented by formula (I-9-4), 7.5 g of pyridine, and 100 mL of dichloromethane were added into a reactor. While the mixture was being cooled over ice, 10.8 g of methanesulfonyl chloride was added dropwise, followed by stirring at room temperature for 24 hours. After the resulting mixture was poured into a 5% hydrochloric acid, a liquid separation process was performed. Purification was performed by column chromatography (silica gel, dichloromethane) so as to obtain 20.7 g of a compound represented by formula (I-9-5).

In a nitrogen atmosphere, 20.0 g of a compound represented by formula (I-9-6), 60 mL of a 48% hydrobromic acid, and 60 mL of acetic acid were added, and the resulting mixture was refluxed under heating for 6 hours. After cooling, a liquid separation process was performed by using 200 mL of ethyl acetate. Purification was performed by column chromatography (alumina, ethyl acetate) so as to obtain 14.6 g of a compound represented by formula (I-9-7).

In a nitrogen atmosphere, 1.0 g of a compound represented by formula (I-9-7), 4.2 g of a compound represented by formula (I-9-5), 3.8 g of potassium phosphate, and 20 mL of N,N-dimethylformamide were added into a reactor, and the resulting mixture was heated and stirred at 90° C. for 8 hours. After the reaction solution was poured into 100 mL of water, solid precipitates were filtered, and washed with water. Purification by column chromatography (silica gel, dichloromethane) and recrystallization (dichloromethane/methanol) was performed to obtain 3.1 g of a compound represented by formula (I-9-8).

In a nitrogen atmosphere, 3.1 g of a compound represented by formula (I-9-8), 30 mL of dichloromethane, and 30 mL of formic acid were added into a reactor, followed by stirring under heating at 40° C. for 8 hours. After the solvent was distilled away, 30 mL of diisopropyl ether was added, followed by stirring and filtration of precipitates. The obtained solid was washed with diisopropyl ether so as to obtain 2.2 g of a compound represented by formula (I-9-9).

Into a reactor, 10.0 g of a compound represented by formula (I-9-10), 0.7 g of pyridinium p-toluenesulfonate, and 100 mL of dichloromethane were added. While the mixture was being cooled over ice, 4.6 g of 3,4-dihydro-2H-pyran was added dropwise, followed by stirring at room temperature for 7 hours. After the mixture was washed with a 5% aqueous sodium hydrogen carbonate solution and brine, purification was performed by column chromatography (alumina, dichloromethane) so as to obtain 13.5 g of a compound represented by formula (I-9-9).

Into a pressure-proof container, 13.5 g of a compound represented by formula (I-9-9), 0.1 g of a 5% palladium carbon, 50 mL of tetrahydrofuran, and 50 mL of ethanol were added. The mixture was heated and stirred at 50° C. at a hydrogen pressure of 0.5 MPa for 8 hours. After the catalyst was filtered, the solvent was distilled away so as to obtain 8.8 g of a compound represented by formula (I-9-12).

Into a reactor, 15.0 g of a compound represented by formula (I-9-12), 17.7 g of a compound represented by formula (I-9-13), 16.0 g of potassium carbonate, and 90 mL of N,N-dimethylformamide were added, and the resulting mixture was heated and stirred at 90° C. for 20 hours. Then 150 mL of dichloromethane was added to perform a liquid separation process. Purification was performed by column chromatography (silica gel, dichloromethane) so as to obtain 24.2 g of a compound represented by formula (I-9-14).

Into a reactor, 24.2 g of a compound represented by formula (I-9-14), 80 mL of tetrahydrofuran, and 80 mL of methanol were added. Thereto, 1 mL of concentrated hydrochloric acid was added, followed by stirring at room temperature for 10 hours. After the solvent was distilled away, a liquid separation process was performed by using 150 mL of ethyl acetate. Purification was performed by column chromatography (alumina, ethyl acetate) and recrystallization (ethyl acetate/hexane) so as to obtain 17.4 g of a compound represented by formula (I-9-15).

In a nitrogen atmosphere, 1.9 g of a compound represented by formula (I-9-9), 2.4 g of a compound represented by formula (I-9-15), 0.06 g of N,N-dimethylaminopyridine, and 20 mL of dichloromethane were added into a reactor. While the mixture was being cooled over ice, 2.2 g of 1-ethyl-3-(3-dimethylaminopropyl)carbodiimide hydrochloride was added, followed by stirring at room temperature for 8 hours. The reaction solution was washed with a 5% hydrochloric acid and brine. Purification by column chromatography (silica gel, dichloromethane) and recrystallization (dichloromethane/methanol) was performed to obtain 3.3 g of a compound represented by formula (I-9-16).

Into a reactor purged with nitrogen, 3.3 g of a compound represented by formula (I-9-16), 1.0 g of the compound represented by formula (C-7) prepared in Example 7, 0.5 g of (±)-10-camphorsulfonic acid, 30 mL of tetrahydrofuran, and 15 mL of ethanol were added, followed by heating and stirring at 50° C. for 8 hours. After the solvent was distilled away, methanol was added to perform crystallization, and the crystals were filtered. Purification by column chromatography (silica gel, dichloromethane) and recrystallization (dichloromethane/methanol) was performed to obtain 2.9 g of a compound represented by formula (I-9).

Transition temperature (temperature elevation: 5° C./minute): C 85 N 128 I $^1$H NMR ($CDCl_3$) δ 1.22-1.28 (m, 4H), 1.44-1.47 (m, 8H), 1.60-1.82 (m, 12H), 1.90 (m, 2H), 2.07 (t, 4H), 2.24 (d, 4H), 2.53 (m, 2H), 3.30 (s, 3H), 3.50 (t, 2H), 3.66 (t, 2H), 3.85-3.89 (m, 6H), 3.93 (t, 4H), 4.17 (t, 4H), 4.53 (t, 2H), 5.82 (d, 2H), 6.13 (q, 2H), 6.40 (d, 2H), 6.83-6.90 (m, 6H), 6.95-6.98 (m, 4H), 7.14 (t, 1H), 7.32 (t, 1H), 7.52 (t, 1H), 7.67 (t, 2H), 8.33 (s, 1H) ppm.

(Example 15) Production of Compound Represented by Formula (I-10)

[Chem. 54]
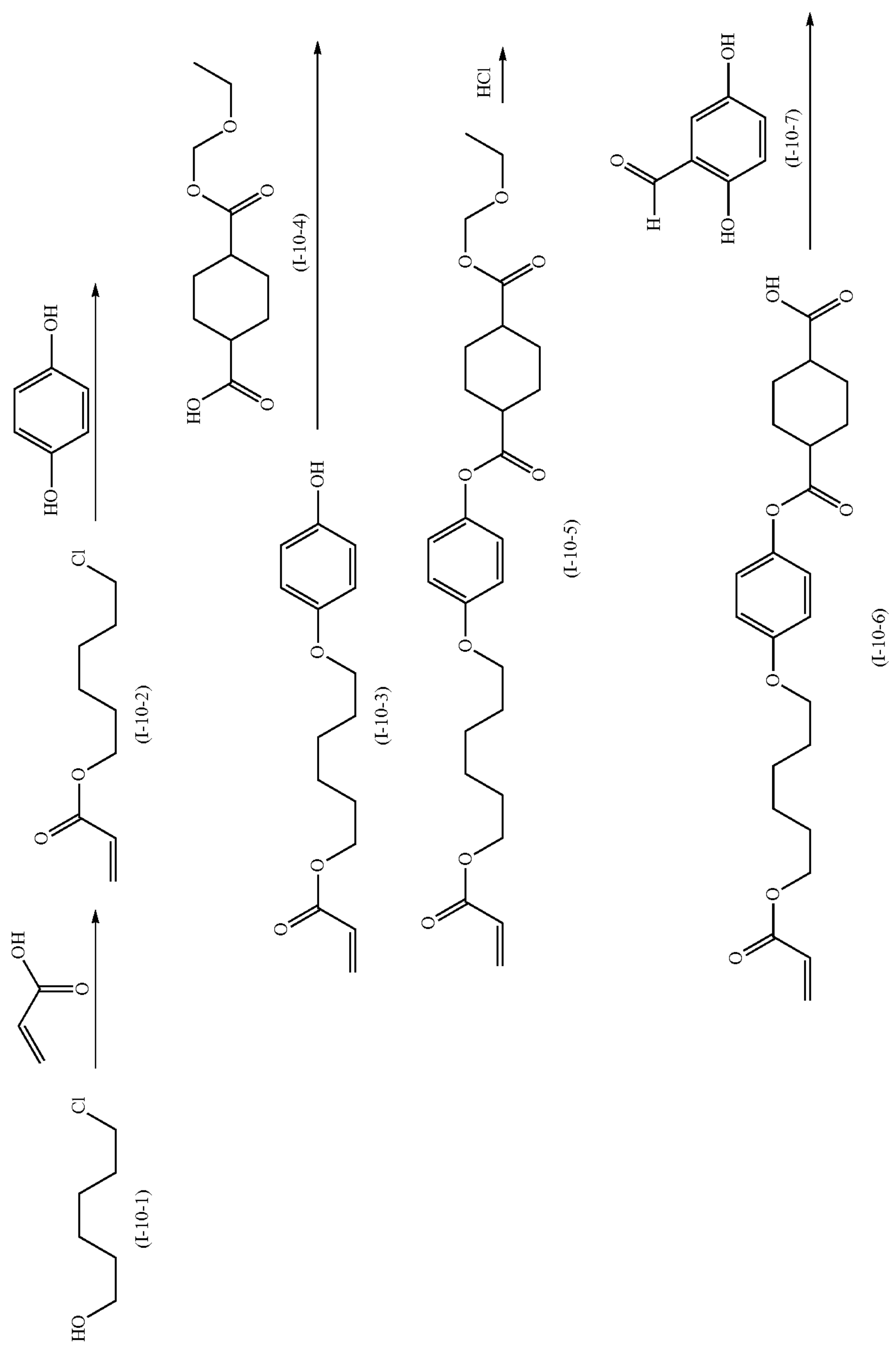

-continued
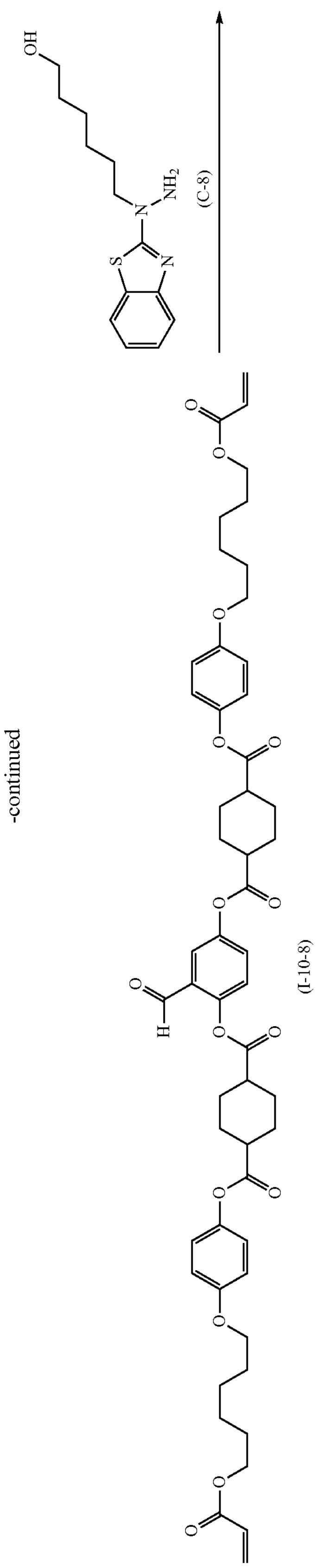
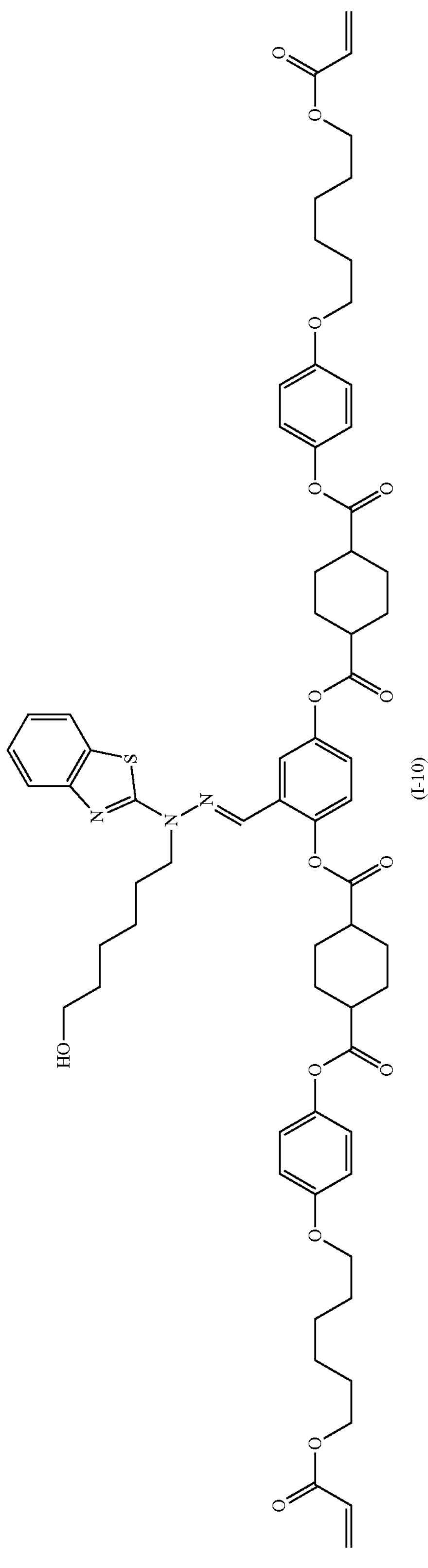

Into a reactor equipped with a Dean-Stark apparatus, 20.0 g of a compound represented by formula (I-10-1), 15.8 g of acrylic acid, 2.8 g of p-toluenesulfonic acid monohydrate, and 150 mL of toluene were added, and the mixture was refluxed under heating for 8 hours while performing dehydration. After cooling, the mixture was washed with a 5% aqueous sodium hydrogen carbonate solution and brine. Purification was performed by column chromatography (silica gel, toluene) so as to obtain 25.1 g of a compound represented by formula (I-10-2).

Into a reactor, 10.0 g of a compound represented by formula (I-10-2), 28.9 g of hydroquinone, 18.1 g of potassium carbonate, and 80 mL of acetone were added, and the resulting mixture was refluxed under heating for 6 hours. After cooling, the solid matter was filtered, and the solvent was distilled away. Thereto, 150 mL of ethyl acetate was added, and the mixture was washed with a 5% hydrochloric acid and brine. Purification was performed by column chromatography (silica gel, ethyl acetate) and recrystallization (ethyl acetate/hexane) so as to obtain 9.7 g of a compound represented by formula (I-10-3).

A compound represented by formula (I-10-4) was produced by the method described in International Publication No. WO 2011/068138 A1. In a nitrogen atmosphere, 5.0 g of a compound represented by formula (I-10-3), 4.4 g of a compound represented by formula (I-10-4), 0.2 g of N,N-dimethylaminopyridine, and 40 mL of dichloromethane were added into a reactor. While the mixture was being cooled over ice, 2.9 g of diisopropylcarbodiimide was added dropwise, followed by stirring. The precipitates were filtered, and the filtrate was washed with a 5% hydrochloric acid and brine. Purification by column chromatography (alumina, dichloromethane) and recrystallization (dichloromethane/methanol) was performed to obtain 7.2 g of a compound represented by formula (I-10-5).

Into a reactor, 7.2 g of a compound represented by formula (I-10-5), 30 mL of tetrahydrofuran, 30 mL of methanol, and 1 mL of concentrated hydrochloric acid were added, followed by stirring at room temperature for 7 hours. The resulting mixture was diluted with 150 mL of ethyl acetate, and washed with brine. Purification was performed by column chromatography (alumina, ethyl acetate) and dispersion washing (hexane) so as to obtain 6.0 g of a compound represented by formula (I-10-6).

In a nitrogen atmosphere, 4.0 g of a compound represented by formula (I-10-6), 0.7 g of a compound represented by formula (I-10-7), 0.1 g of N,N-dimethylaminopyridine, and 40 mL of dichloromethane were added into a reactor. While the mixture was being cooled over ice, 1.5 g of diisopropylcarbodiimide was added dropwise, followed by stirring at room temperature for 8 hours. After the solid matter was filtered, and the filtrate was washed with a 5% hydrochloric acid and brine. Purification by column chromatography (silica gel, dichloromethane) and recrystallization (dichloromethane/methanol) was performed to obtain 3.3 g of a compound represented by formula (I-10-8).

In a nitrogen atmosphere, 3.3 g of a compound represented by formula (I-10-8), 0.9 g of the compound represented by formula (C-8) prepared in Example 8, 0.5 g of (±)-10-camphorsulfonic acid, 30 mL of tetrahydrofuran, and 15 mL of ethanol were added into a reactor, followed by heating and stirring at 50° C. After the solvent was distilled away, methanol was added to perform crystallization, and the crystals were filtered. Purification by column chromatography (silica gel, dichloromethane) and recrystallization (dichloromethane/methanol) was performed to obtain 2.3 g of a compound represented by formula (I-10).

LCMS: 1186 [M+1]

(Example 16) Production of Compound Represented by Formula (I-11)

[Chem. 55]
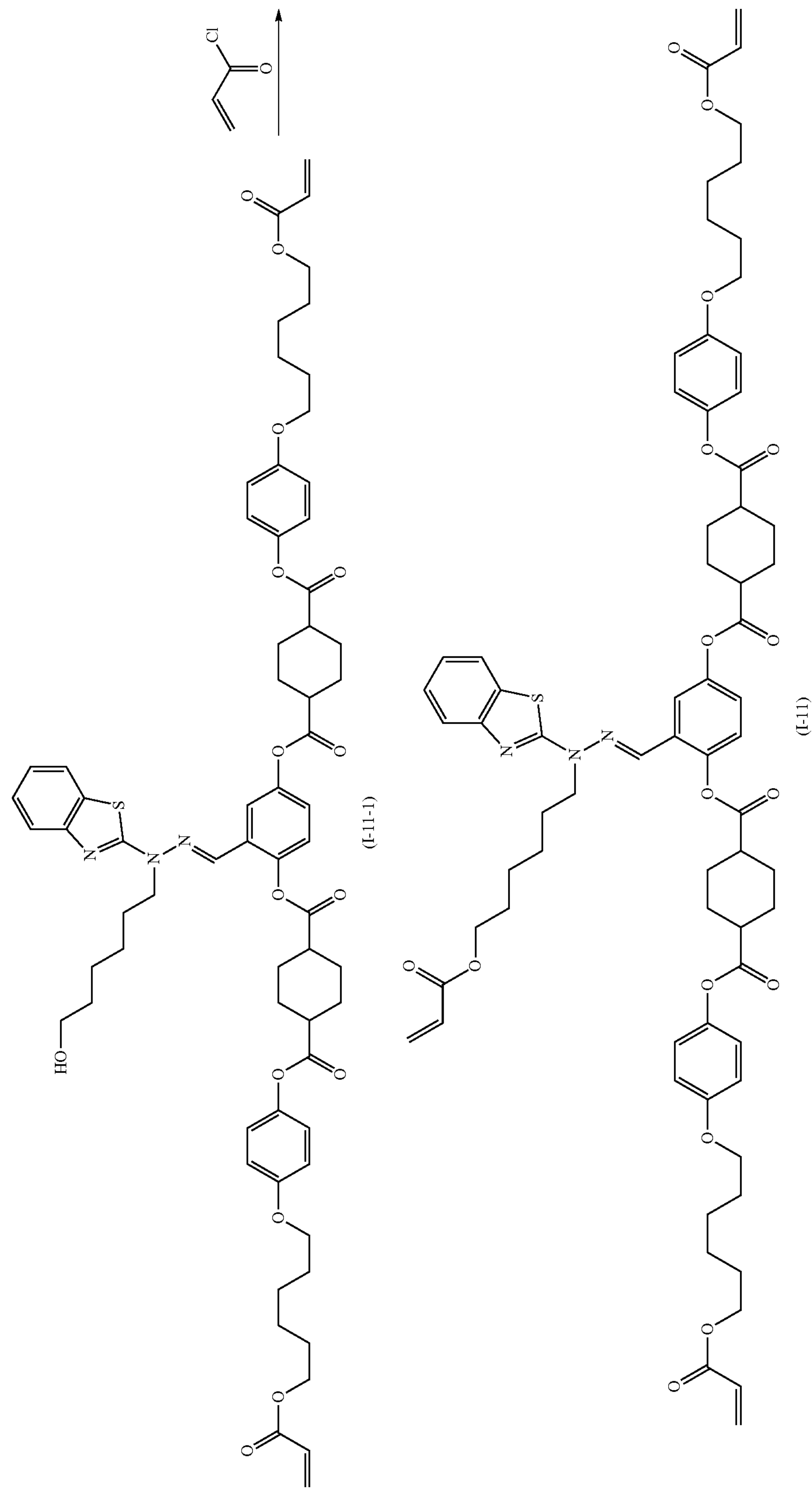

In a nitrogen atmosphere, 3.0 g of a compound represented by formula (I-11-1), 0.5 g of diisopropylethylamine, and 30 mL of dichloromethane were added into a reactor. While the mixture was being cooled over ice, 0.3 g of acryloyl chloride was added dropwise, followed by stirring at room temperature for 5 hours. After the mixture was washed with a 1% hydrochloric acid and brine, purification by column chromatography (silica gel, dichloromethane) and recrystallization (dichloromethane/methanol) was performed to obtain 2.2 g of a compound represented by formula (I-11).

$^1$H NMR ($CDCl_3$) δ 1.24 (m, 4H), 1.48-1.93 (m, 30H), 2.08 (t, 4H), 2.23 (m, 4H), 2.54 (m, 2H), 3.86 (dd, 4H), 3.94 (t, 4H), 4.17 (t, 4H), 4.53 (t, 2H), 4.65 (t, 2H), 5.82 (dd, 3H), 6.12 (dd, 3H), 6.40 (dd, 3H), 6.88 (m, 6H), 6.97 (dd, 4H), 7.16 (t, 1H), 7.34 (t, 1H), 7.54 (d, 1H), 7.66 (d, 1H), 7.70 (d, 1H), 8.36 (s, 1H) ppm.

LCMS: 1212 [M+1]

(Example 17) Production of Compound Represented by Formula (I-12)

[Chem. 56]

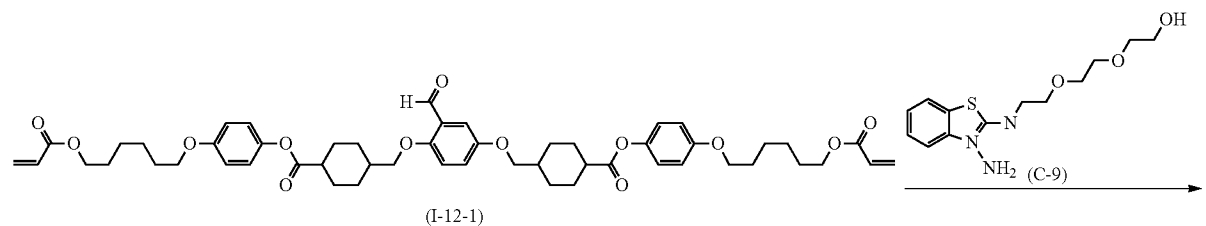

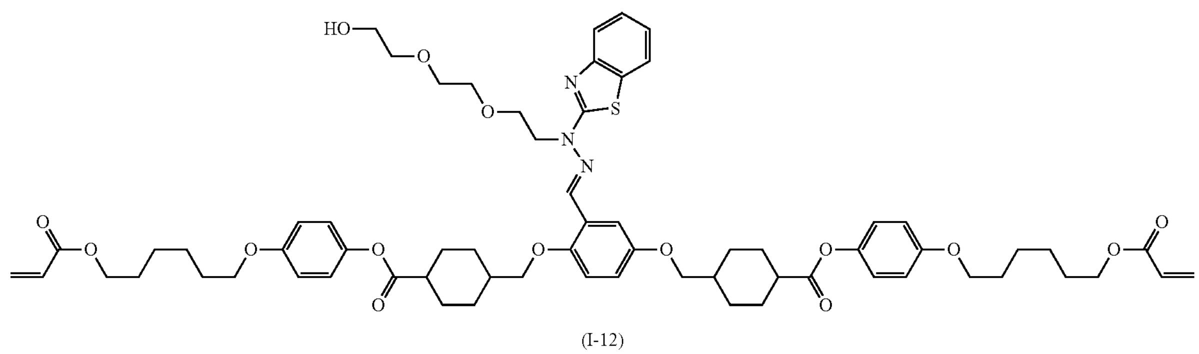

In a nitrogen atmosphere, 3.0 g of a compound represented by formula (I-12-1), 1.0 g of the compound represented by formula (C-9) prepared in Example 9, 0.5 g of (±)-10-camphorsulfonic acid, 30 mL of tetrahydrofuran, and 15 mL of ethanol were added into a reactor, followed by heating and stirring at 50° C. After the solvent was distilled away, methanol was added to perform crystallization, and the crystals were filtered. Purification by column chromatography (silica gel, dichloromethane) and recrystallization (dichloromethane/methanol) was performed to obtain 2.7 g of a compound represented by formula (I-12).

$^1$H NMR ($CDCl_3$) δ 1.07 (q, 2H), 1.24 (q, 2H), 1.47-1.90 (m, 24H), 2.09 (m, 4H), 2.22 (d, 2H), 2.39 (t, 1H), 2.53 (t, 1H), 3.56 (t, 2H), 3.60-3.66 (m, 4H), 3.73 (t, 2H), 3.74 (d, 2H), 3.85 (d, 2H), 3.90 (t, 2H), 3.94 (td, 4H), 4.00 (t, 2H), 4.17 (td, 4H), 5.82 (d, 2H), 6.13 (dd, 2H), 6.40 (d, 2H), 6.80-6.99 (m, 6H), 6.98 (d, 4H), 7.16 (t, 1H), 7.33 (t, 1H), 7.55 (m, 2H), 7.67 (d, 1H), 8.40 (s, 1H) ppm.

LCMS: 1190 [M+1]

(Example 18) Production of Compound Represented by Formula (I-13)

[Chem. 57]
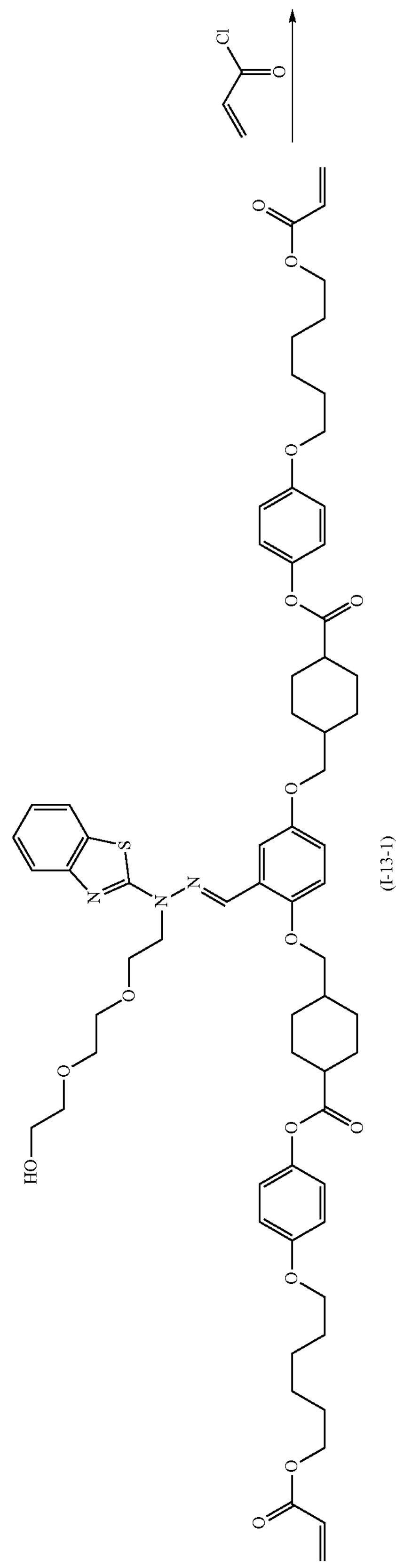
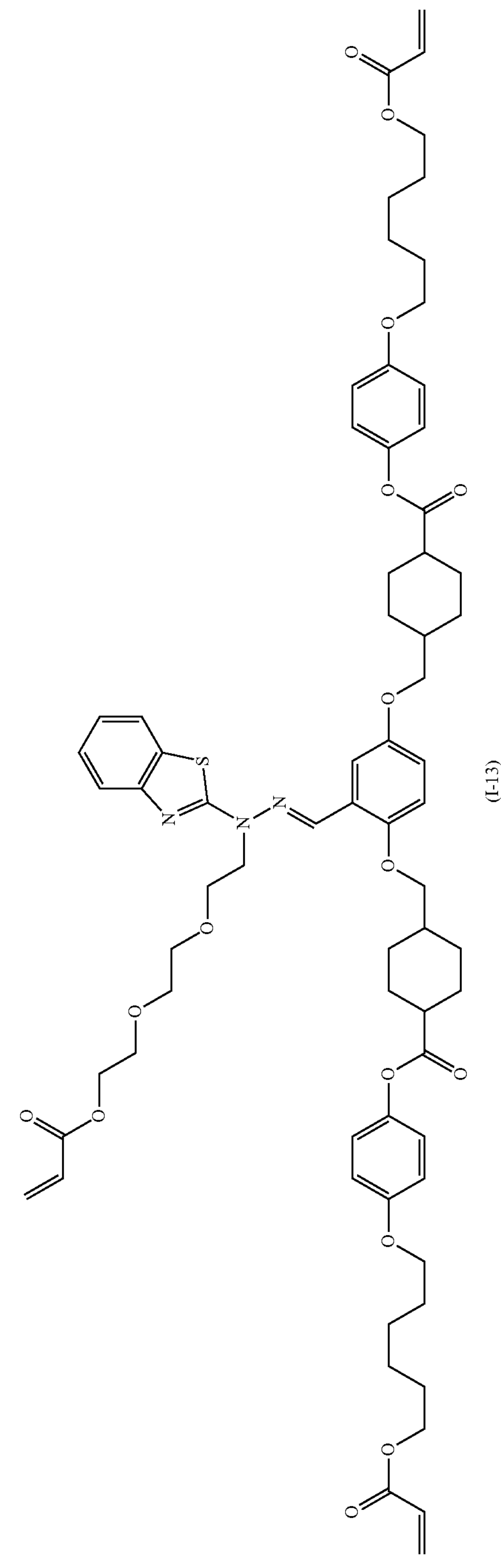

In a nitrogen atmosphere, 3.0 g of a compound represented by formula (I-13-1), 0.5 g of diisopropylethylamine, and 30 mL of dichloromethane were added into a reactor. While the mixture was being cooled over ice, 0.3 g of acryloyl chloride was added dropwise, followed by stirring at room temperature for 5 hours. After the mixture was washed with a 1% hydrochloric acid and brine, purification by column chromatography (silica gel, dichloromethane) and recrystallization (dichloromethane/methanol) was performed to obtain 2.6 g of a compound represented by formula (I-13).

Transition temperature (temperature elevation: 5° C./minute): C 71 N 115 I $^{1}$H NMR ($CDCl_3$) δ 1.19-1.29 (m, 4H), 1.41-1.82 (m, 22H), 1.91 (m, 2H), 2.08 (m, 4H), 2.24 (m, 4H), 2.53 (m, 2H), 3.62 (m, 3H), 3.67 (m, 2H), 3.84-3.90 (m, 5H), 3.94 (t, 4H), 4.15-4.19 (m, 6H), 4.53 (t, 2H), 5.76 (dd, 1H), 5.82 (dd, 2H), 6.08 (dd, 1H), 6.12 (dd, 2H), 6.37 (dd, 1H), 6.40 (dd, 2H), 6.84-6.90 (m, 6H), 6.95-6.98 (m, 4H), 7.14 (t, 1H), 7.32 (t, 1H), 7.53 (d, 1H), 7.65 (d, 1H), 7.69 (d, 1H), 8.34 (s, 1H) ppm.

LCMS: 1244 [M+11]

(Example 19) Production of Compound Represented by Formula (I-14)

[Chem. 58]
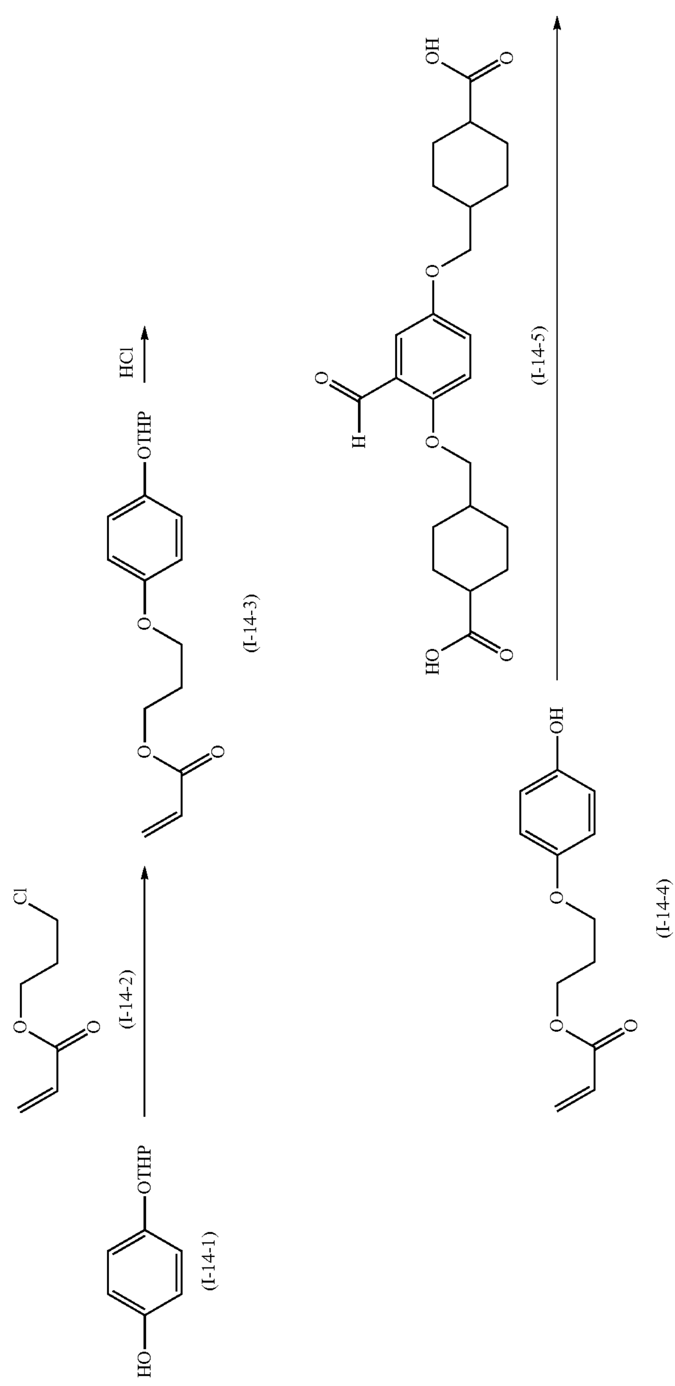

-continued
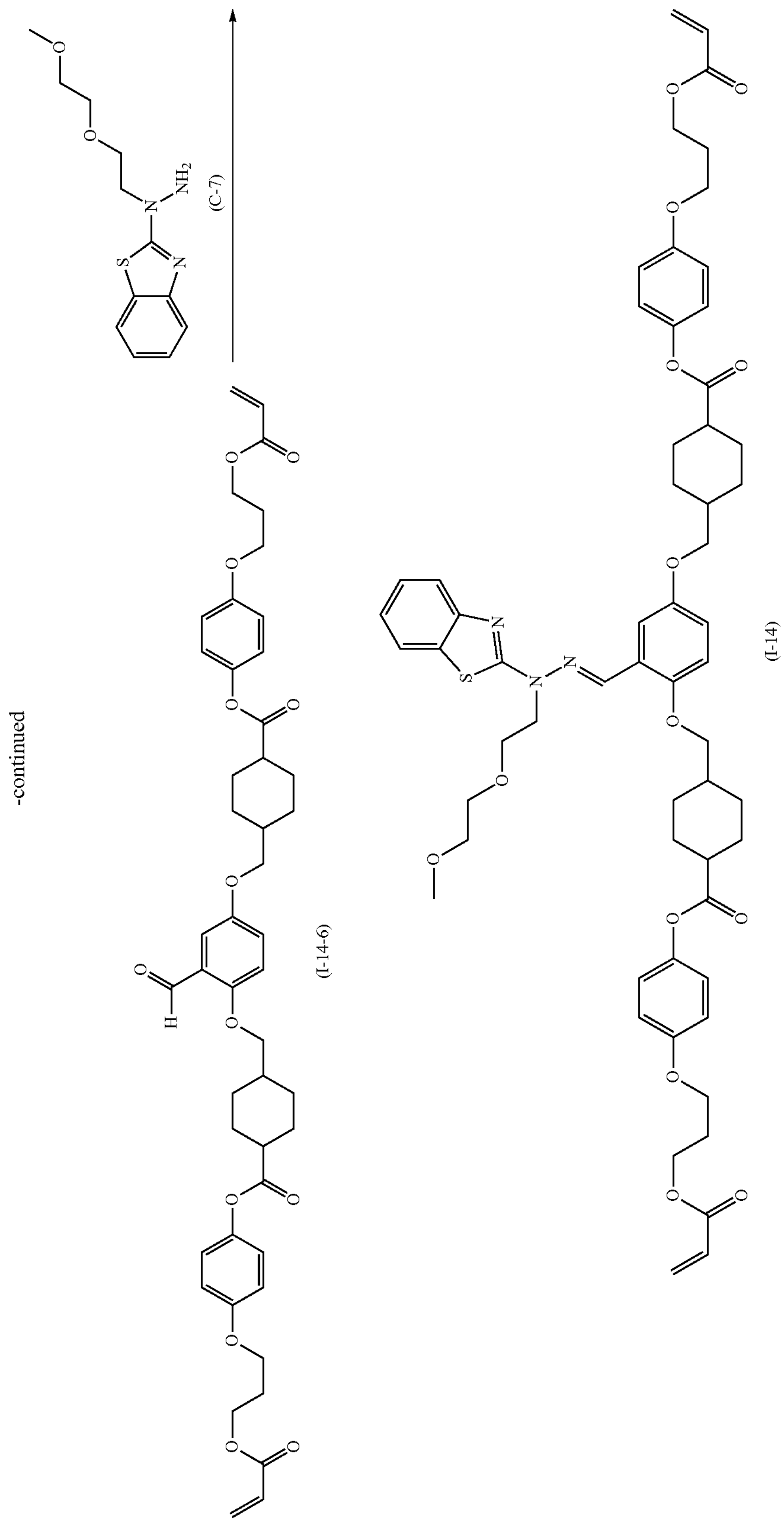

A compound represented by formula (I-14) was produced by the same method as in Example 14 by using the compound represented by formula (C-7) prepared in Example 7 except that the compound represented by formula (I-9-13) was replaced by the compound represented by formula (I-14-2). Transition temperature (temperature elevation: 5° C./minute): C 89-95 N 145 I $^1$H NMR ($CDCl_3$) δ 1.24 (m, 4H), 1.65 (m, 4H), 1.91 (m, 2H), 2.05-2.25 (m, 12H), 2.55 (m, 2H), 3.30 (s, 3H), 3.51 (m, 2H), 3.67 (m, 2H), 3.84-3.89 (m, 6H), 4.05 (t, 4H), 4.36 (t, 4H), 4.54 (t, 2H), 5.84 (dd, 2H), 6.13 (dd, 2H), 6.41 (dd, 2H), 6.84-6.89 (m, 6H), 6.97-7.00 (m, 4H), 7.14 (t, 1H), 7.33 (t, 1H), 7.52 (d, 1H), 7.67 (dd, 2H), 8.34 (s, 1H ppm.

(Example 20) Production of Compound Represented by Formula (I-15)

resulting mixture was diluted with ethyl acetate, and washed with hydrochloric acid and brine. Purification was performed by column chromatography (silica gel, hexane/ethyl acetate) so as to obtain 5.36 g of a compound represented by formula (I-15-2).

In a nitrogen atmosphere, 2.0 g of a compound represented by formula (I-15-2), 3.4 g of a compound represented by formula (I-15-3), 0.4 g of N,N-dimethylaminopyridine, and 30 mL of dichloromethane were added into a reactor. While the mixture was being cooled over ice, 1.3 g of diisopropylcarbodiimide was added dropwise, followed by stirring at room temperature. The precipitates were filtered, and the filtrate was washed with a 5% hydrochloric acid, water, and brine. Purification by column chromatography (silica gel, dichloromethane) and recrystallization (dichloromethane/methanol) was performed to obtain 3.7 g of a compound represented by formula (I-15-4).

[Chem. 59]

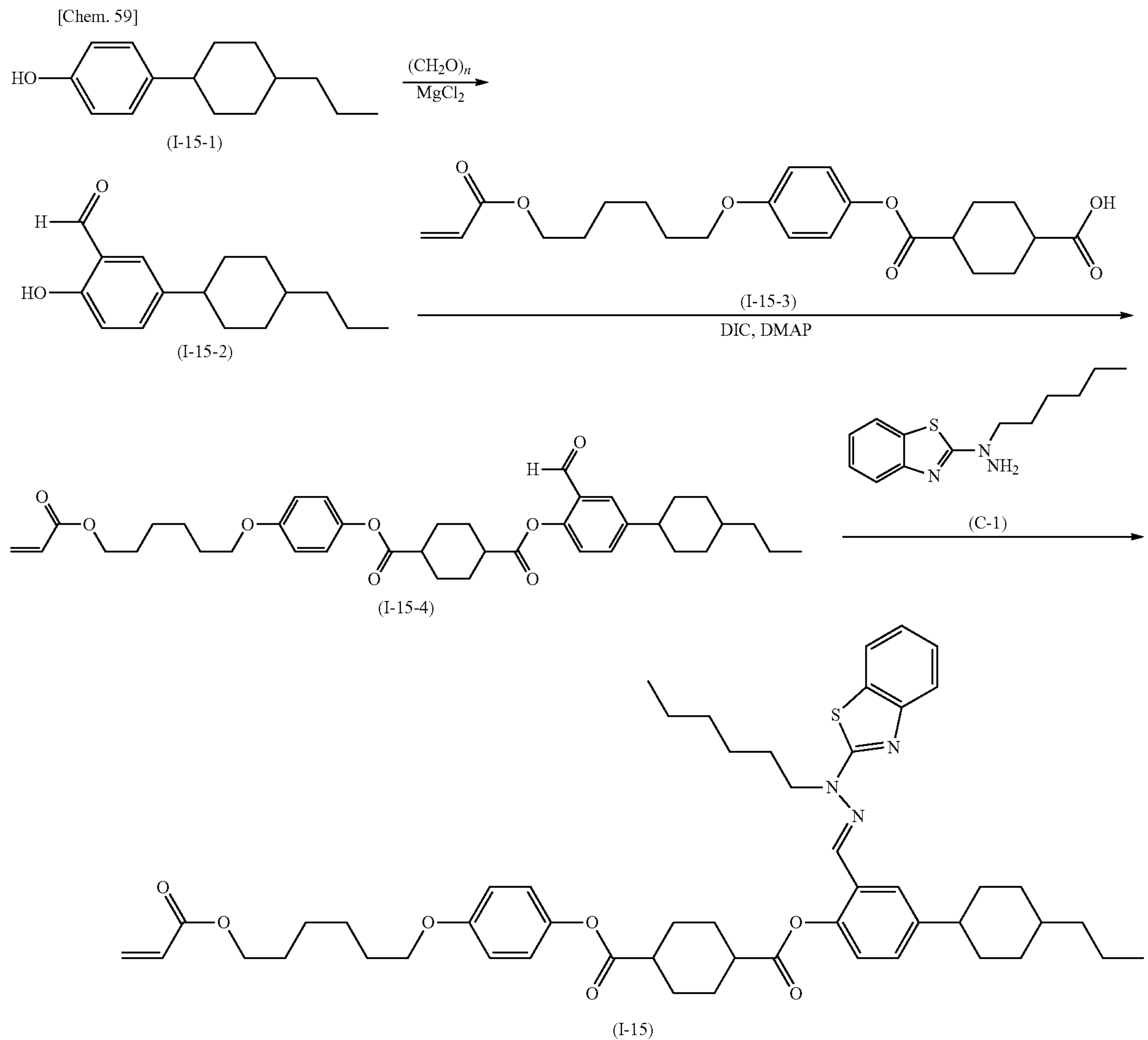

Into a reactor, 5.00 g of a compound represented by formula (I-15-1), 3.27 g of magnesium chloride, 2.06 g of paraformaldehyde, 20 mL of triethylamine, and 80 mL of acetonitrile were added. While the mixture was stirred at 60° C., paraformaldehyde was added thereto as appropriate. The Into a reactor, 1.0 g of a compound represented by formula (C-1) prepared in Example 1, 2.6 g of the compound represented by formula (I-15-4), 0.6 g of (±)-10-camphorsulfonic acid, 20 mL of tetrahydrofuran, and 10 mL of ethanol were added. After the mixture was heated and stirred at 50° C., the solvent was distilled away, and dispersion washing was performed with methanol. Purification by column chromatography (silica gel, dichloromethane) and recrystallization (dichloromethane/methanol) was performed to obtain 2.5 g of a compound represented by formula (I-15).

Transition temperature (temperature elevation: 5° C./minute): C 117-122 N 146 I $^1$H NMR ($CDCl_3$) δ 0.91 (m, 6H), 1.10 (q, 2H), 1.23-1.56 (m, 18H), 1.68-1.81 (m, 9H), 1.94 (t, 4H), 2.32 (m, 4H), 2.56-2.70 (m, 3H), 3.94 (t, 2H), 4.18 (t, 2H), 4.29 (t, 2H), 5.82 (dd, 1H), 6.13 (dd, 1H), 6.40 (dd, 1H), 6.89 (d, 2H), 6.99 (m, 3H), 7.16 (t, 1H), 7.23 (dd, 1H), 7.34 (t, 1H), 7.66-7.72 (m, 3H), 7.90 (d, 1H) ppm.

MS (m/z): 878 [$M^+$+1]

(Example 21) Production of Compound Represented by Formula (I-16)

[Chem. 60]

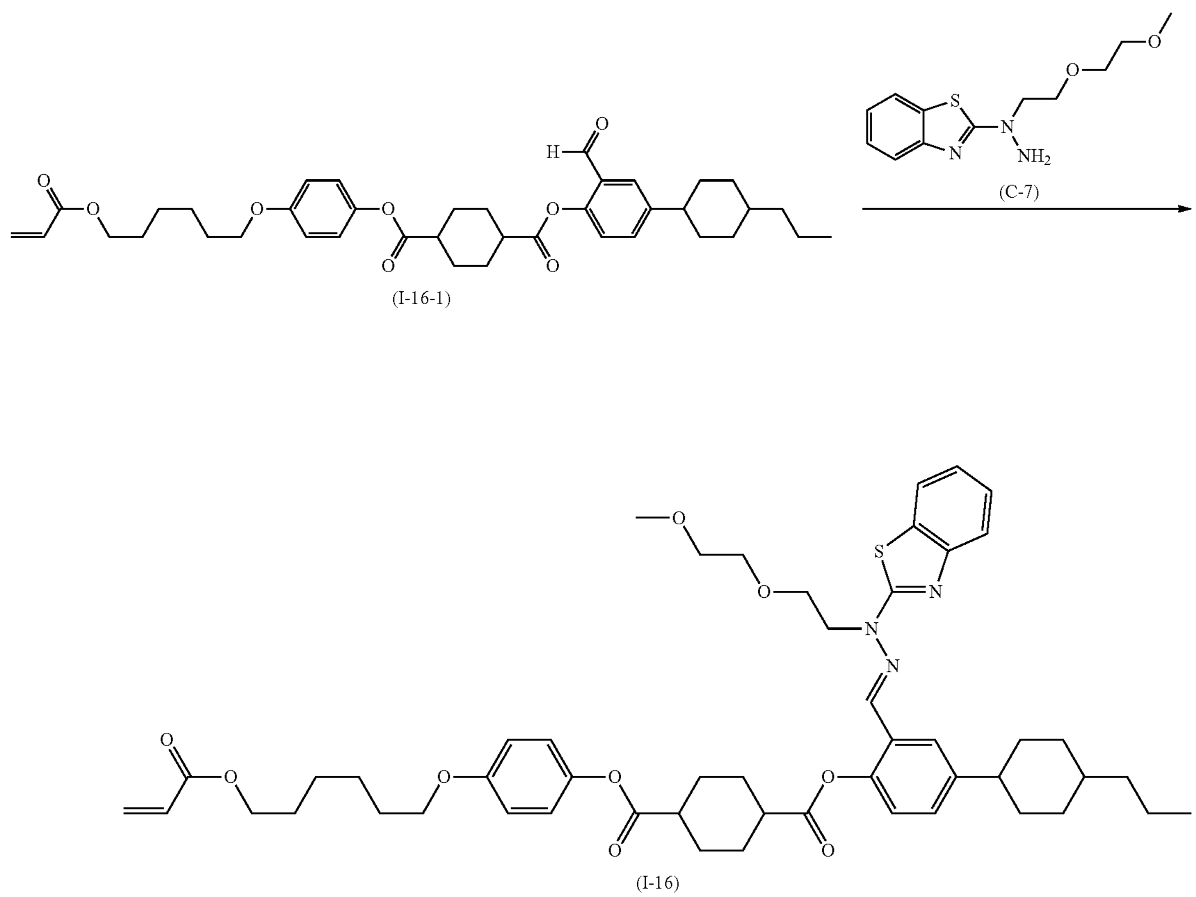

Into a reactor, 2.5 g of a compound represented by formula (I-16-1), 1.0 g of the compound represented by formula (C-7) prepared in Example 7, 0.5 g of (±)-10-camphorsulfonic acid, 10 mL of tetrahydrofuran, and 10 mL of ethanol were added. After the mixture was heated and stirred at 50° C., the solvent was distilled away, and dispersion washing was performed with methanol. Purification was performed by column chromatography (silica gel, dichloromethane) and recrystallization so as to obtain 2.0 g of a compound represented by formula (I-16).

Transition temperature (temperature elevation: 5° C./minute): C 106 N 125 I $^1$H NMR ($CDCl_3$) δ 0.92 (t, 3H), 1.05-1.83 (m, 22H), 1.93 (t, 5H), 2.33 (m, 4H), 2.55 (m, 2H), 2.71 (m, 1H), 3.30 (s, 3H), 3.62 (m, 2H), 3.85 (t, 2H), 3.94 (t, 2H), 4.17 (t, 2H), 4.48 (t, 2H), 5.82 (dd, 1H), 6.12 (dd, 1H), 6.40 (dd, 1H), 6.88 (d, 2H), 6.99 (m, 3H), 7.17 (t, 1H), 7.23 (dd, 1H), 7.34 (t, 1H), 7.66 (d, 1H), 7.71 (d, 1H), 7.89 (d, 1H), 8.02 (s, 1H) ppm.

(Example 22) Production of Compound Represented by Formula (I-17)

[Chem. 61]

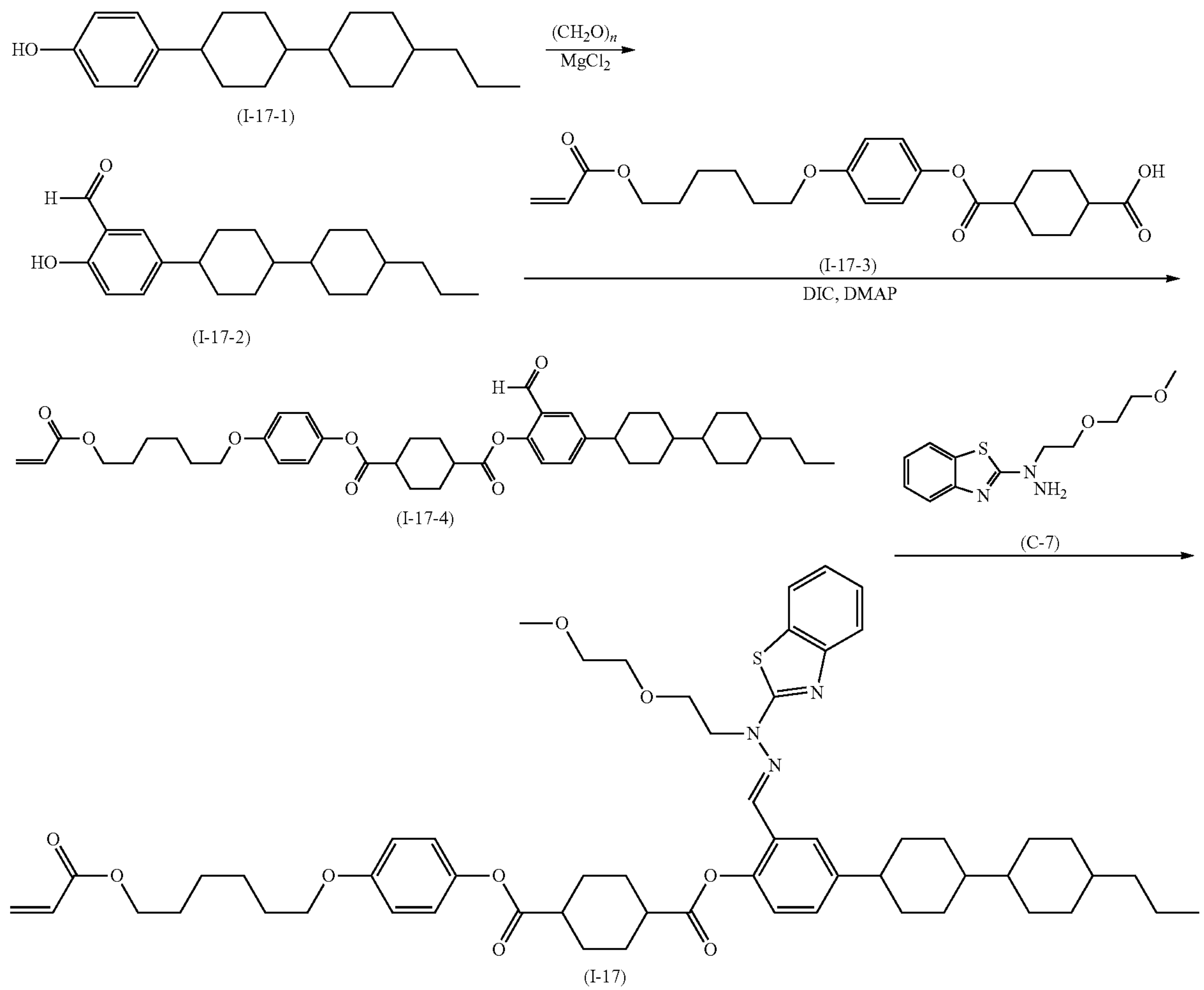

A compound represented by formula (I-17) was produced by the same method as in Example 20 except that the compound represented by formula (I-15-1) was replaced by the compound represented by formula (I-17-1), and the compound represented by formula (C-1) was replaced by the compound represented by formula (C-7) prepared in Example 7.

$^1$H NMR ($CDCl_3$) δ 0.92 (t, 3H), 1.05-1.83 (m, 32H), 1.93 (t, 5H), 2.33 (m, 4H), 2.55 (m, 2H), 2.71 (m, 1H), 3.30 (s, 3H), 3.62 (m, 2H), 3.85 (t, 2H), 3.94 (t, 2H), 4.17 (t, 2H), 4.48 (t, 2H), 5.82 (dd, 1H), 6.12 (dd, 1H), 6.40 (dd, 1H), 6.88 (d, 2H), 6.99 (m, 3H), 7.17 (t, 1H), 7.23 (dd, 1H), 7.34 (t, 1H), 7.66 (d, 1H), 7.71 (d, 1H), 7.89 (d, 1H), 8.02 (s, 1H) ppm.

MS (m/z): 978 [$M^+$+1]

(Example 23) Production of Compound Represented by Formula (I-18)

[Chem. 62]

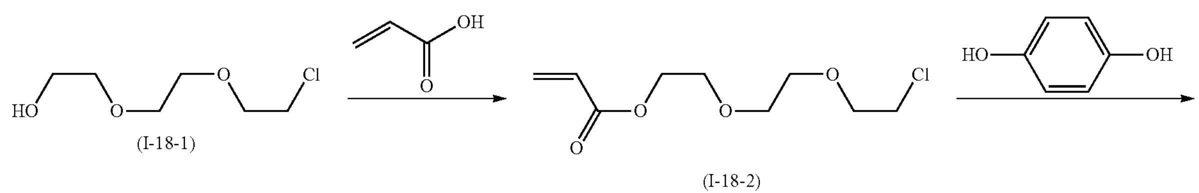

-continued

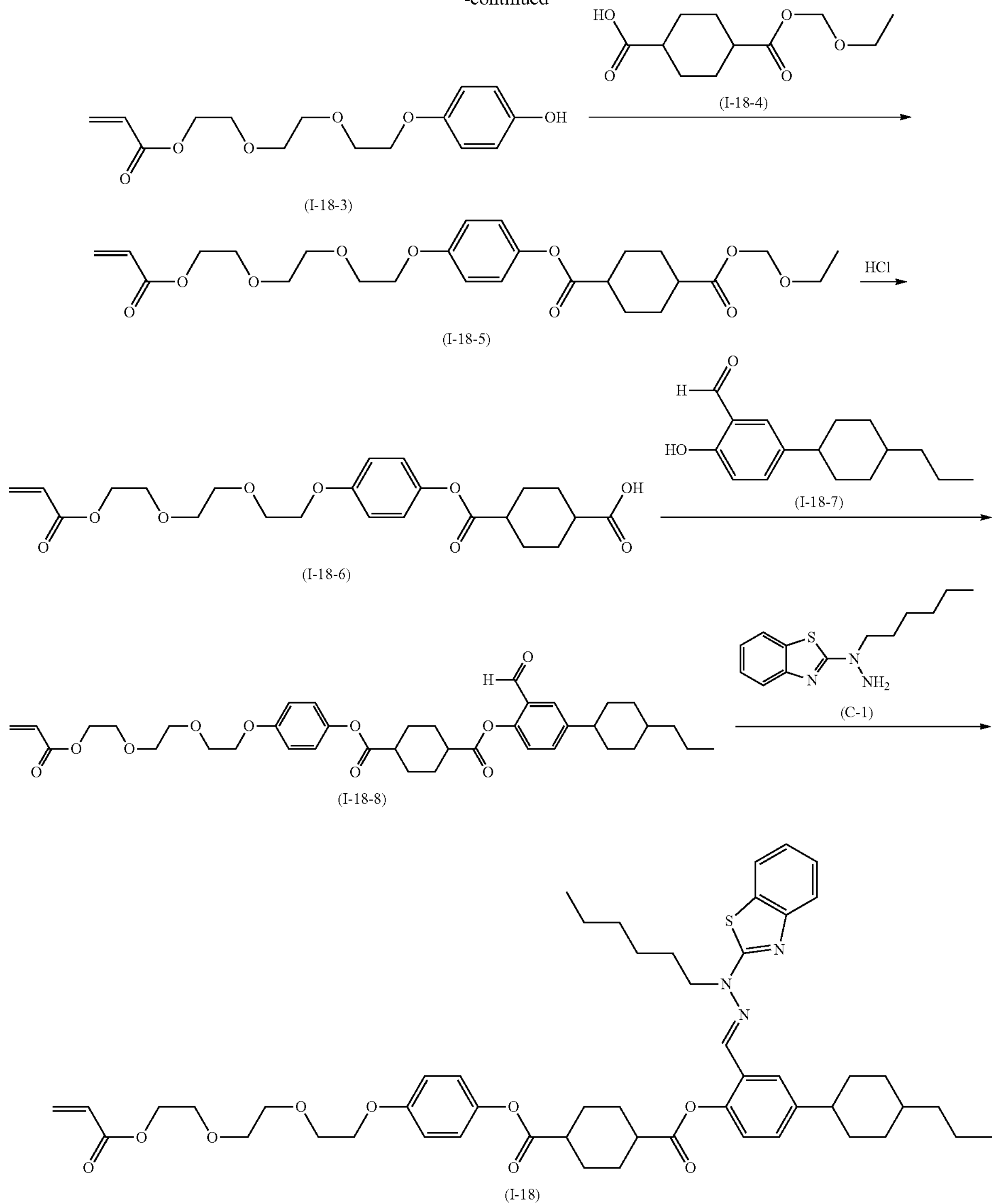

A compound represented by formula (I-18-6) was produced by the same method as in Example 15 except that the compound represented by formula (I-10-1) was replaced by the compound represented by formula (I-18-1).

A compound represented by formula (I-18) was produced by the same method as in Example 20 by using the compound represented by formula (C-1) prepared in Example 1 except that the compound represented by formula (I-15-4) was replaced by the compound represented by formula (I-18-8). Transition temperature (temperature elevation: 5° C./minute): C 131 I $^1$H NMR ($CDCl_3$) δ 0.88-0.94 (m, 6H), 1.10 (m, 2H), 1.22-1.52 (m, 13H), 1.72 (m, 6H), 1.94 (t, 4H), 2.32 (m, 4H), 2.53-2.62 (m, 3H), 3.69-3.77 (m, 6H), 3.86 (t, 2H), 4.12 (t, 2H), 4.27-4.34 (m, 4H), 5.83 (dd, 1H), 6.16 (dd, 1H), 6.43 (dd, 1H), 6.91 (d, 2H), 6.97-7.02 (m, 3H), 7.16 (t, 1H), 7.23 (dd, 1H), 7.33 (t, 1H), 6.66-7.72 (m, 3H), 7.90 (d, 1H) ppm.

LCMS: 910 [M+1]

(Example 24) Production of Compound Represented by Formula (I-19)

[Chem. 63]

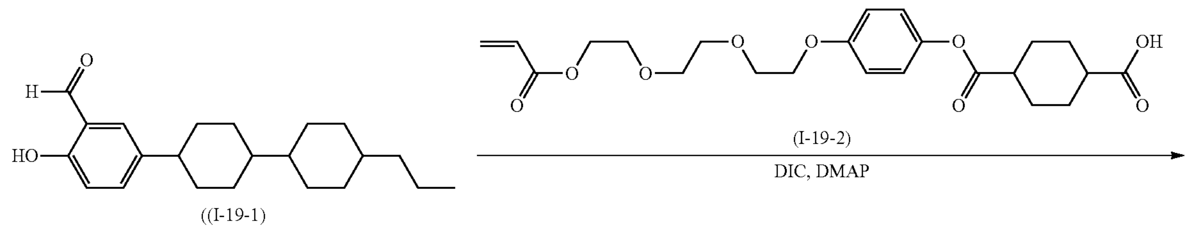

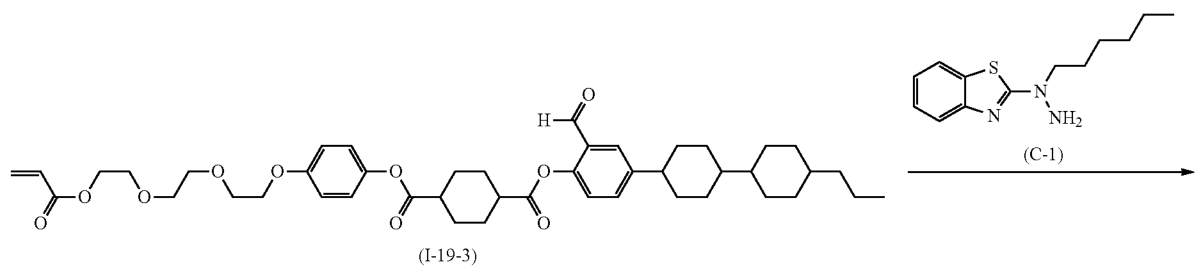

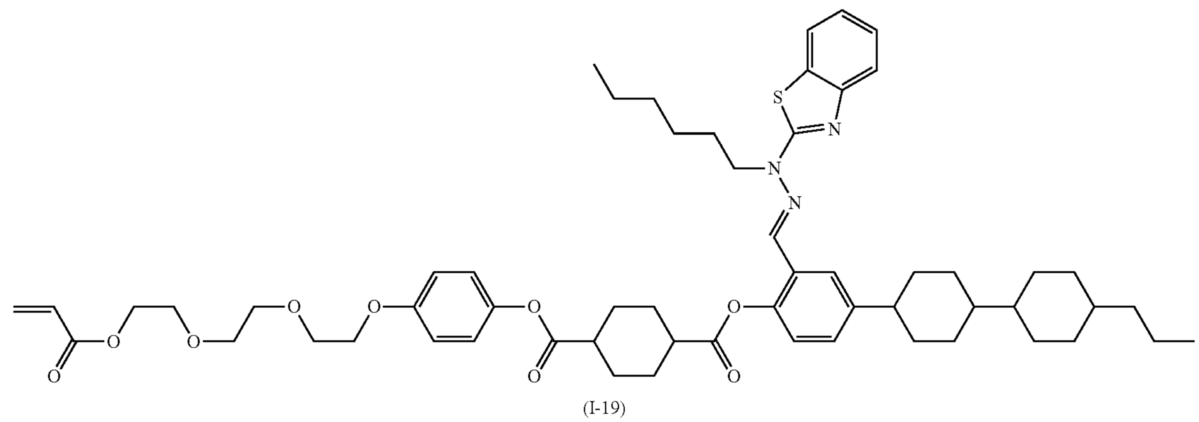

A compound represented by formula (I-19) was produced by the same method as in Example 23 by using the compound represented by formula (C-1) prepared in Example 1 except that the compound represented by formula (I-18-7) was replaced by the compound represented by formula (I-19-1). Transition temperature (temperature elevation: 5° C./minute): C 90 S 218 N 265 I $^{1}$H NMR ($CDCl_3$) δ 0.88 (m, 6H), 1.01-1.19 (m, 8H), 1.32-1.45 (m, 6H), 1.71-1.76 (m, 6H), 1.88-1.99 (m, 3H), 2.17 (m, 12H), 2.31 (m, 4H), 2.53 (m, 2H), 2.67 (m, 1H), 3.70-3.76 (m, 6H), 3.85 (t, 2H), 4.11 (t, 2H), 4.31 (m, 4H), 5.82 (d, 2H), 6.15 (q, 2H), 6.43 (d, 2H), 6.92 (m, 5H), 7.14-7.26 (m, 2H), 7.33 (t, 1H), 7.68 (m, 3H), 7.88 (s, 1H) ppm.

(Example 25) Production of Compound Represented by Formula (I-20)

[Chem. 64]

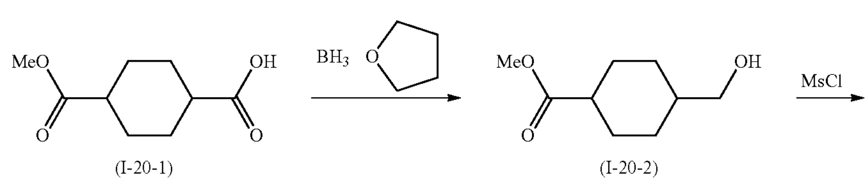

-continued

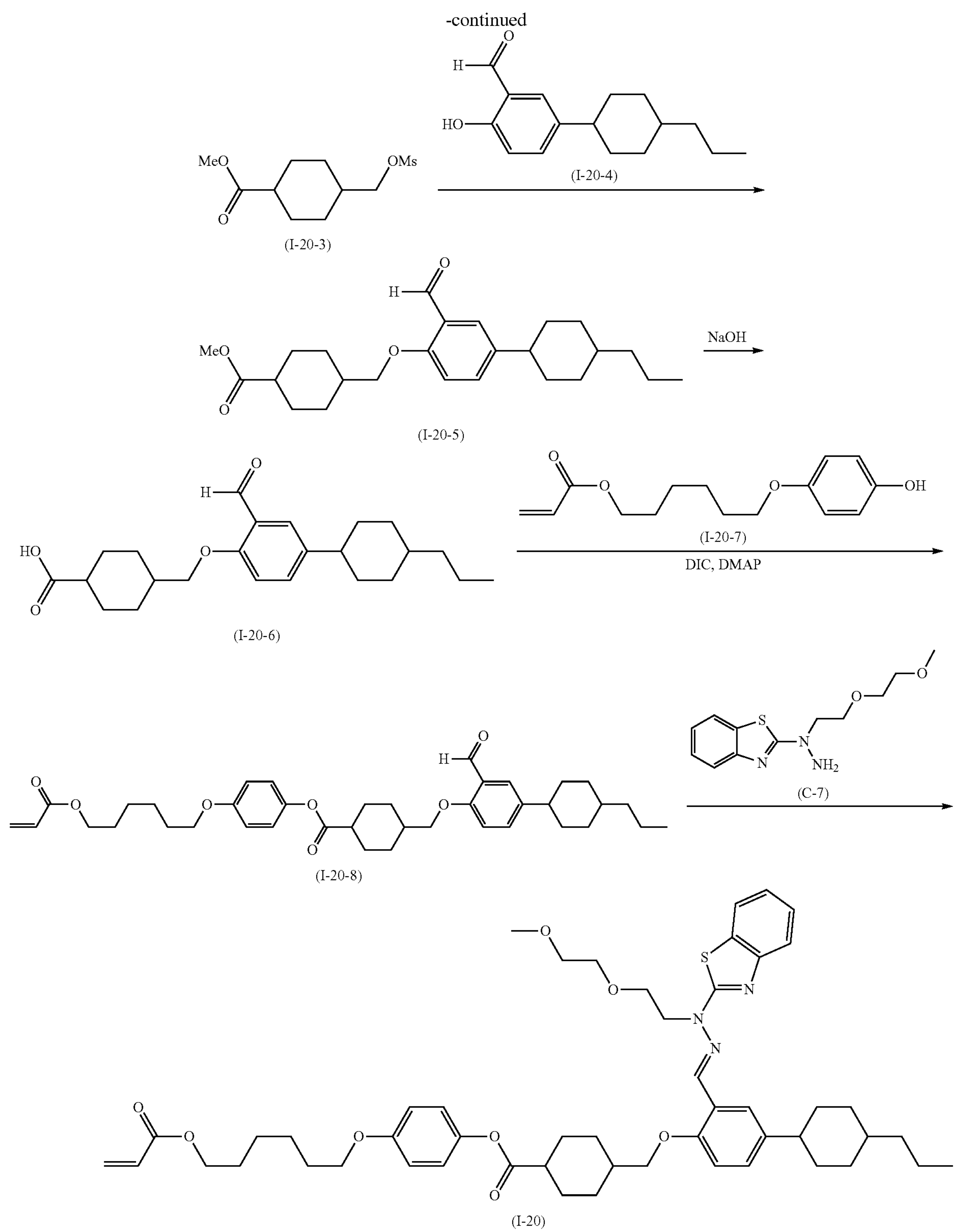

In a nitrogen atmosphere, 20.0 g of a compound represented by formula (I-20-1) and 120 mL of tetrahydrofuran were added into a reactor. While the mixture was being cooled over ice, 143 mL of a borane-tetrahydrofuran complex (0.9 mol/L) was added dropwise, followed by stirring for 2 hours. After the mixture was poured into 200 mL of a 5% hydrochloric acid, a liquid separation process was performed by using 200 mL of ethyl acetate. After drying over sodium sulfate, the solvent was distilled away so as to obtain 17.6 g of a compound represented by formula (I-20-2).

In a nitrogen atmosphere, 17.6 g of a compound represented by formula (I-20-2), 12.1 g of pyridine, and 100 mL of dichloromethane were added into a reactor. While the mixture was being cooled over ice, 12.9 g of methanesulfonyl chloride was added dropwise, followed by stirring at room temperature for 8 hours. After the resulting mixture was poured into a 5% hydrochloric acid, a liquid separation process was performed. Purification was performed by column chromatography (silica gel, dichloromethane) so as to obtain 23.0 g of a compound represented by formula (I-20-3).

Into a reactor, 4.0 g of a compound represented by formula (I-20-3), 3.9 g of a compound represented by formula (I-20-4), 3.5 g of potassium carbonate, and 30 mL of N,N-dimethylformamide were added, and the resulting mixture was heated and stirred at 90° C. for 12 hours. The mixture was diluted with dichloromethane and was washed with water and brine. Purification by column chromatography (silica gel, dichloromethane) and recrystallization (dichloromethane/methanol) was performed to obtain 5.1 g of a compound represented by formula (I-20-5).

Into a reactor, 5.1 g of a compound represented by formula (I-20-5), 30 mL of tetrahydrofuran, 30 mL of methanol, and 10 mL of a 25% aqueous sodium hydroxide solution were added, followed by stirring at 60° C. Hydrochloric acid was added thereto, and the solvent was distilled away. The mixture was then washed with water and dried so as to obtain 4.9 g of a compound represented by formula (I-20-6).

In a nitrogen atmosphere, 4.9 g of a compound represented by formula (I-20-6), 3.4 g of a compound represented by formula (I-20-7), 0.1 g of N,N-dimethylaminopyridine, and 40 mL of dichloromethane were added into a reactor. While the mixture was being cooled over ice, 1.6 g of diisopropylcarbodiimide was added dropwise, followed by stirring. Purification by column chromatography (silica gel, dichloromethane) and recrystallization (dichloromethane/methanol) was performed to obtain 5.7 g of a compound represented by formula (I-20-8).

Into a reactor, 2.5 g of a compound represented by formula (I-20-8), 1.1 g of the compound represented by formula (C-7) prepared in Example 7, 0.5 g of (±)-10-camphorsulfonic acid, 10 mL of tetrahydrofuran, and 10 mL of ethanol were added. After the mixture was heated and stirred at 50° C., the solvent was distilled away, and dispersion washing was performed with methanol. Purification by column chromatography (silica gel, dichloromethane) and recrystallization (dichloromethane/methanol) was performed to obtain 2.1 g of a compound represented by formula (I-20).

Transition temperature (temperature elevation: 5° C./minute, temperature decrease: 5° C./minute): C 101-105 (N 82) I $^{1}$H NMR ($CDCl_3$) δ 0.92 (t, 3H), 1.08-1.91 (m, 26H), 2.06 (d, 2H), 2.24 (d, 2H), 2.51 (m, 2H), 3.30 (s, 3H), 3.51 (dd, 2H), 3.67 (dd, 2H), 3.87 (quin, 4H), 3.94 (t, 2H), 4.17 (t, 2H), 4.54 (t, 2H), 5.82 (dd, 1H), 6.12 (dd, 1H), 6.40 (dd, 1H), 6.86 (m, 3H), 6.97 (m, 2H), 7.16 (m, 2H), 7.32 (t, 1H), 7.65 (d, 1H), 7.70 (d, 1H), 7.82 (d, 1H), 8.36 (s, 1H) ppm.

(Example 26) Production of Compound Represented by Formula (I-21)

[Chem. 65]

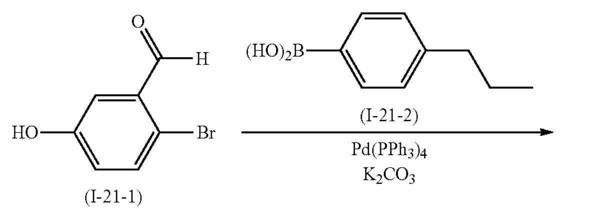

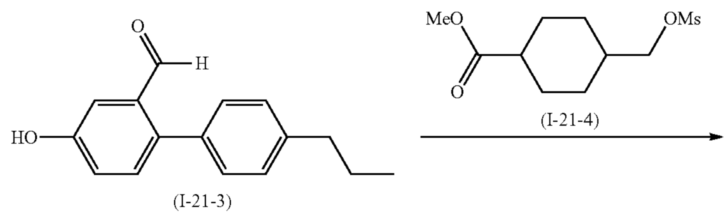

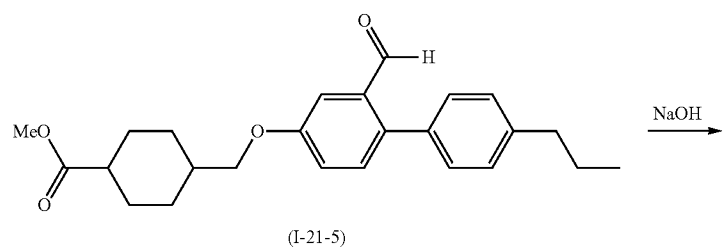

-continued

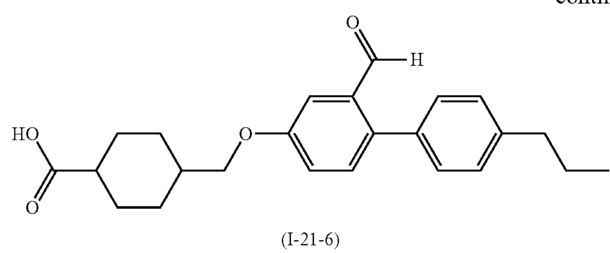

(I-21-6)

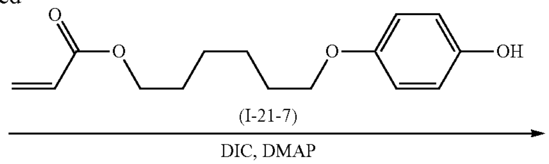

(I-21-7)

DIC, DMAP (I-21-8)

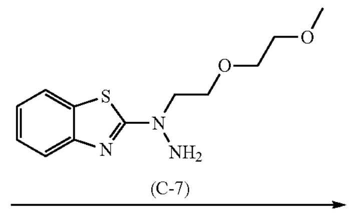

(C-7)

(I-21)

Into a reactor, 5.0 g of a compound represented by formula (I-21-1), 4.1 g of a compound represented by formula (I-21-2), 5.2 g of potassium carbonate, and 50 mL of ethanol were added. After the reactor was purged with nitrogen, 0.3 g of tetrakis(triphenylphosphine)palladium(0) was added, and the resulting mixture was refluxed under heating. After dilution with ethyl acetate and washing with a 5% hydrochloric acid and brine, purification was performed by column chromatography (silica gel, ethyl acetate) so as to obtain 4.8 g of a compound represented by formula (I-21-3).

Into a reactor, 4.0 g of a compound represented by formula (I-21-3), 4.2 g of a compound represented by formula (I-21-4), 3.5 g of potassium carbonate, and 30 mL of N,N-dimethylformamide were added, and the resulting mixture was heated and stirred at 90° C. for 12 hours. The mixture was diluted with dichloromethane and was washed with water and brine. Purification by column chromatography (silica gel, dichloromethane) and recrystallization (dichloromethane/methanol) was performed to obtain 4.6 g of a compound represented by formula (I-21-5).

Into a reactor, 4.6 g of a compound represented by formula (I-21-5), 30 mL of tetrahydrofuran, 30 mL of methanol, and 10 mL of a 25% aqueous sodium hydroxide solution were added, followed by stirring at 60° C. Hydrochloric acid was added thereto, and the solvent was distilled away. The mixture was then washed with water and dried so as to obtain 4.4 g of a compound represented by formula (I-21-6).

In a nitrogen atmosphere, 4.4 g of a compound represented by formula (I-21-6), 3.1 g of a compound represented by formula (I-21-7), 0.1 g of N,N-dimethylaminopyridine, and 40 mL of dichloromethane were added into a reactor. While the mixture was being cooled over ice, 1.8 g of diisopropylcarbodiimide was added dropwise, followed by stirring. Purification by column chromatography (silica gel, dichloromethane) and recrystallization (dichloromethane/methanol) was performed to obtain 5.1 g of a compound represented by formula (I-21-8).

Into a reactor, 2.5 g of a compound represented by formula (I-21-8), 1.1 g of the compound represented by formula (C-7) produced by the method described in Example 7, 0.5 g of (±)-10-camphorsulfonic acid, 10 mL of tetrahydrofuran, and 10 mL of ethanol were added. After the mixture was heated and stirred at 50° C., the solvent was distilled away, and dispersion washing was performed with methanol. Purification by column chromatography (silica gel, dichloromethane) and recrystallization (dichloromethane/methanol) was performed to obtain 1.8 g of a compound represented by formula (I-21).

Transition temperature (temperature elevation: 5° C./minute): C 67-100 I $^{1}H$ NMR ($CDCl_3$) δ 1.00 (t, 3H), 1.28 (m, 2H), 1.45-1.81 (m, 12H), 1.97 (br, 1H), 2.13 (m, 2H), 2.26 (m, 2H), 2.57 (tt, 1H), 2.65 (t, 2H), 3.27 (s, 3H), 3.37 (m, 2H), 3.50 (m, 2H), 3.70 (t, 2H), 3.95 (q, 4H), 4.17 (t, 2H), 4.33 (t, 2H), 5.82 (dd, 1H), 6.12 (dd, 1H), 6.40 (dd, 1H), 6.87 (d, 2H), 6.98 (m, 3H), 7.15 (t, 1H), 7.25 (m, 5H), 7.32 (t, 1H), 7.64 (m, 2H), 7.69 (d, 1H), 7.91 (s, 1H) ppm.

(Example 27) Production of Compound Represented by Formula (I-22)

[Chem. 66]

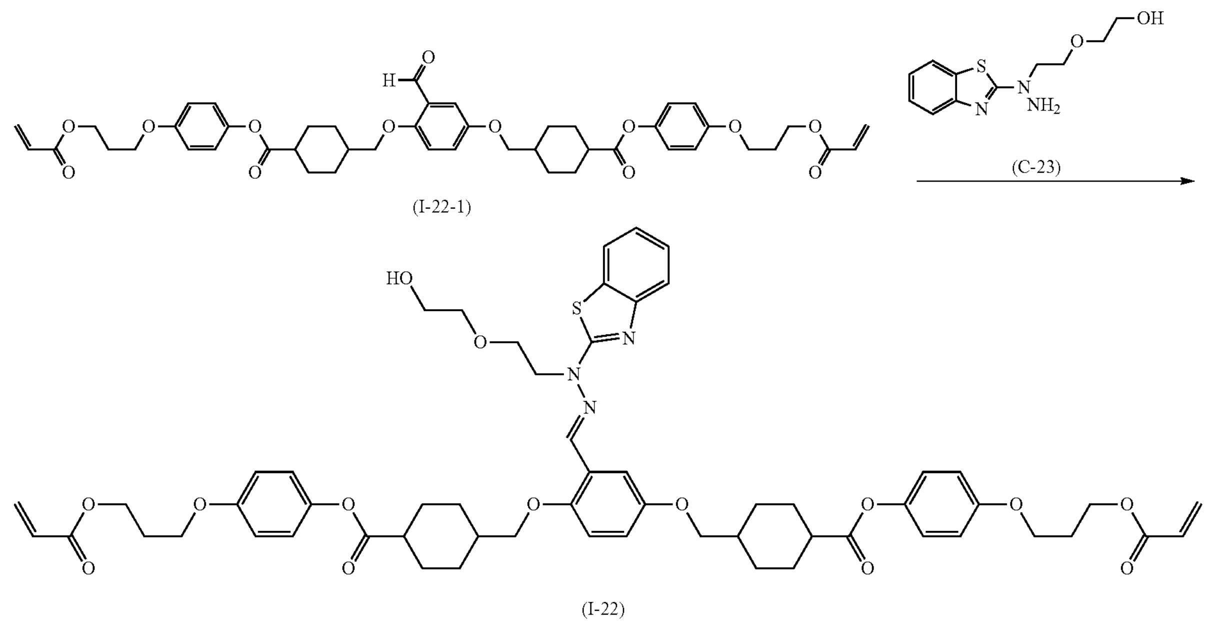

In a nitrogen atmosphere, 3.0 g of a compound represented by formula (I-22-1), 0.9 g of the compound represented by formula (C-23) prepared in Example 10, 0.5 g of (±)-10-camphorsulfonic acid, 30 mL of tetrahydrofuran, and 15 mL of ethanol were added into a reactor, followed by heating and stirring at 50° C. After the solvent was distilled away, methanol was added to perform crystallization, and the crystals were filtered. Purification by column chromatography (silica gel, dichloromethane) and recrystallization (dichloromethane/methanol) was performed to obtain 3.5 g of a compound represented by formula (I-22).

LCMS: 1062 [M+1]

(Example 28) Production of Compound Represented by Formula (I-23)

[Chem. 67]

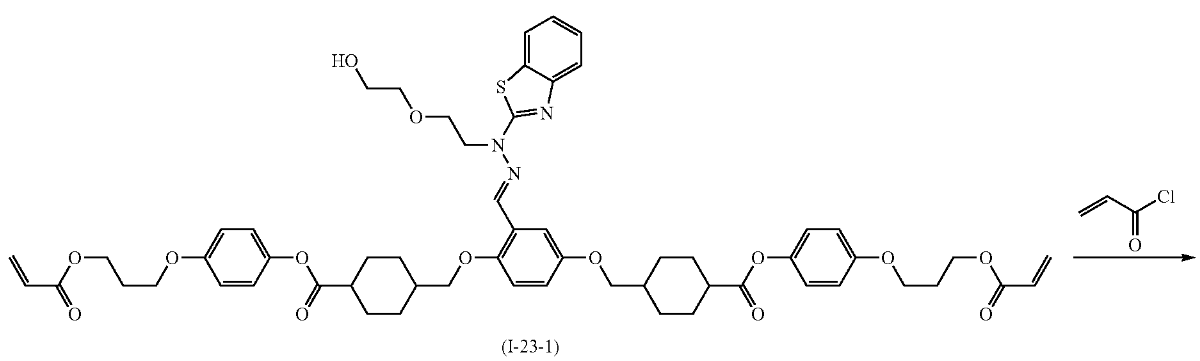

-continued

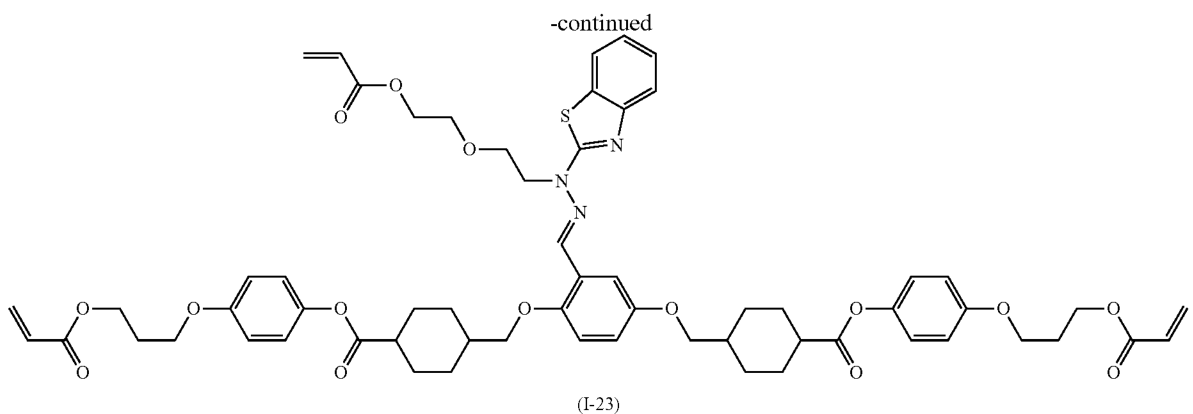

(I-23)

In a nitrogen atmosphere, 3.0 g of a compound represented by formula (I-23-1), 0.3 g of triethylamine, and 30 mL of dichloromethane were added into a reactor. While the mixture was being cooled over ice, 0.3 g of acryloyl chloride was added dropwise, followed by stirring at room temperature for 5 hours. After the mixture was washed with a 1% hydrochloric acid and brine, purification by column chromatography (silica gel, dichloromethane) and recrystallization (dichloromethane/methanol) was performed to obtain 2.5 g of a compound represented by formula (I-23). LCMS: 1116 [M+1]

(Example 29) Production of Compound Represented by Formula (I-24)

[Chem. 68]

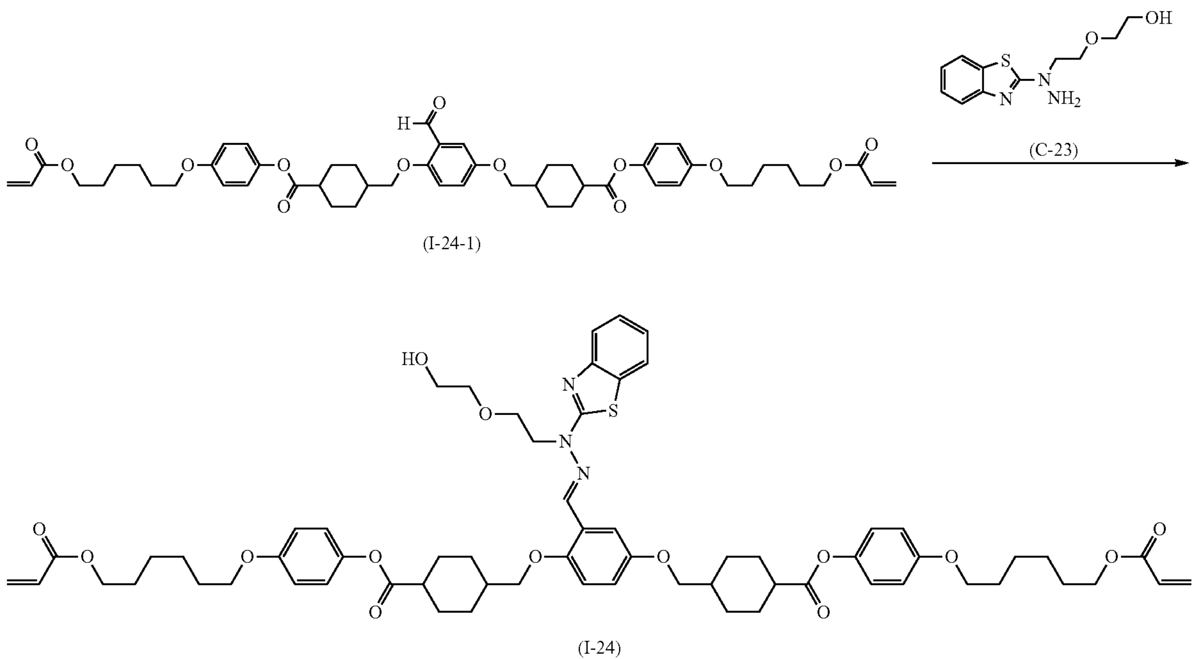

In a nitrogen atmosphere, 3.0 g of a compound represented by formula (I-24-1), 0.8 g of the compound represented by formula (C-23) prepared in Example 10, 0.5 g of (±)-10-camphorsulfonic acid, 30 mL of tetrahydrofuran, and 15 mL of ethanol were added into a reactor, followed by heating and stirring at 50° C. After the solvent was distilled away, methanol was added to perform crystallization, and the crystals were filtered. Purification by column chromatography (silica gel, dichloromethane) and recrystallization (dichloromethane/methanol) was performed to obtain 3.2 g of a compound represented by formula (I-24).

LCMS: 1146 [M+1]

(Example 30) Production of Compound Represented by Formula (I-25)

[Chem. 69]

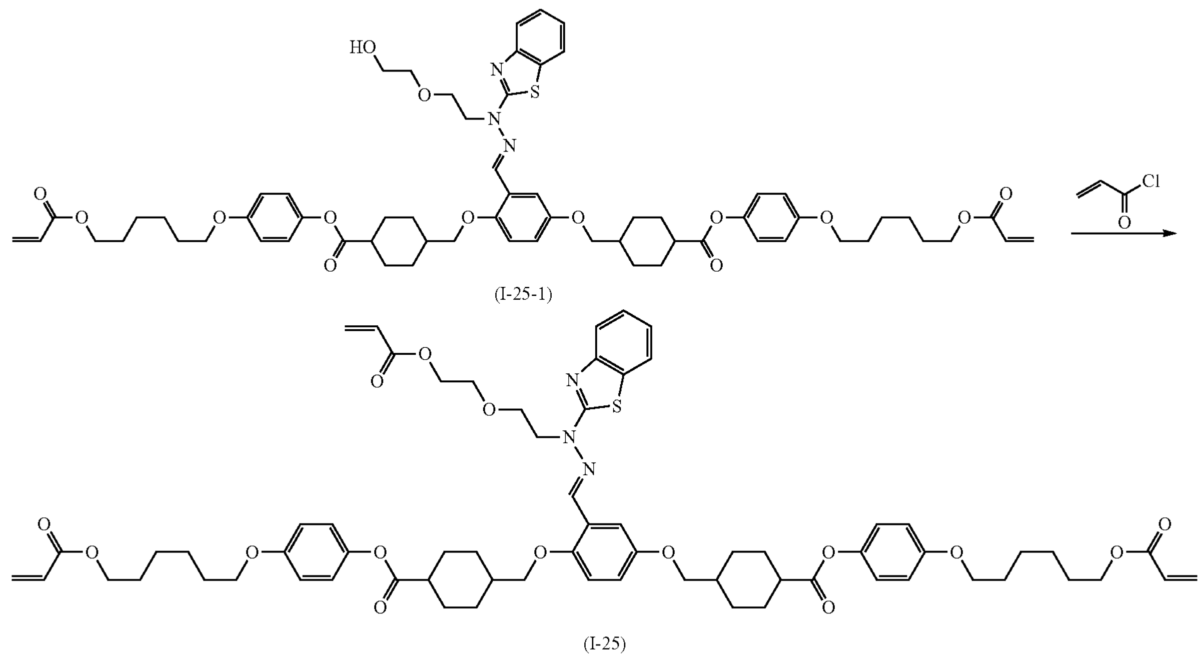

In a nitrogen atmosphere, 3.0 g of a compound represented by formula (I-25-1), 0.3 g of triethylamine, and 30 mL of dichloromethane were added into a reactor. While the mixture was being cooled over ice, 0.3 g of acryloyl chloride was added dropwise, followed by stirring at room temperature for 5 hours. After the mixture was washed with a 1% hydrochloric acid and brine, purification by column chromatography (silica gel, dichloromethane) and recrystallization (dichloromethane/methanol) was performed to obtain 2.5 g of a compound represented by formula (I-25). Transition temperature (temperature elevation: 5° C./minute): C 63 N 112 I $^1$H NMR ($CDCl_3$) δ 1.24 (m, 4H), 1.42-1.83 (m, 20H), 1.91 (m, 2H), 2.08 (m, 4H), 2.24 (m, 4H), 2.53 (m, 2H), 3.74 (t, 2H), 3.85 (dd, 4H), 3.91-3.96 (m, 6H), 4.17 (t, 4H), 4.25 (t, 2H), 4.53 (t, 2H), 5.67 (dd, 1H), 5.82 (dd, 2H), 5.95 (dd, 1H), 6.12 (dd, 2H), 6.29 (dd, 1H), 6.41 (dd, 2H), 6.82-6.90 (m, 6H), 6.96-6.99 (m, 4H), 7.15 (t, 1H), 7.33 (t, 1H), 7.53 (d, 1H), 7.67 (dd, 2H), 8.38 (s, 1H) ppm.

LCMS: 1200 [M+1]

Examples 31 to 55 and Comparative Examples 9 to 16

Preparation of Films

In preparing films, a liquid crystal composition containing a compound (X-1) described in International Publication No. WO 2012/002140 A1: 20%, a compound (X-2) described in Japanese Unexamined Patent Application Publication (Translation of PCT Application) No. 2002-542219: 20%, and a compound (X-3) described in Japanese Unexamined Patent Application Publication No. 2005-015473: 60% was used as a matrix liquid crystal (X).

[Chem. 70]

(X-1)

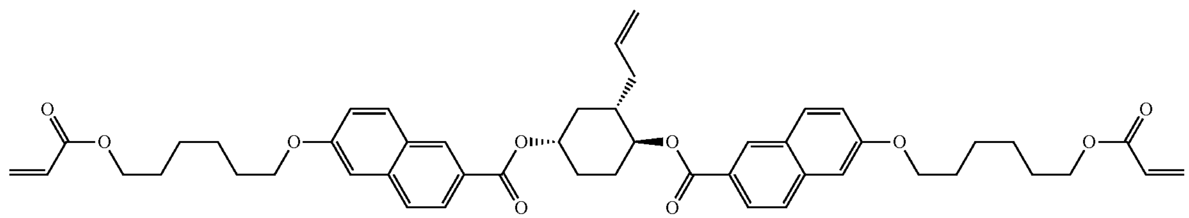

-continued (X-2)

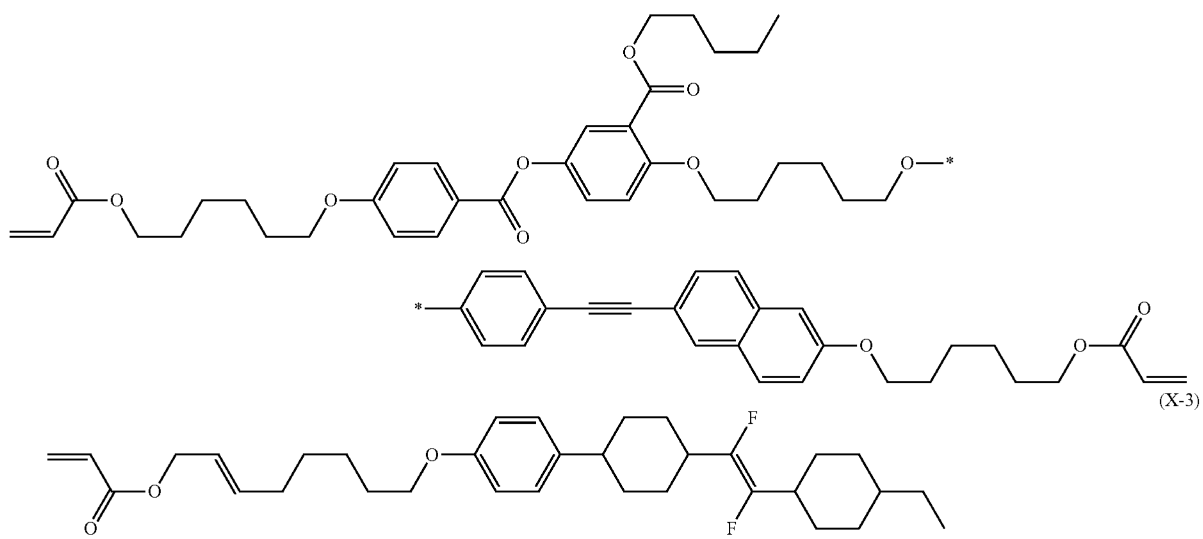

(X-3)

A polyimide solution for an alignment film was applied to a glass substrate having a thickness of 0.7 mm by a spin coating method, dried at 100° C. for 10 minutes, and baked at 200° C. for 60 minutes. As a result, a coating film was obtained. The coating film was subjected to a rubbing process. The rubbing process was performed by using a commercially available rubbing machine.

To each composition prepared by adding 30% of a compound to be evaluated to the matrix liquid crystal (X), 1% of a photopolymerization initiator, Irgacure 907 (produced by BASF), 0.1% of 4-methoxyphenol, and 80% of chloroform were added so as to prepare a coating solution. The coating solution was applied to the rubbed glass substrate by a spin coating method. The applied solution was dried at 80° C. for 1 minute, and then at 120° C. for 1 minute. Subsequently, by using a high-pressure mercury lamp, the UV ray was applied for 25 seconds at an intensity of 40 mW/cm$^2$ so as to prepare a film to be evaluated.

Each of the films prepared was irradiated with 100 J of light using a xenon lamp irradiation tester (SUNTEST XLS produced by Atlas Material Testing Technology GmbH) at 50 mW/cm$^2$ at 25° C. Each of the films was evaluated in terms of changes in color and orientation. The evaluation results are shown in the tables below.

<Change in Color>

The yellow index (YI) of the film before irradiation and that after irradiation were measured, and the change in yellowness (ΔYI) was determined. The yellow index was determined by measuring an absorption spectrum of a polymer by using JASCO UV/VIS Spectrophotometer V-560, and calculating the yellow index (YI) by using an accompanying color determination program. The calculation formula was as follows:

$$YI=100(1.28X-1.06Z)/Y$$

(Where YI represents a yellow index, and X, Y, and Z represent tristimulus values in the XYZ color system (JIS K 7373).) The change in yellowness (ΔYI) means the difference between the yellow index before irradiation and the yellow index after irradiation.

<Changes in Orientation>

The orientation was evaluated through polarizing microscope observation. Specifically, a 10 mm×10 mm region was selected in the surface of the film at random, films in which no defects were observed in that region were rated A, and a film that had the largest number of defects was rated E. Then the films were evaluated in the scale of five, A, B, C, D, and E, according to the extent of the orientation defects. Here, films rated B had very few defects, films rated C had some defects, and films rated D had a fair number of defects.

TABLE 1

| Film | Compound used and evaluated | ΔYI | Orientation |
|---|---|---|---|
| Example 31 | Compound (I-1) of the present invention | 0.8 | C |
| Example 32 | Compound (I-2) of the present invention | 0.8 | C |
| Example 33 | Compound (I-3) of the present invention | 0.9 | C |
| Example 34 | Compound (I-4) of the present invention | 0.8 | C |
| Example 35 | Compound (I-5) of the present invention | 0.3 | A |
| Example 36 | Compound (I-6) of the present invention | 0.4 | B |
| Example 37 | Compound (I-7) of the present invention | 0.5 | B |
| Example 38 | Compound (I-8) of the present invention | 0.6 | C |
| Example 39 | Compound (I-9) of the present invention | 0.2 | A |
| Example 40 | Compound (I-10) of the present invention | 0.4 | B |

TABLE 2

| Film | Compound used and evaluated | ΔYI | Orientation |
|---|---|---|---|
| Example 41 | Compound (I-11) of the present invention | 0.5 | B |
| Example 42 | Compound (I-12) of the present invention | 0.2 | A |

TABLE 2-continued

| Film | Compound used and evaluated | ΔYI | Orientation |
|---|---|---|---|
| Example 43 | Compound (I-13) of the present invention | 0.3 | A |
| Example 44 | Compound (I-14) of the present invention | 0.2 | A |
| Example 45 | Compound (I-15) of the present invention | 0.5 | B |
| Example 46 | Compound (I-16) of the present invention | 0.3 | A |
| Example 47 | Compound (I-17) of the present invention | 0.3 | A |
| Example 48 | Compound (I-18) of the present invention | 0.8 | C |
| Example 49 | Compound (I-19) of the present invention | 0.7 | C |
| Example 50 | Compound (I-20) of the present invention | 0.5 | B |

TABLE 3

| Film | Compound used and evaluated | ΔYI | Orientation |
|---|---|---|---|
| Example 51 | Compound (I-21) of the present invention | 0.5 | B |
| Example 52 | Compound (I-22) of the present invention | 0.2 | A |
| Example 53 | Compound (I-23) of the present invention | 0.3 | A |
| Example 54 | Compound (I-24) of the present invention | 0.2 | A |
| Example 55 | Compound (I-25) of the present invention | 0.3 | A |

TABLE 4

| Film | Compound used and evaluated | ΔYI | Orientation |
|---|---|---|---|
| Comparative Example 9 | Comparative Compound (I-1R) | 1.3 | E |
| Comparative Example 10 | Comparative Compound (I-2R) | 1.4 | E |
| Comparative Example 11 | Comparative Compound (I-3R) | 1.3 | E |
| Comparative Example 12 | Comparative Compound (I-4R) | 1.4 | E |
| Comparative Example 13 | Comparative Compound (I-5R) | 0.8 | C |
| Comparative Example 14 | Comparative Compound (I-6R) | 1.0 | D |
| Comparative Example 15 | Comparative Compound (I-7R) | 1.1 | D |
| Comparative Example 16 | Comparative Compound (I-8R) | 1.0 | E |

The tables show that the films that contain the compounds of Examples 31 to 55 produced by the method of the present invention undergo less changes in color and orientation after long UV irradiation compared to the films that contain the compounds produced by the methods of Comparative Examples. It is presumed that when a 2-hydrazinobenzothiazole derivative, which is an intermediate having a substituent, such as an alkyl group, on the nitrogen atom, is produced by the method of Comparative undergoes extensive coloration ranging from brown to dark blue during the N-alkylation reaction step, which indicates generation of large by-products of the conjugated system. These by-products either could not be completely removed in the subsequent steps or were induced to give impurities of higher molecular weights; thus, trace amounts of these by-products and impurities mixed into the targeted polymerizable compound, and possibly adversely affected changes in color and orientation. Meanwhile, according to the method of the invention of the present application, the color of the reaction solution during the reaction was light, ranging from pale yellow to pale blue; thus, generation of the by-products described above was suppressed, and there were less adverse effects when films were prepared from the polymerizable compounds by using the obtained intermediate.

The results described above show that the compounds produced by the method of the invention of the present invention are useful as a constituent member of polymerizable compositions. Moreover, an optically anisotropic body that uses the composition containing the compound of the present invention is useful for usage such as optical films.

The invention claimed is:

1. A method for producing a compound represented by general formula (I) below, the method comprising:

a first step of obtaining a compound represented by general formula (I-C) by reacting a compound represented by general formula (I-B) below with a compound represented by general formula (I-A) below in the presence of at least one compound selected from the group consisting of lithium amide, sodium amide, magnesium amide, potassium amide, calcium amide, cesium amide, lithium diisopropylamide, lithium hydride, sodium hydride, magnesium hydride, potassium hydride, calcium hydride, cesium hydride, lithium aluminum hydride, lithium borohydride, lithium methoxide, sodium methoxide, magnesium methoxide, potassium methoxide, calcium methoxide, cesium methoxide, lithium ethoxide, sodium ethoxide, magnesium ethoxide, potassium ethoxide, calcium ethoxide, cesium ethoxide, lithium propoxide, sodium propoxide, magnesium propoxide, potassium propoxide, calcium propoxide, cesium propoxide, lithium isopropoxide, sodium isopropoxide, magnesium isopropoxide, potassium isopropoxide, calcium isopropoxide, cesium isopropoxide, lithium butoxide, sodium butoxide, magnesium butoxide, potassium butoxide, calcium butoxide, cesium butoxide, lithium tert-butoxide, sodium tert-butoxide, magnesium tert-butoxide, potassium tert-butoxide, calcium tert-butoxide, cesium tert-butoxide, methyl lithium, ethyl lithium, propyl lithium, butyl lithium, sec-butyl lithium, tert-butyl lithium, pentyl lithium, hexyl lithium, and phenyl lithium; and a second step of obtaining a compound represented by general formula (I) by reacting the compound represented by general formula (I-C) obtained in the first step with a compound represented by general formula (I-D) below:

(I-B)

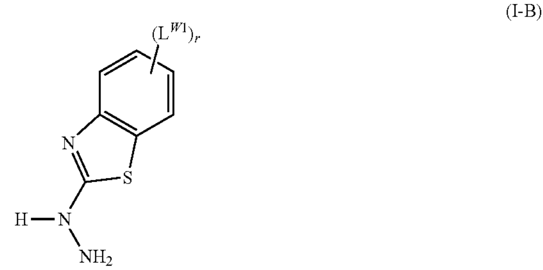

where r represents an integer of 0 to 4, $L^{W1}$ represents a fluorine atom, a chlorine atom, a bromine atom, an iodine atom, a pentafluorosulfuranyl group, a nitro group, a cyano group, a dimethylamino group, a diethylamino group, a diisopropylamino group, or a linear or branched alkyl group having 1 to 20 carbon atoms, in which one —$CH_2$— or two or more non-adjacent —$CH_2$— may each independently be substituted with —O—, —S—, —CH═CH—, —CF═CF—, or —C≡C—, any hydrogen atom in the alkyl group may be substituted with a fluorine atom, and when there are more than one $L^{W1}$, they may be the same or different, $$W^2\text{-}LG^2 \quad \text{(I-A)}$$

where $W^2$ represents a linear or branched alkyl group having 1 to 20 carbon atoms, in which one —$CH_2$— or two or more non-adjacent —$CH_2$— may each independently be substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, and any hydrogen atom in the alkyl group may be substituted with a fluorine atom, or $W^2$ may represent a group represented by $P^W$—$(Sp^W—X^W)_{kW}$—, where: $P^W$ Represents a Polymerizable Group; $Sp^W$ represents a spacer group; when there are more than one $Sp^W$, they may be the same or different; $X^W$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—N═CH—, —CF═CF—, —C≡C—, or a single bond; when there are more than one $X^W$, they may be the same or different, however, $P^W$—$(Sp^W—X^W)_{kW}$— does not contain an —O—O— bond; and kW represents an integer of 0 to 10, and $LG^2$ represents a leaving group, (I-C)

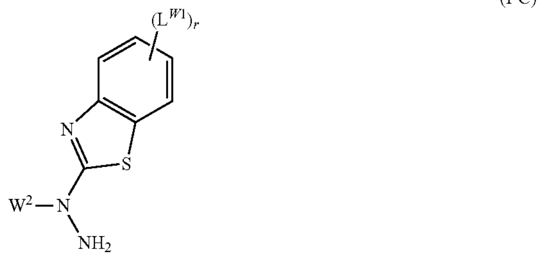

where, $W^2$, r, and $L^{W1}$ are the same as those described above, (I-D)

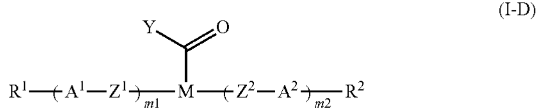

where $R^1$ represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms, in which any hydrogen atom may be substituted with a fluorine atom, and one —$CH_2$— or two or more non-adjacent —$CH_2$— may each independently be substituted with —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—N═CH—, —CF═CF—, or —C≡C—; or $R^1$ represents a group represented by $P^1$—$(Sp^1\text{-}X^1)_{k1}$— where: $P^1$ represents a polymerizable group; $Sp^1$ represents a spacer group; when there are more than one $Sp^1$, they may be the same or different; $X^1$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—N═CH—, —CF═CF—, —C≡C—, or a single bond; when there are more than one $X^1$, they may be the same or different; and k1 represents an integer of 0 to 10, $R^2$ represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms, in which any hydrogen atom may be substituted with a fluorine atom and one —$CH_2$— or two or more non-adjacent —$CH_2$— may each independently be substituted with —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—N═CH—, —CF═CF—, or —C≡C—; or $R^2$ represents a group represented by —$(X^2—Sp^2)_{k2}$—$P^2$ where: $P^2$ represents a polymerizable group; $Sp^2$ represents a spacer group; when there are more than one $Sp^2$, they may be the same or different; $X^2$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—N═CH—, —CF═CF—, —C≡C—, or a single bond; when there are more than one $X^2$, they may be the same or different; and k2 represents an integer of 0 to 10, $A^1$ and $A^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, which may be unsubstituted or substituted with one or more substituents L; when there are more than one $A^1$, they may be the same or different; when there are more than one $A^2$, they may be the same or different; and L represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —$CH_2$— or two or more non-adjacent —$CH_2$— may each independently be substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C— and any hydrogen atom in the alkyl group may be substituted with a fluorine atom; or L may represent a group represented by $P^L$—$(Sp^L—X^L)_{kL}$—, where: $P^L$ represents a polymerizable group; $Sp^L$ represents a spacer group; when there are more than one $Sp^L$, they may be the same or different; $X^L$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH═CH—OCO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—N═CH—, —CF═CF—, —C≡C—, or a single bond; when there are more than one $X^L$, they may be the same or different; kL represents an integer of 0 to 10; and when there are more than one kL in the compound, they may be the same or different, $Z^1$ and $Z^2$ each independently represent —O—, —S—, —$OCH_2$—, —$CH_2O$—, —$CH_2CH_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —$SCH_2$—, —$CH_2S$—, —$CF_2O$—, —$OCF_2$—, —$CF_2S$—, —$SCF_2$—, —CH═CH—COO—, —CH═CH—OCO—, —COO—CH═CH—, —OCO—CH═CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH═CH—, —N═N—, —CH═N—, —N═CH—, —CH═N—N═CH—, —CF═CF—, or a single bond; when there are more than one $Z^1$, they may be the same or different; when there are more than one $Z^2$, they may be the same or different; m1 and m2 each independently represent an integer of 1 to 6 and m1+m2 is an integer of 2 to 6; M represents a substituted or unsubstituted trivalent aromatic group; Y represents a hydrogen atom, a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —$CH^2$— or two or more non-adjacent —$CH^2$— may each independently be substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C— and any hydrogen atom in the alkyl group may be substituted with a fluorine atom; however, the compound represented by general formula (I-D) does not contain an —O—O— bond,

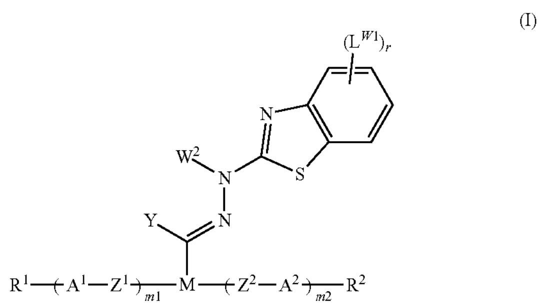

where $R^1$, $R^2$, $A^1$, $A^2$, $Z^1$, $Z^2$, m1, m2, M, Y, $W^2$, r, and $L^{W1}$ are the same as those in general formula (I-C) or general formula (I-D) described above.

2. The method for producing a compound represented by general formula (I) according to claim 1, wherein, in general formula (I-A), $LG^2$ represents a fluorine atom, a chlorine atom, a bromine atom, an iodine atom, a carbonyloxy group, an alkoxy group, a sulfonyloxy group, or a diazonium group.

3. The method for producing a compound represented by general formula (I) according to claim 1, wherein $W^2$ is a group selected from the group consisting of formulae (W2-a-1) to (W2-a-6):

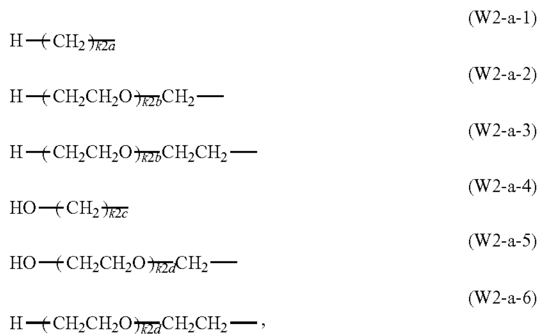

wherein k2a represents an integer of 2 to 20, k2b represents an integer of 1 to 6, k2c represents an integer of 3 to 20, and k2d represents an integer of 1 to 6.

4. The method for producing a compound represented by general formula (I) according to claim 3, wherein $W^2$ is a group represented by formula (W2-a-3) or formula (W2-a-6).

5. The method for producing a compound represented by general formula (I) according to claim 3, wherein m1 and m2 each independently represent an integer of 1 to 3.

6. The method for producing a compound represented by general formula (I) according to claim 1, wherein $Z^1$ and $Z^2$ directly bonded to M each independently represent —$OCH_2$— or —$CH_2O$—.

7. The method for producing a compound represented by general formula (I) according to claim 1, wherein Z' directly bonded to M represents —$OCH_2$— or —$CH_2O$—.

8. The method for producing a compound represented by general formula (I) according to claim 1, wherein $Z^2$ directly bonded to M represents —$OCH_2$— or —$CH_2O$—.

* * * * *